United States Patent
Kesten et al.

(10) Patent No.: US 9,433,437 B2
(45) Date of Patent: Sep. 6, 2016

(54) APPARATUS AND METHOD FOR TREATMENT OF ETHMOID SINUSITIS

(71) Applicant: Acclarent, Inc., Menlo Park, CA (US)

(72) Inventors: Randy J. Kesten, Mountain View, CA (US); Howard Levine, Longboat Key, FL (US); John W. White, Menlo Park, CA (US); Thomas R. Jenkins, Alameda, CA (US); Jessica M. Liberatore, San Mateo, CA (US); Jayakar V. Nayak, Stanford, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 13/837,104

(22) Filed: Mar. 15, 2013

(65) Prior Publication Data

US 2014/0276328 A1     Sep. 18, 2014

(51) Int. Cl.
*A61B 17/34* (2006.01)
*A61M 27/00* (2006.01)
*A61B 17/24* (2006.01)
(Continued)

(52) U.S. Cl.
CPC .......... *A61B 17/3478* (2013.01); *A61B 17/24* (2013.01); *A61B 17/12104* (2013.01); *A61B 2017/00331* (2013.01); *A61B 2017/12004* (2013.01); *A61B 2017/320004* (2013.01); *A61B 2017/3454* (2013.01); *A61F 13/20* (2013.01); *A61F 13/2022* (2013.01);
(Continued)

(58) Field of Classification Search
CPC .............. A61B 17/34; A61B 17/1688; A61B 2017/1785; A61B 17/24; A61B 17/3415; A61B 17/3468; A61B 2017/3437; A61B 17/3478; A61B 17/12104; A61M 27/00; A61M 29/02; A61M 2210/06; A61M 2210/0618; A61M 2210/0681; A61M 2210/0687; A61M 2210/0693; A61M 29/00; A61M 25/04; A61M 2025/0226; A61M 2029/025; A61F 11/004; A61F 2/18; A61F 2/186; A61F 2210/0061
See application file for complete search history.

(56) References Cited

U.S. PATENT DOCUMENTS

| 446,173 A | 2/1891 | Hancock |
| 504,424 A | 9/1893 | De Pezzer |

(Continued)

FOREIGN PATENT DOCUMENTS

| CH | 668188 | 12/1988 |
| CN | 2151720 | 1/1994 |

(Continued)

OTHER PUBLICATIONS

Suh; Kyung Shik. Paranasal Sinuses: Sagittal Anatomy with CT images. http://ws.ajou.ac.kr/~ent/new/case_topic/RHINODATA/sagittalPNS.htm. May 18, 1998. Accessed Feb. 20, 2015.*

(Continued)

Primary Examiner — Adam Marcetich
(74) Attorney, Agent, or Firm — Frost Brown Todd LLC

(57) ABSTRACT

Fluid communication may be improved for an ethmoid sinus by installing a port or wick in the wall of the ethmoid sinus to provide a fluid passageway across the wall of the ethmoid sinus. Fluid communication for an ethmoid sinus may also be improved by inflating a balloon in a retrobullar space, remodeling the posterior wall of the ethmoid bulla to expand the transition area in the retrobullar space. In addition, a wall defining the retrobullar space may be pierced to provide a passageway for fluid communication.

8 Claims, 49 Drawing Sheets

(51) Int. Cl.
  *A61M 29/02* (2006.01)
  *A61F 13/20* (2006.01)
  *A61B 17/12* (2006.01)
  *A61M 1/00* (2006.01)
  *A61B 17/00* (2006.01)
  *A61B 17/32* (2006.01)

(52) U.S. Cl.
  CPC .............. *A61M 1/008* (2013.01); *A61M 29/02* (2013.01); *A61M 2210/0618* (2013.01)

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,525,183 A | 3/1947 | Robinson |
| 2,493,326 A | 1/1950 | Trinder |
| 2,847,997 A | 8/1958 | Tibone |
| 2,899,227 A | 8/1959 | Gschwend |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,076,637 A | 2/1963 | Moziek |
| 3,173,418 A | 3/1965 | baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,968,846 A | 7/1976 | Brenner |
| 3,976,077 A | 8/1976 | Kerfoot |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,177,797 A | 12/1979 | Baylis et al. |
| 4,184,497 A | 1/1980 | Kolff et al. |
| 4,191,191 A | 3/1980 | Auburn |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,248,248 A | 2/1981 | Busscher |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,332,322 A | 6/1982 | Jaeschke et al. |
| 4,338,941 A | 7/1982 | Payton |
| D269,204 S | 5/1983 | Trepp |
| 4,388,941 A | 6/1983 | Reidhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zenter et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 E | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |

(56) References Cited

U.S. PATENT DOCUMENTS

| | | |
|---|---|---|
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,047,040 A | 9/1991 | Simpson et al. |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | lind |
| 5,069,226 A | 12/1991 | Yamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Skockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wttermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,258,003 A | 11/1993 | Ciaglia et al. |
| 5,263,926 A | 11/1993 | Wilk |
| 5,264,260 A | 11/1993 | Saab |
| 5,267,965 A | 12/1993 | Deneiga |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,353,804 A | 10/1994 | Kornberg et al. |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,403,338 A | 4/1995 | Milo |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,615,839 A | 4/1997 | Hartwig |
| 5,617,870 A | 4/1997 | Hastings et al. |
| 5,626,374 A | 5/1997 | Kim |
| 5,633,000 A | 5/1997 | Grossman et al. |

(56) References Cited

U.S. PATENT DOCUMENTS

| | | |
|---|---|---|
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterwreck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,030,402 A | 2/2000 | Thompson et al. |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,106,538 A | 8/2000 | Shiber |
| 6,109,268 A | 8/2000 | Thapliyal et al. |
| 6,113,567 A | 9/2000 | becker |
| 6,117,105 A | 9/2000 | Bresnaham et al. |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hegde et al. |

(56) References Cited

U.S. PATENT DOCUMENTS

| | | |
|---|---|---|
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,591,130 B2 | 7/2003 | Shahidi |
| 6,596,009 B1 | 7/2003 | Jelic |
| 6,607,546 B1 | 8/2003 | Murken |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,726,701 B2 | 4/2004 | Gilson et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,814,743 B2 | 11/2004 | Chin et al. |
| 6,817,364 B2 | 11/2004 | Garibaldi et al. |
| 6,817,976 B2 | 11/2004 | Rovengo |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,381 B2 | 3/2006 | Janssens |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,125,252 B2 | 10/2006 | Rouiller et al. |
| 7,128,718 B2 | 10/2006 | Hojeibane et al. |

(56) References Cited

U.S. PATENT DOCUMENTS

| | | | |
|---|---|---|---|
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,088 B2 | 6/2007 | Pintor et al. |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,258,694 B1 | 8/2007 | Choi et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| D586,465 S | 2/2009 | Faulkner et al. |
| D586,916 S | 2/2009 | Faulkner et al. |
| 7,485,125 B2 | 2/2009 | Sjostrom |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,569,056 B2 | 8/2009 | Cragg et al. |
| 7,615,005 B2 | 11/2009 | Stefanchik et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,717,933 B2 | 5/2010 | Becker |
| 7,720,521 B2 | 5/2010 | Chang et al. |
| 7,727,186 B2 | 6/2010 | Makower et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,771,482 B1 * | 8/2010 | Karmon .................. 623/17.17 |
| 7,775,968 B2 | 8/2010 | Mathis |
| 7,799,048 B2 | 9/2010 | Hudson et al. |
| 7,803,150 B2 | 9/2010 | Chang et al. |
| 7,806,871 B2 | 10/2010 | Li et al. |
| 7,837,672 B2 | 11/2010 | Intoccia |
| 7,840,254 B2 | 11/2010 | Glossop |
| 7,849,938 B1 | 12/2010 | Maier |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,905,896 B2 | 3/2011 | Straub |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,167,821 B2 | 5/2012 | Sharrow |
| 8,172,863 B2 | 5/2012 | Robinson et al. |
| 8,190,389 B2 | 5/2012 | Kim et al. |
| 8,197,552 B2 | 6/2012 | Mandpe |
| 8,239,001 B2 * | 8/2012 | Verard et al. ................. 600/424 |
| 8,241,266 B2 | 8/2012 | Keith et al. |
| 8,317,816 B2 | 11/2012 | Becker |
| 8,439,687 B1 | 5/2013 | Morriss et al. |
| 8,480,696 B2 | 7/2013 | Clague et al. |
| 8,647,256 B2 | 2/2014 | Carrillo |
| 8,882,697 B2 | 11/2014 | Celermajer et al. |
| 2001/0001124 A1 | 5/2001 | Mueller |
| 2001/0004644 A1 | 6/2001 | Levin |
| 2001/0034530 A1 | 10/2001 | Malackowski et al. |
| 2001/0051761 A1 | 12/2001 | Khadem |
| 2001/0051802 A1 | 12/2001 | Woloszko et al. |
| 2002/0006961 A1 | 1/2002 | Katz et al. |
| 2002/0038130 A1 | 3/2002 | Adams |
| 2002/0055746 A1 | 5/2002 | Burke et al. |
| 2002/0090388 A1 | 7/2002 | Humes et al. |
| 2002/0111603 A1 * | 8/2002 | Cheikh ..................... 604/891.1 |
| 2002/0116011 A1 | 8/2002 | Chee et al. |
| 2002/0138091 A1 | 9/2002 | Pflueger |
| 2003/0013985 A1 | 1/2003 | Saadat |
| 2003/0014008 A1 | 1/2003 | Jacques |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0078608 A1 | 4/2003 | Shiu |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2003/0212446 A1 | 11/2003 | Kaplan et al. |
| 2004/0015150 A1 | 1/2004 | Zadno-Azizi |
| 2004/0018980 A1 | 1/2004 | Gurney et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |

(56) References Cited

U.S. PATENT DOCUMENTS

| | | |
|---|---|---|
| 2005/0055077 A1 | 3/2005 | Marco |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113686 A1 | 5/2005 | Peckham |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2005/0273132 A1 | 12/2005 | Shluzas et al. |
| 2005/0283221 A1 | 12/2005 | Mann et al. |
| 2006/0004323 A1 | 1/2006 | Chang et al. |
| 2006/0004368 A1* | 1/2006 | Zaleski et al. ............... 606/75 |
| 2006/0058837 A1 | 3/2006 | Bose et al. |
| 2006/0063973 A1 | 3/2006 | Makower et al. |
| 2006/0074318 A1 | 4/2006 | Ahmed et al. |
| 2006/0085027 A1 | 4/2006 | Santin et al. |
| 2006/0095066 A1* | 5/2006 | Chang et al. ............... 606/199 |
| 2006/0142736 A1* | 6/2006 | Hissink ............... A61F 11/002 604/540 |
| 2006/0161255 A1 | 7/2006 | Zarowski et al. |
| 2006/0173382 A1 | 8/2006 | Schreiner |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2007/0005094 A1* | 1/2007 | Eaton et al. ............... 606/199 |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0233036 A1 | 10/2007 | Madpe |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0288036 A1 | 12/2007 | Seshadri et al. |
| 2007/0293727 A1 | 12/2007 | Goldfarb et al. |
| 2007/0293946 A1 | 12/2007 | Gonzales et al. |
| 2008/0004676 A1* | 1/2008 | Osypka et al. ............... 607/59 |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0183128 A1 | 7/2008 | Morriss et al. |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0228231 A1 | 9/2008 | Raphael et al. |
| 2008/0262508 A1 | 10/2008 | Clifford et al. |
| 2008/0262509 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0088677 A1 | 4/2009 | Cohen |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0227945 A1 | 9/2009 | Eaton et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0087811 A1 | 4/2010 | Herrin et al. |
| 2010/0114066 A1 | 5/2010 | Makower et al. |
| 2010/0125253 A1 | 5/2010 | Olson et al. |
| 2010/0174308 A1 | 7/2010 | Chang et al. |
| 2010/0174366 A1 | 7/2010 | Avior |
| 2010/0198191 A1 | 8/2010 | Clifford et al. |
| 2010/0198302 A1 | 8/2010 | Shalev |
| 2010/0274188 A1 | 10/2010 | Chang et al. |
| 2010/0290244 A1 | 11/2010 | Nath |
| 2011/0004057 A1 | 1/2011 | Goldfarb et al. |
| 2011/0015612 A1* | 1/2011 | Arcand ............... A61F 2/18 604/514 |
| 2011/0015645 A1 | 1/2011 | Liu et al. |
| 2011/0040320 A1* | 2/2011 | Keith et al. ............... 606/199 |
| 2011/0046682 A1* | 2/2011 | Stephan et al. ............... 606/305 |
| 2011/0166190 A1 | 7/2011 | Anderson et al. |
| 2011/0202059 A1* | 8/2011 | Webb et al. ............... 606/59 |
| 2012/0053567 A1* | 3/2012 | Schreck et al. ............... 604/514 |
| 2012/0078118 A1 | 3/2012 | Jenkins et al. |
| 2012/0109111 A1* | 5/2012 | Li ............... 604/543 |
| 2012/0184983 A1 | 7/2012 | Chang et al. |
| 2012/0316572 A1 | 12/2012 | Rosenblatt et al. |
| 2014/0277039 A1 | 9/2014 | Liberatore et al. |
| 2014/0277043 A1 | 9/2014 | Jenkins et al. |

FOREIGN PATENT DOCUMENTS

| | | |
|---|---|---|
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |

(56) References Cited

FOREIGN PATENT DOCUMENTS

| | | | |
|---|---|---|---|
| JP | 2005-532869 | 11/2005 | |
| RU | 2213530 | 10/2003 | |
| SU | 1662571 | 7/1991 | |
| WO | WO 90/11053 | 10/1990 | |
| WO | WO 90/14865 | 12/1990 | |
| WO | WO 91/17787 | 11/1991 | |
| WO | WO 92/15286 | 9/1992 | |
| WO | WO 92/22350 | 12/1992 | |
| WO | WO 94/12095 | 6/1994 | |
| WO | WO 96/29071 | 9/1996 | |
| WO | WO 97/21461 | 6/1997 | |
| WO | WO 99/24106 | 5/1999 | |
| WO | WO 99/30655 | 6/1999 | |
| WO | WO 99/32041 | 7/1999 | |
| WO | WO 00/09192 | 2/2000 | |
| WO | WO 00/23009 | 4/2000 | |
| WO | WO 00/51672 | 9/2000 | |
| WO | WO 00/53252 | 9/2000 | |
| WO | WO 01/45572 | 6/2001 | |
| WO | WO 01/54558 | 8/2001 | |
| WO | WO 01/56481 | 8/2001 | |
| WO | WO 01/70325 | 9/2001 | |
| WO | WO 01/74266 | 10/2001 | |
| WO | WO 01/97895 | 12/2001 | |
| WO | WO 02/47561 | 6/2002 | |
| WO | WO 02/062269 | 8/2002 | |
| WO | WO 03/049603 | 6/2003 | |
| WO | WO 03/063703 | 8/2003 | |
| WO | WO 03/105657 | 12/2003 | |
| WO | WO 2004/006788 | 1/2004 | |
| WO | WO 2004/018980 | 3/2004 | |
| WO | WO 2004/026391 | 4/2004 | |
| WO | WO 2004/082525 A2 | 9/2004 | |
| WO | WO 2004/082525 A3 | 9/2004 | |
| WO | WO 2005/018730 | 3/2005 | |
| WO | WO 2005/077450 | 8/2005 | |
| WO | WO 2005/089670 | 9/2005 | |
| WO | WO 2005/117755 | 12/2005 | |
| WO | WO 2006/034008 | 3/2006 | |
| WO | WO 2006/078884 | 7/2006 | |
| WO | WO 2006/107957 | 10/2006 | |
| WO | WO 2006/116597 | 11/2006 | |
| WO | WO 2006/118737 | 11/2006 | |
| WO | WO 2006/135853 | 12/2006 | |
| WO | WO 2007062668 A1 * | 6/2007 | ......... A61M 31/002 |
| WO | WO 2007/111636 | 10/2007 | |
| WO | WO 2007/124260 | 11/2007 | |
| WO | WO 2008/036149 | 3/2008 | |
| WO | WO 2008/045242 | 4/2008 | |
| WO | WO 2008/051918 | 5/2008 | |
| WO | WO 2008/134382 | 11/2008 | |

OTHER PUBLICATIONS

U.S. Appl. No. 11/789,705, filed Apr. 24, 2007, Morriss et al.
U.S. Appl. No. 13/832,167, filed Mar. 15, 2013, Kesten et al.
U.S. Appl. No. 60/844,874, filed Sep. 15, 2006, Goldfarb.
U.S. Appl. No. 60/922,730, filed Apr. 9, 2007, Muni.
U.S. Appl. No. 61/052,413, filed May 12, 2008, Makower.
U.S. Appl. No. 61/084,949, filed Jul. 30, 2008, Goldfarb.
U.S. Appl. No. 61/725,523, filed Nov. 13, 2012, Johnson.
Argon Medical. Maxxim Medical. Ad for Sniper EliteTM Hydrophilic Ni—Ti Alloy Guidewire (2001).
Aust, R., et al. 'The Functional Size of the Human Maxillary Ostium in Vivo' Acta. Otolaryn. (1978) vol. 78 pp. 432-435
Baim, D.S., MD 'Grossman's Cardiac Catheterization, Angiography, and Intervention'(2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ner.html.
Bartal, N. 'An Improved stent for Use in the Surgical Management of Congential Posterior Choanal Atresia' J. Laryngol. Otol (1988) vol. 102 pp. 146-147.

Becker, A.E. 'Restenosis After Angioplasty' The Lancet (1988) vol. 331, No. 8584 p. 532.
Bellis, M. History of the Catheter-Balloon Catheter—Thomas Fogarty. Www.inventors.about.com./library/inventors.blcatheter. htm?p=1.
Benninger et al.; Adult Chronic Rhinosinusitis: Defintions, Diagnosis, Epidemioligy, and Pathophysilogy' Arch Otolarygol Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: the University of Miami Experience' American Journal of Rhinology, vol. 12, No. 5, (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery', Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers-General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Fluororouracil' Clinics (2007) vol. 62, Issue 1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.

(56) References Cited

OTHER PUBLICATIONS

Gatot, A. et al. 'Early treatment of Orbital Floor Fractures with Catheter Balloon in Children' Int. J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' vol. 69 (1994) pp. 195-198. Elesvier Sciences S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence ot Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE. (Mar. 2001).
Gottmann, et al. 'Successful treatment of Recurrent Post-Operative Frontal Sinus Stenoses by Balloon Dilatation' CIRSE. (Oct. 5, 2002).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from th Maxillary Artery' Scandinavian Journal of Plastic and reconstruction Sergery and Hand Surgery (1999) vol. 33 pp. 321-324.
Hojo, M. et al, 'Electrophilic Substitutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimental investigations on wound healing of the paranasal sinuses. II. Spontaneous wound closure and pharmacologic effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa.Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.

K-Splints Internal Nasal Splints; Jan. 25, 2007; www.invotec.net/rhinology/ksplint.html.
Kaiser, H. et al 'Cortizontherapie, Corticoide in Klinik and Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser. Www.xomcat.com//xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg.(1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polyactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.
Park, K. et al. 'Biodegradable Hydrogels for Drug Delivery' (1993) Technomic Publishing Inc. Lancaster.

(56) References Cited

OTHER PUBLICATIONS

Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems. Www.dymax.com/products/curing_equipment/lightguids/light. (2004) pp. 1-2.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
St. Croix, et al., 'Genes Expressed in Human Tumor Endothelium' Science (May 15, 2000) vol. 289 pp. 1197-1202.
Stammberger, H. 'Komplikationen entzundlicher Nasen-nebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgrnologisch gesteuerter Ballondilation (Sep. 25, 1999) pp. 1-4.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734.
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catherization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow.
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
European Communication dated Sep. 4, 2008 for Application No. EP 05773189.
European Communication dated Jun. 19, 2009 for Application No. EP 05773189.
European Exam Report dated Feb. 22, 2006 for Application No. 02716734.5.
European Exam Report dated Feb. 8, 2007 for Application No. 02716734.5.
Supplemental European Search Report and Written Opinion dated Sep. 11, 2009 for Application No. EP 06815174.
European Search Report dated Sep. 27, 2011 for Application No. EP 10182961.
European Search Report dated Sep. 29, 2011 for Application No. EP 10182893.
Partial European Search Report dated Sep. 20, 2007 for Application No. EP 07252018.
Partial European Search Report dated Mar. 25, 2008 for Application No. EP 07252018.
Supplemental European Search Report dated Jun. 2, 2008 for Application No. EP 05773189.
Supplemental Partial European Search Report dated Jul. 1, 2009 for Application No. EP 06815285.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.

(56) References Cited

OTHER PUBLICATIONS

Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental Partial European Search Report dated Nov. 19, 2010 for Application No. EP 06751637.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/36960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report and Written Opinion dated Aug. 17, 2007 for Application No. PCT/US05/13617.
International Search Report dated Aug. 29, 2007 for Application No. PCT/US06/002004.
International Search Report dated Sep. 25, 2007 for Application No. PCT/US06/37167.
International Search Report dated Oct. 19, 2007 for Application No. PCT/US07/03394.
International Search Report and Written Opinion dated May 29, 2008 for Application No. PCT/US07/021170.
International Search Report dated May 29, 2008 for Application No. PCT/US07/21922.
International Search Report and Written Opinion dated Jul. 1, 2008 for Application No. PCT/US06/22745.
International Search Report dated Jul. 3, 2008 for Application No. PCT/US2006/029695.
International Search Report dated Jul. 7, 2008 for Application No. PCT/US07/16213.
International Search Report dated Jul. 8, 2008 for Application No. PCT/US07/11474.
International Search Report dated Jul. 17, 2008 for Application No. PCT/US06/36960.
International Search Report and Written Opinion dated Jul. 21, 2008 for Application No. PCT/US05/33090.
International Search Report dated Aug. 25, 2008 for Application No. PCT/US2008/000911.
International Search Report dated Sep. 10, 2008 for Application No. PCT/US07/16212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/11449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.

(56) References Cited

OTHER PUBLICATIONS

USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
International Search Report dated Sep. 15, 2014 from PCT/US2014/021842.
Written Opinion dated Sep. 15, 2014 for Application No. PCT/US2014/021842.

\* cited by examiner

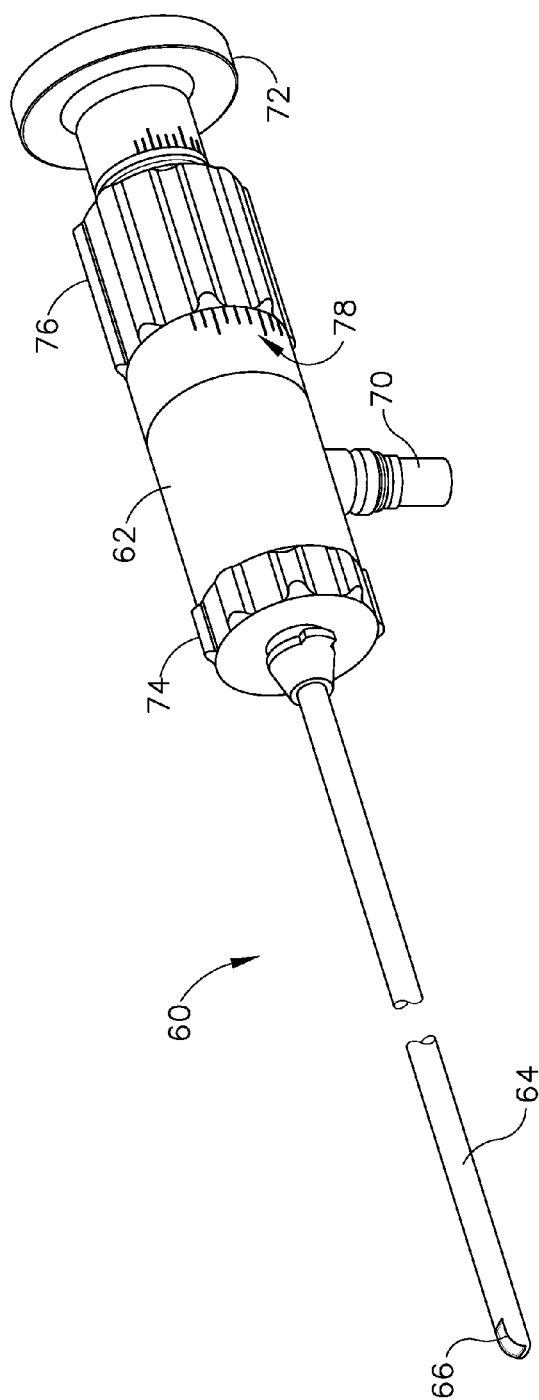
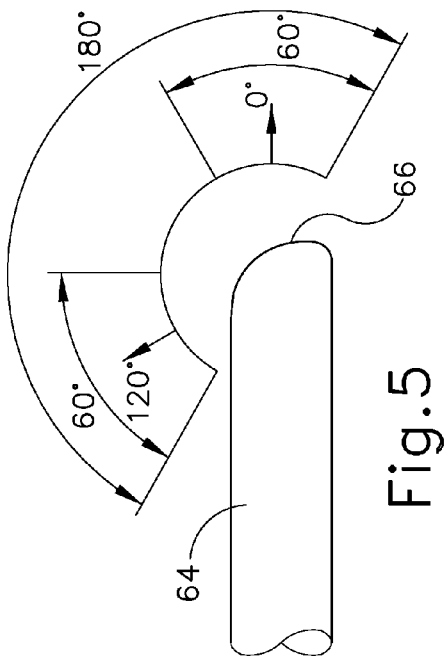
Fig.4
Fig.5

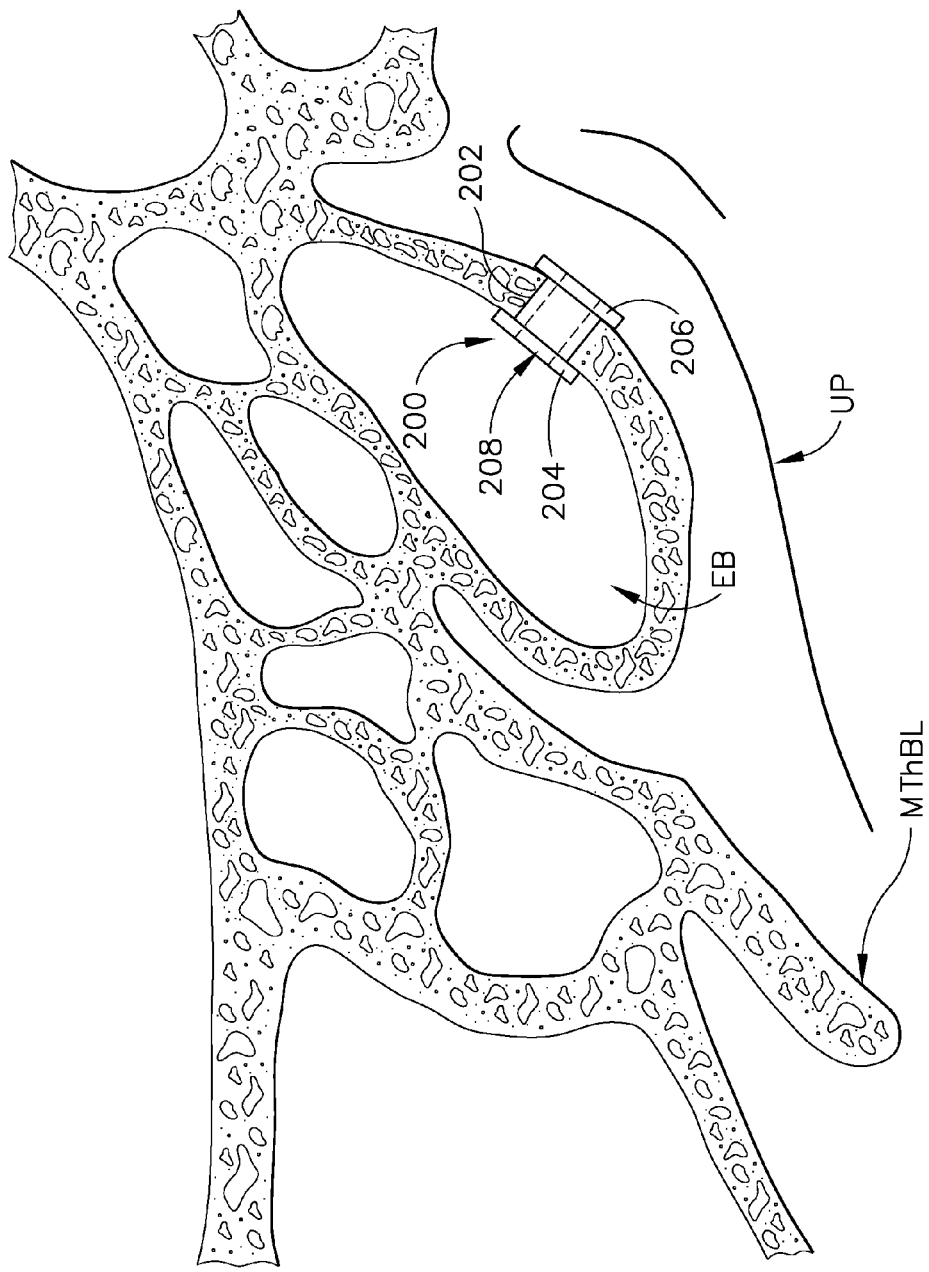

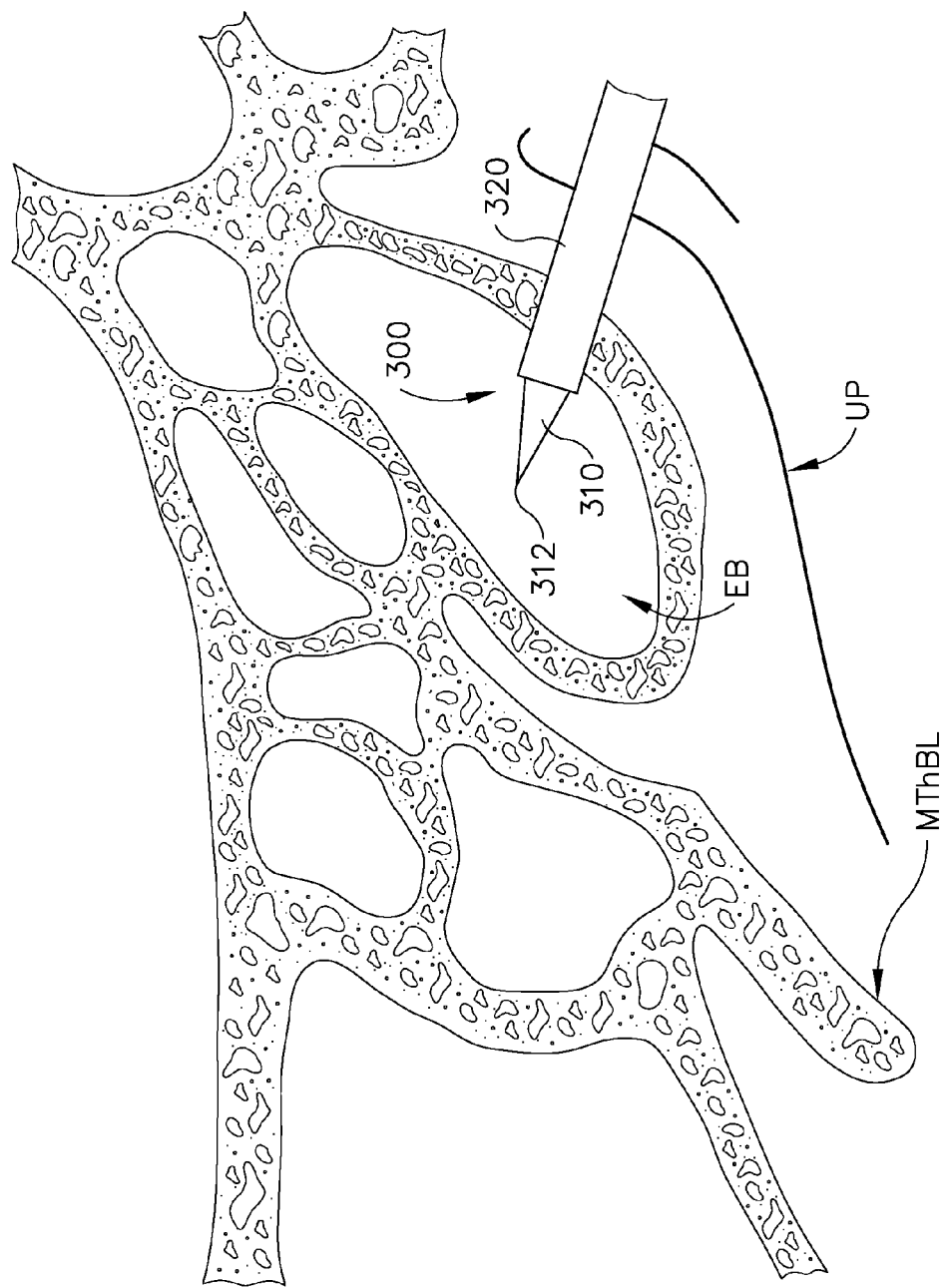

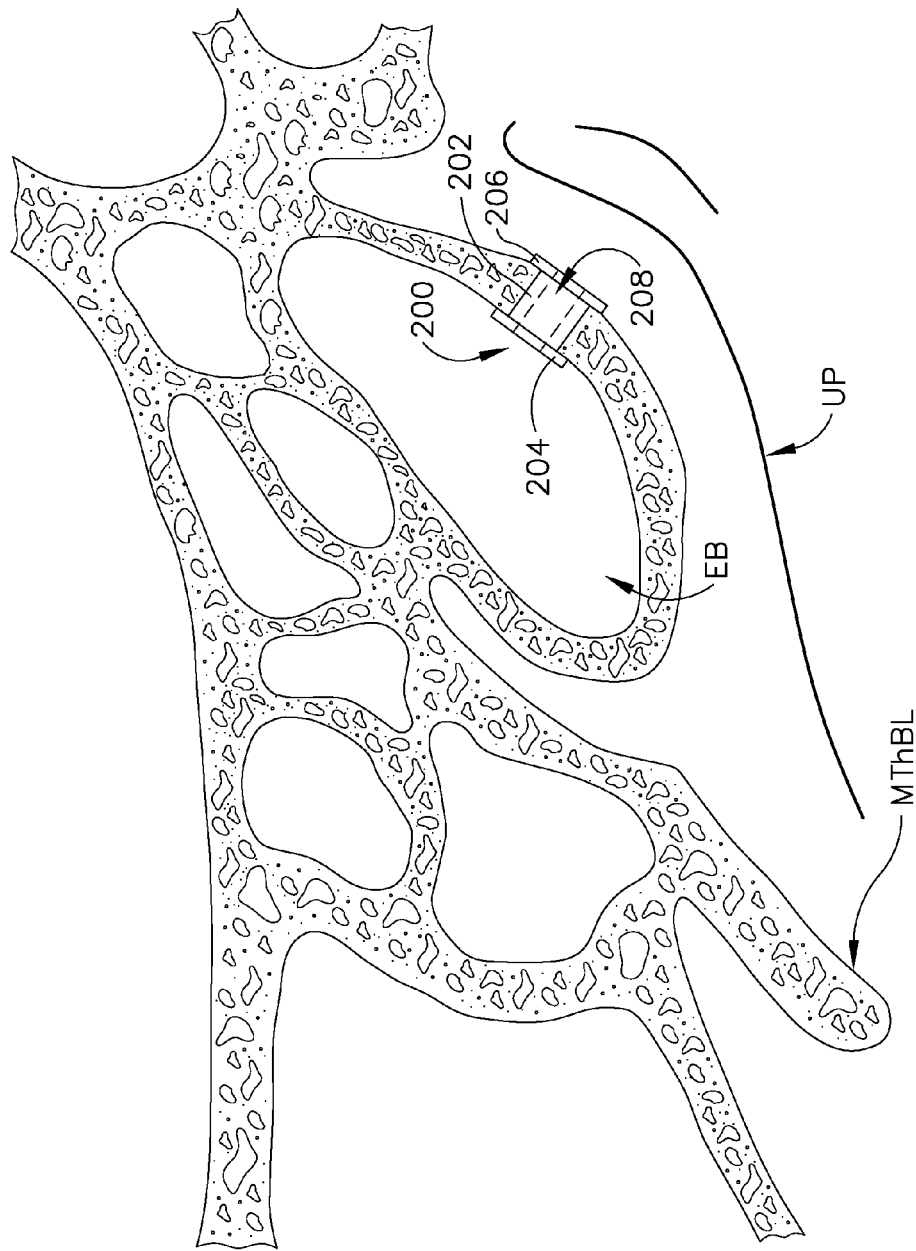

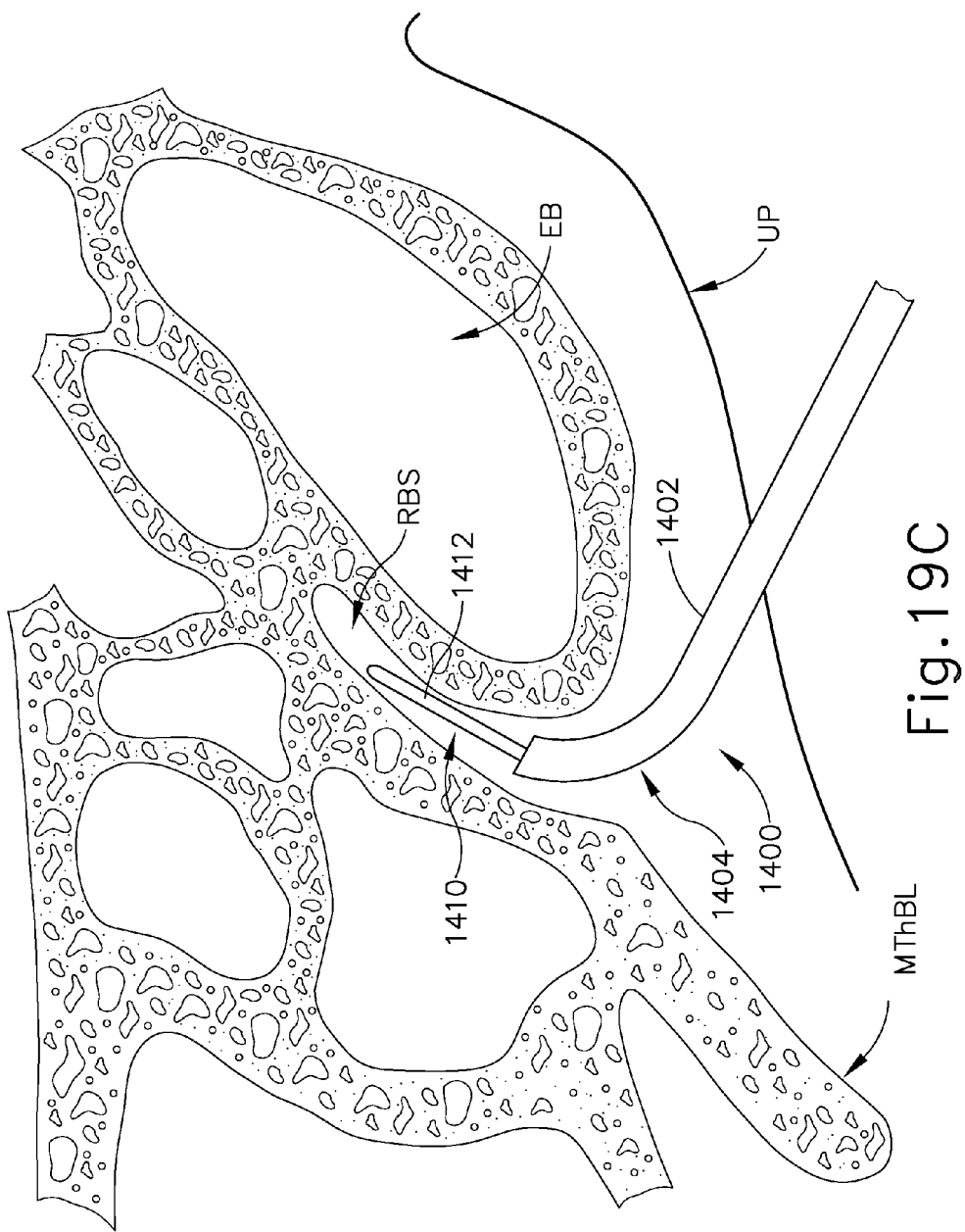

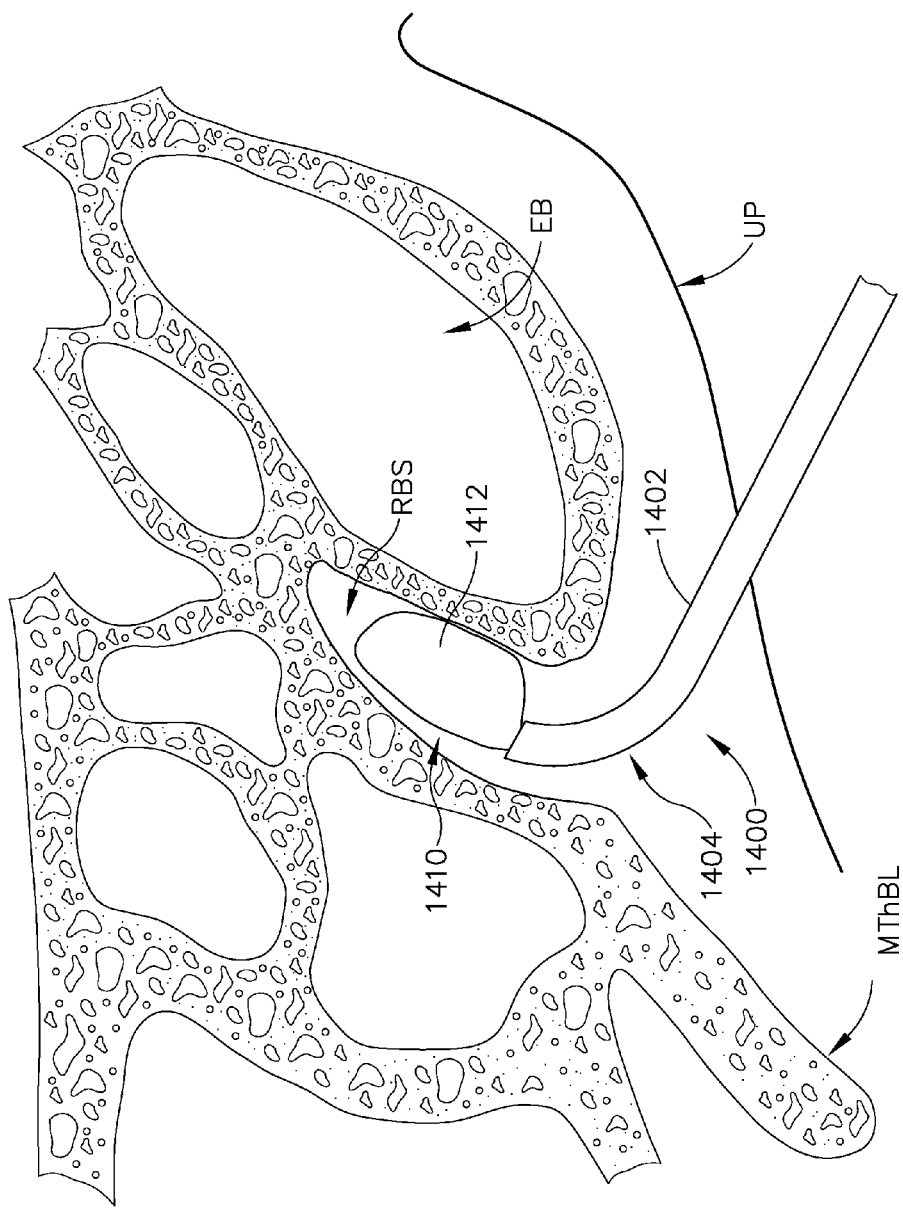

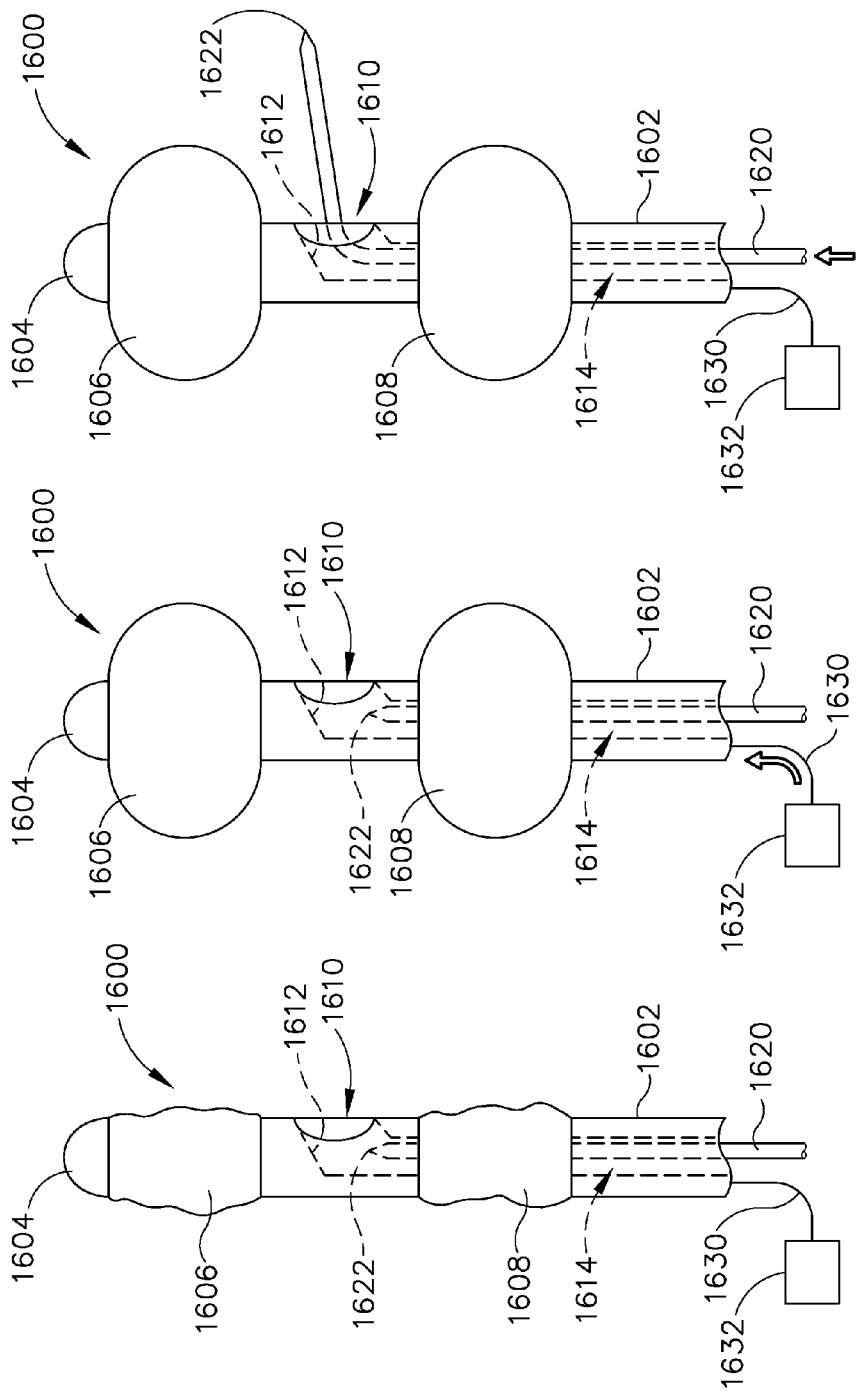

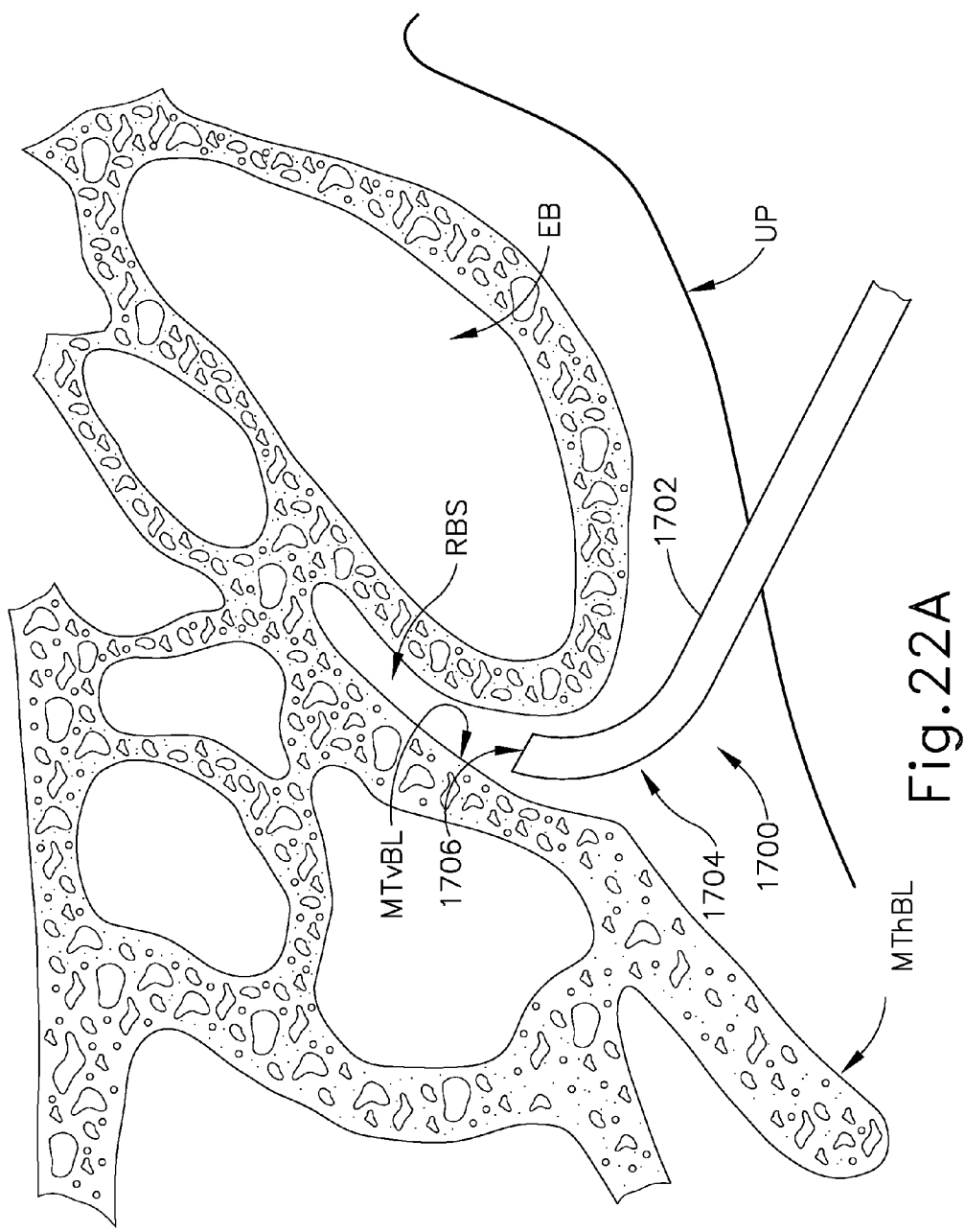

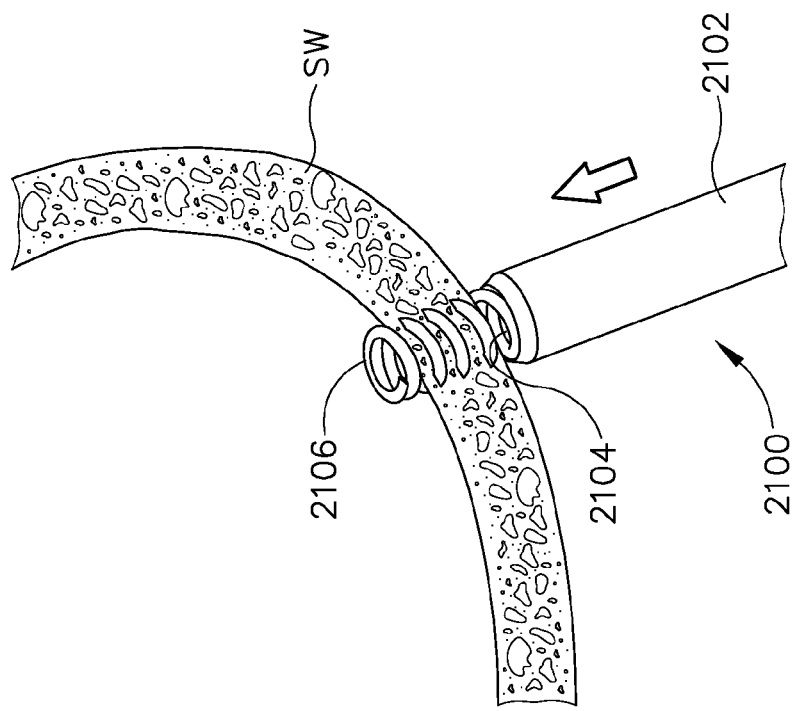
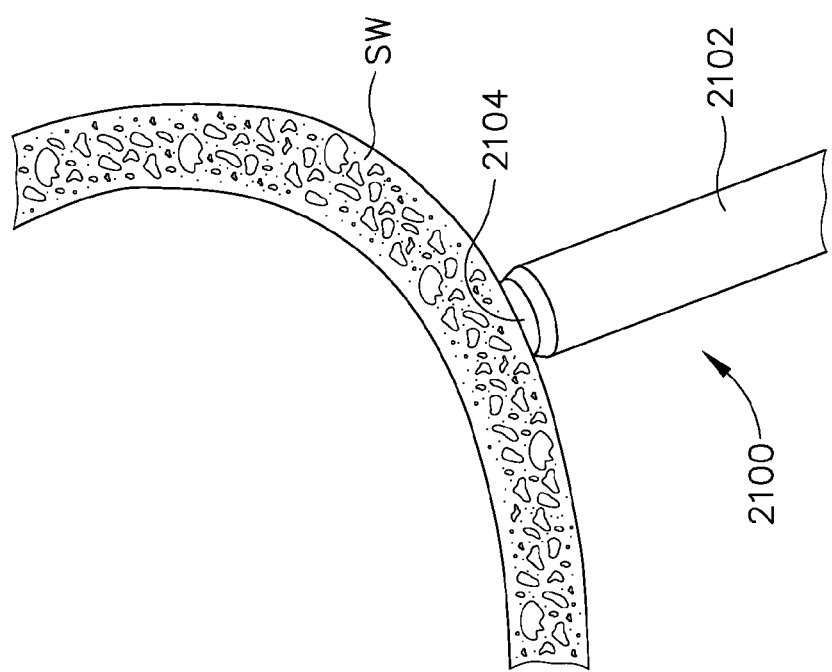

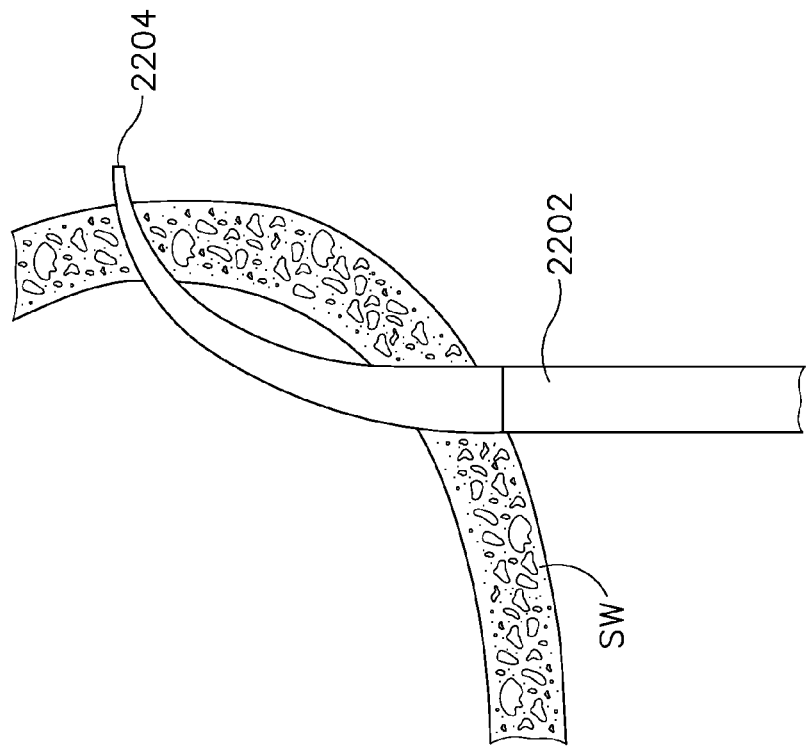
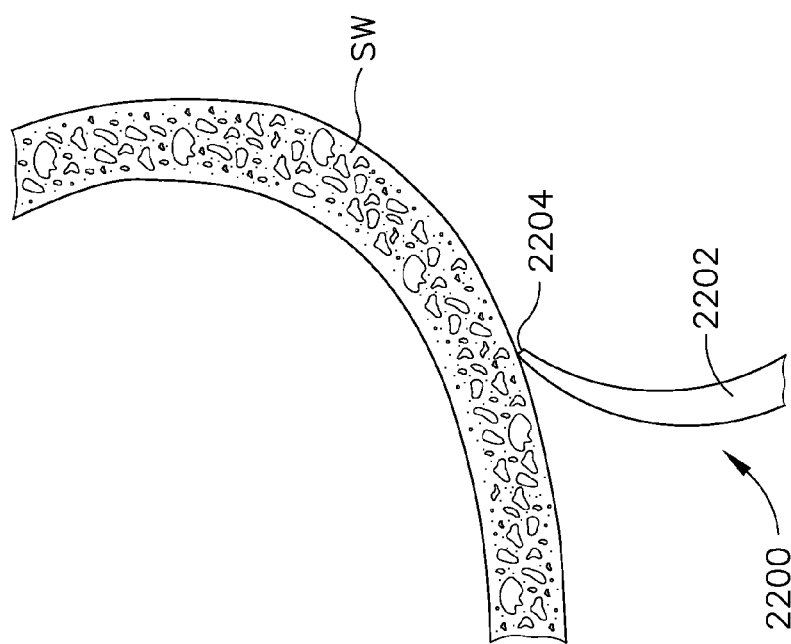
Fig. 27A
Fig. 27B

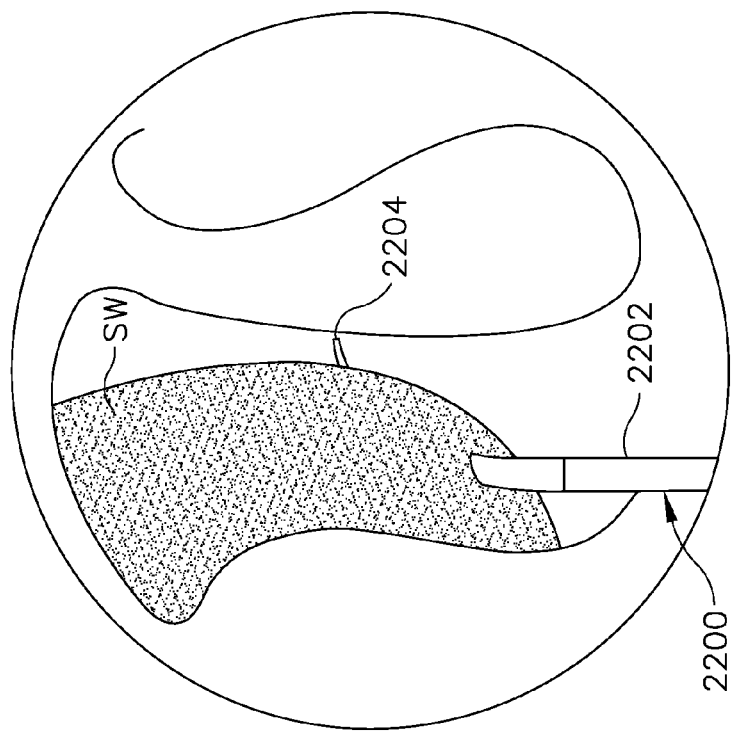
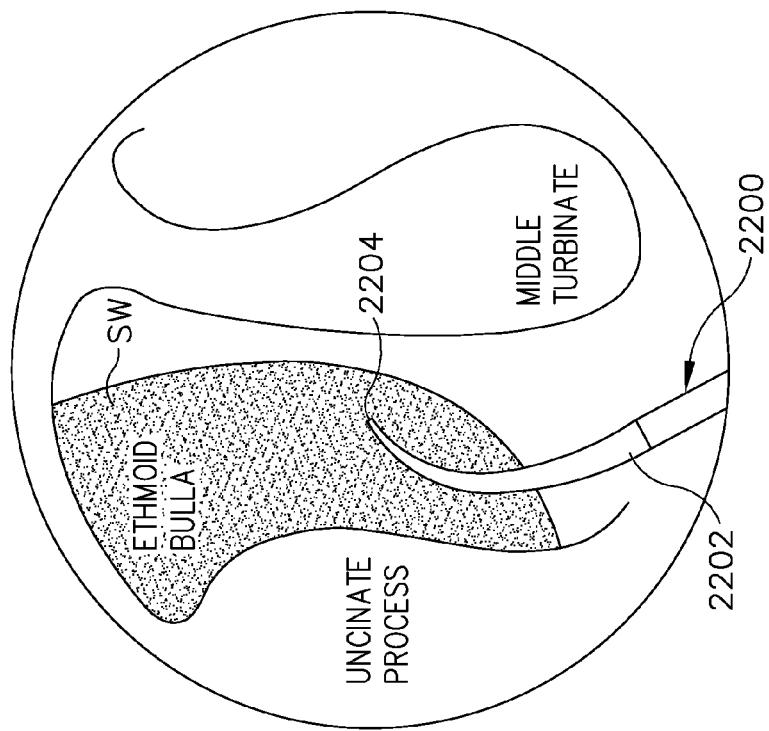
Fig.28A
Fig.28B

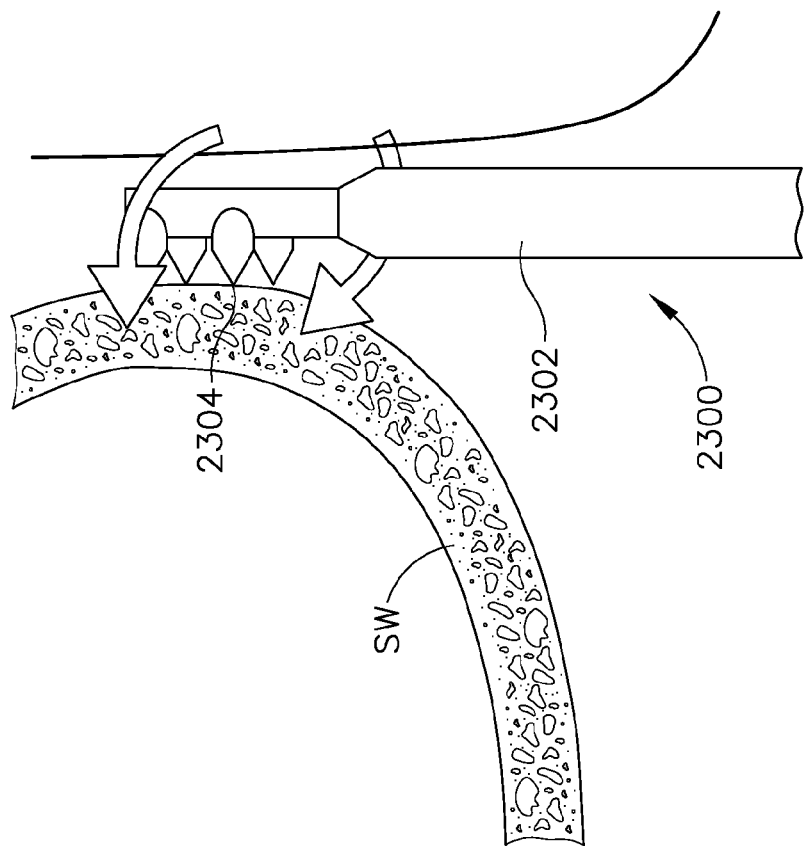
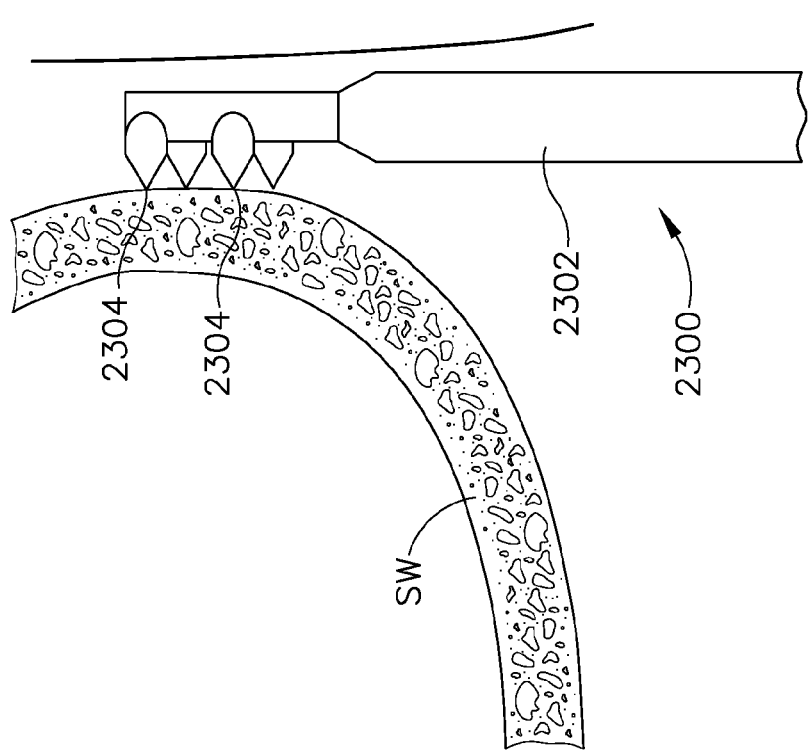
Fig. 29B
Fig. 29A

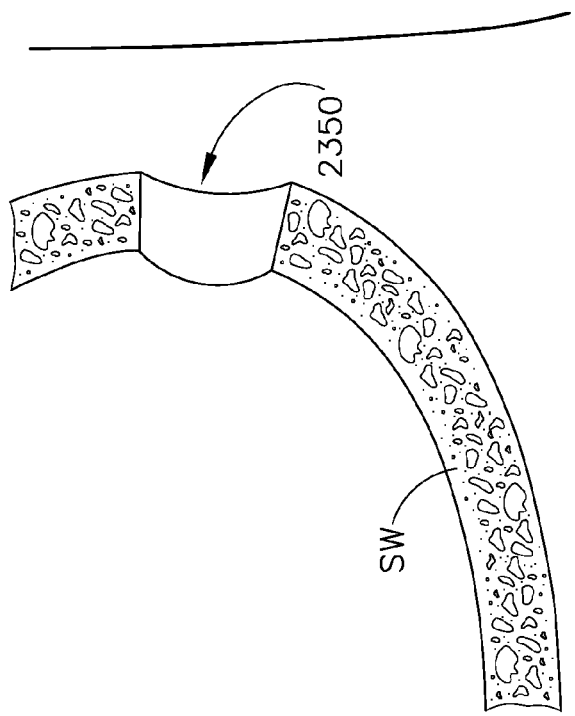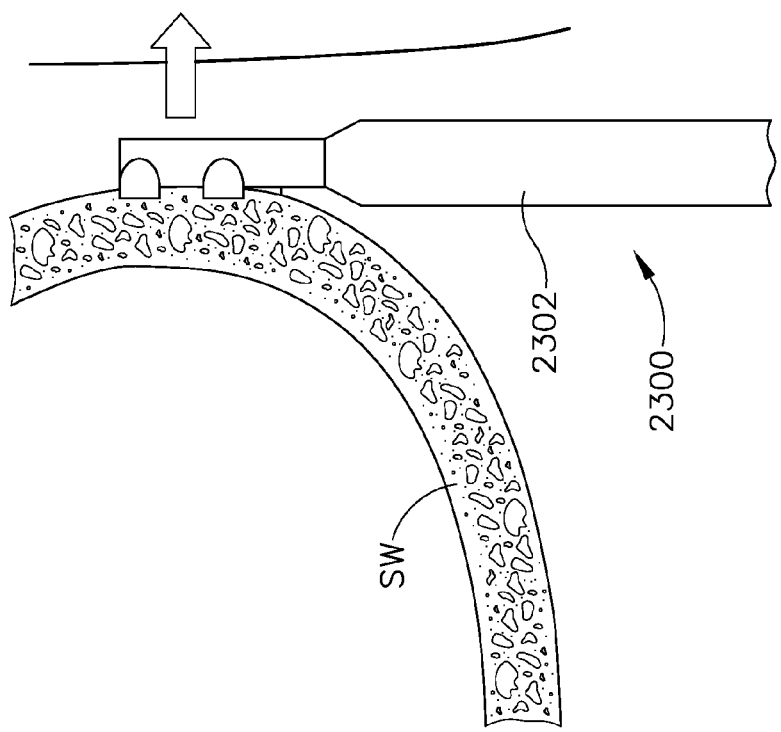

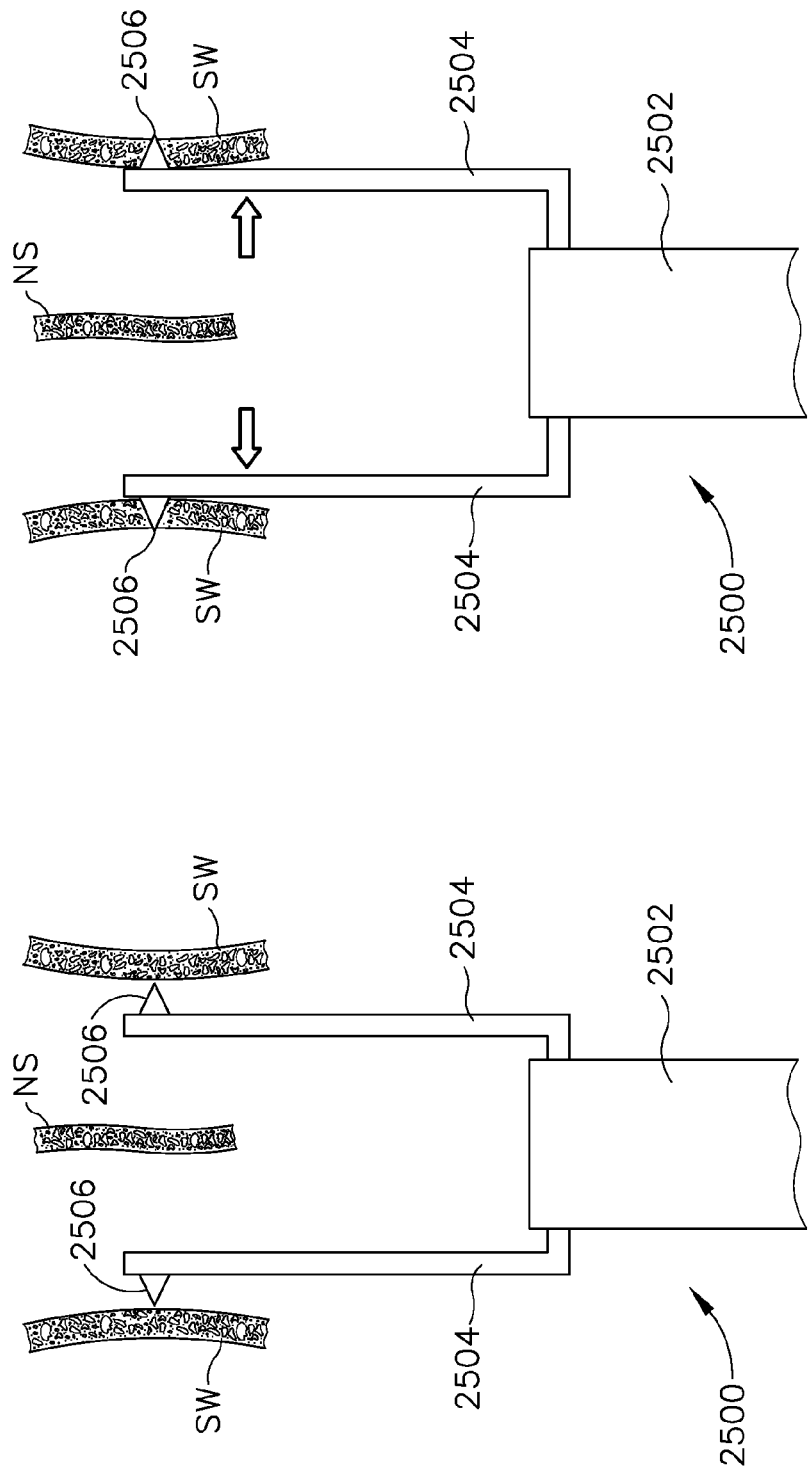

APPARATUS AND METHOD FOR TREATMENT OF ETHMOID SINUSITIS

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for treatment of anatomical passageways in a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 4 depicts depicts a perspective view of an exemplary endoscope suitable for use with the dilation catheter system of FIG. 1;

FIG. 5 depicts a side elevational view of the distal end of the endoscope of FIG. 5, showing an exemplary range of viewing angles;

FIG. 7B depicts a left sagittal cross-sectional view of a portion of a human head, with a port disposed in the pierced wall of the ethmoid bulla;

FIG. 8A depicts a left sagittal cross-sectional view of a portion of a human head, with another exemplary port deployment instrument piercing a wall of the ethmoid bulla;

FIG. 8D depicts a left sagittal cross-sectional view of a portion of a human head, with a port disposed in the pierced wall of the ethmoid bulla;

FIG. 19C depicts a left sagittal cross-sectional view of a portion of a human head, with a dilation catheter advanced through the guide catheter of FIG. 19B into the retrobullar space;

FIG. 19D depicts a left sagittal cross-sectional view of a portion of a human head, with a dilator of the dilation catheter of FIG. 19C in an inflated state in the retrobullar space;

FIG. 21A depicts a side elevational view of exemplary piercing catheter, with support balloons in a non-inflated state and with a piercing element in a retracted state;

FIG. 21B depicts a side elevational view of the piercing catheter of FIG. 21A, with the support balloons in an inflated state and with the piercing element in the retracted state;

FIG. 21C depicts a side elevational view of the piercing catheter of FIG. 21A, with the support balloons in an inflated state and with the piercing element in an advanced state;

FIG. 22A depicts a left sagittal cross-sectional view of a portion of a human head, with a guide catheter positioned at the retrobullar space;

FIG. 26A depicts an elevational view of the distal end of another exemplary alternative sinus wall piercing instrument positioned adjacent to a sinus wall, with the sinus wall in cross section, and with a piercing element in a retracted position;

FIG. 26B depicts an elevational view of the distal end of the piercing instrument of FIG. 26A, with the sinus wall in cross section, and with the piercing element advanced through the sinus wall;

FIG. 27A depicts an elevational view of the distal end of another exemplary alternative sinus wall piercing instrument positioned adjacent to a sinus wall, with the sinus wall in cross section, and with a wall cutter retracted out of view;

FIG. 27B depicts an elevational view of the distal end of the piercing instrument of FIG. 27A, with the sinus wall in cross section, with the piercing element advanced through the sinus wall, and with the wall cutter retracted out of view;

FIG. 28A depicts a perspective view of the distal end of the piercing element of FIG. 27A positioned adjacent to the sinus wall, with the wall cutter retracted out of view;

FIG. 28B depicts a perspective view of the distal end of the piercing element of FIG. 27A, with the piercing element advanced through the sinus wall, and with the wall cutter retracted out of view;

FIG. 29A depicts an elevational view of the distal end of another exemplary alternative sinus wall piercing instrument positioned adjacent to a sinus wall, with the sinus wall in cross section;

FIG. 29B depicts an elevational view of the distal end of the piercing instrument of FIG. 29A, with the sinus wall in cross section, with piercing elements advanced through the sinus wall;

FIG. 29C depicts an elevational view of the distal end of the piercing instrument of FIG. 29A, with the sinus wall in cross section, with the instrument being pulled away from the sinus wall while the piercing elements are disposed in the sinus wall;

FIG. 29D depicts a cross-sectional view of the sinus wall of FIG. 29A after completion of a procedure with the piercing instrument of FIG. 29A;

FIG. 32A depicts an elevational view of the distal end of another exemplary alternative sinus wall piercing instrument positioned adjacent to a sinus wall, with the sinus wall in cross section, and with arms of the instrument in retracted positions; and FIG. 32B depicts an elevational view of the distal end of the piercing instrument of FIG. 32A, with the sinus wall in cross section, and the with the arms of the instrument in laterally advanced positions.

Figure 1:
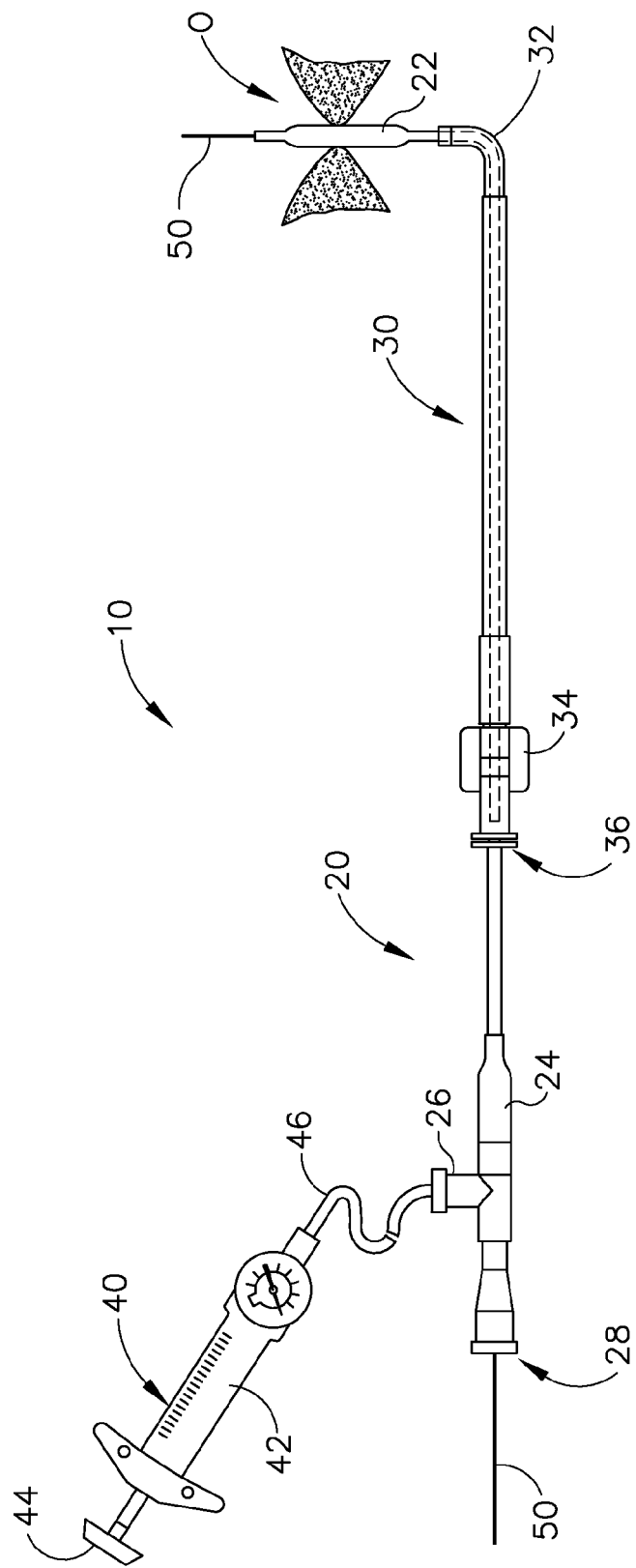
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. In some versions, inflator (40) is configured in accordance with at least some of the teachings of U.S. Pat. App. No. 61/725,523, entitled "Inflator for Dilation of Anatomical Passageway," filed Nov. 13, 2012, the disclosure of which is incorporated by reference herein. Other suitable forms that inflator (40) may take will be apparent to those of ordinary skill in the art in view of the teachings herein.

Figure 2:
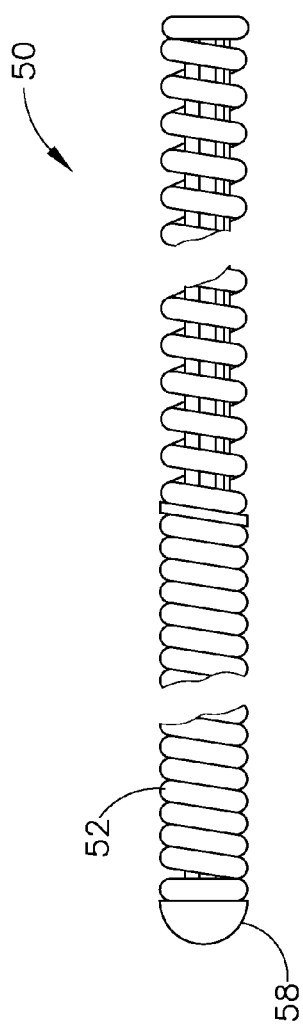
FIG. 2 depicts a side elevational view of an exemplary illuminating guidewire suitable for use with the dilation catheter system of FIG. 1.
Figure 3:
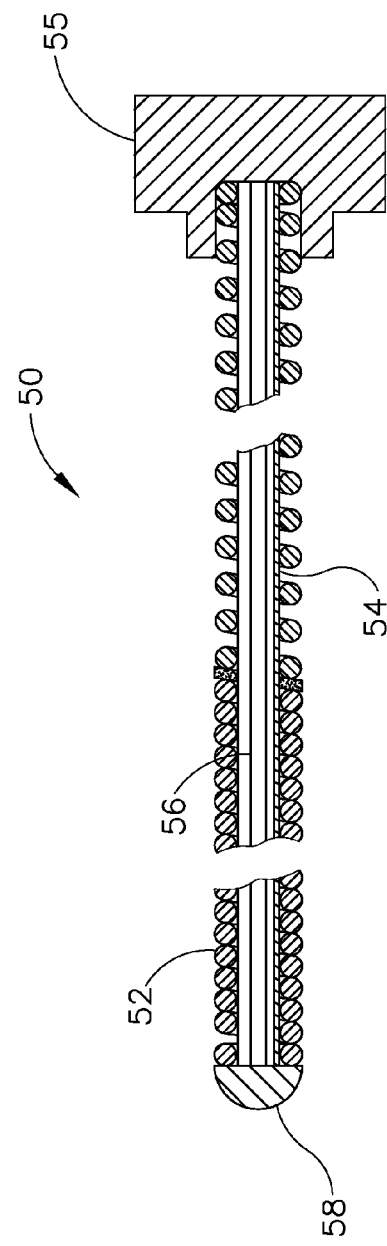
FIG. 3 depicts a side cross-sectional view of the illuminating guidewire of FIG. 2.

As best seen in FIGS. 2-3, guidewire (50) of the present example comprises a coil (52) positioned about a core wire (54). An illumination wire (56) extends along the interior of core wire (54) and terminates in an atraumatic lens (58). A connector (55) at the proximnal end of guidewire (50) enables optical coupling between illumination wire (56) and a light source (not shown). Illumination wire (56) may comprise one or more optical fibers. Lens (58) is configured to project light when illumination wire (56) is illuminated by the light source, such that illumination wire (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination wire (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

II. Overview of Exemplary Endoscope

As noted above, an endo scope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Port for Ethmoid Sinus

Figure 6:
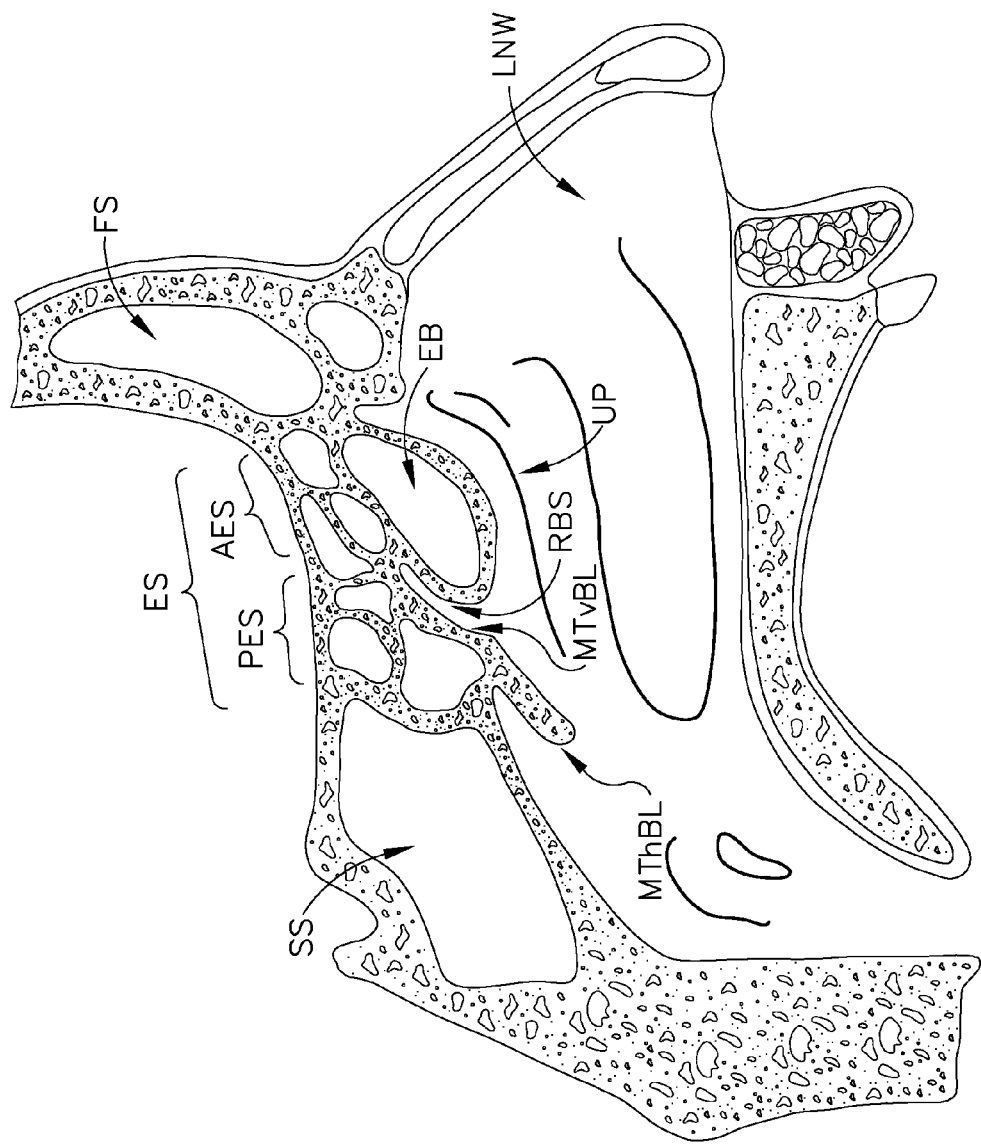
FIG. 6 depicts a left sagittal cross-sectional view of a portion of a human head, showing paranasal sinus structures.

FIG. 6 shows a left sagittal cross-sectional view of a portion of a human head, which includes a sphenoid sinus (SS), ethmoid sinus (ES), frontal sinus (FS), middle turbinate horizontal basal lamella (MThBL), middle turbinate vertical basal lamella (MTvBL), uncinate process (UP), and lateral nasal wall (LNW). The ethmoid sinus (ES) comprises a set of sinus cells that may be categorized as anterior ethmoid sinus (AES) cells and posterior ethmoid sinus (PES) cells. The ethmoid bulla (EB) is the largest ethmoid sinus (ES) cell, and is generally inferior and anterior to the other cells of the ethmoid sinus (ES). The posterior wall of the ethmoid bulla (EB) and the middle turbinate vertical basal lamella (MTvBL) together define a retrobullar space (RBS). It should be understood that anatomical variation in the human is such that this retrobullar space (RBS) may or may not be present in a given individual.

The ethmoid sinus (ES) includes ostia (not shown) for providing fluid communication to and from the cells of the ethmoid sinus (ES) and the nasal cavity. For instance, ostia may provide fluid paths for cells within the anterior ethmoid sinus (AES), cells within the posterior ethmoid sinus (PES), and the ethmoid bulla (EB). In some instances, suprabullar cells of the ethmoid sinus (ES) drain into the ethmoid bulla (EB). Some suprabullar cells may drain directly into the retrobullar space (RBS). The ethmoid bulla (EB) may itself provide fluid communication with the nasal cavity via one or more ostia, such that the ethmoid bulla (EB) may provide a fluid communication path between the other ethmoid sinus (ES) cells (that drain into the ethmoid bulla (EB)) and the nasal cavity. For instance, the ethmoid bulla (EB) may provide fluid communication through an ostium at the retrobullar space (RBS). The fluid communication paths provided by ostia may allow the entry of air and liquids (e.g., medications); while also allowing drainage of mucus. In some instances, the ostia may become blocked, may become functionally closed due to mucosal thickening, or may otherwise not provide sufficient fluid communication. In addition or in the alternative, the configuration of the retrobullar space (RBS) may impede flow through the ostium of the ethmoid bulla (EB).

The anatomy of the ethmoid sinus (ES) may make it impractical to perform a dilation procedure on ostia of the ethmoid sinus (ES) using dilation catheter system (10) to improve fluid communication within the ethmoid sinus (ES). This may lead some operators to perform an ethmoidectomy, which is an invasive procedure that involves removal of ethmoid sinus (ES) portions (e.g., tissue and bone) using an instrument such as a debriding instrument. This kind of procedure may be somewhat crude an inelegant, resulting in removal of significant amounts of mucosa that might otherwise benefit the patient. Ethmoidectomy procedures may also have risks of inadvertent damage to optic nerves, damage to orbital muscles, damage to olfactory bulbs, damage to other anatomical structures, and even leakage of cerebrospinal fluid. Even in successful ethmoidectomies, the patient may need to return for several follow-up debridements. It may therefore be desirable to improve fluid communication from within the ethmoid sinus (ES) to the nasal cavity without resorting to a procedure like an ethmoidectomy. In some instances, this may involve implantation of a port in one or more cells of the ethmoid sinus (ES). Several merely illustrative examples of such ports are described in greater detail below, while other examples will be apparent to those of ordinary skill in the art in view of the teachings herein.

A. Exemplary Port with Single Wall Deployment

FIG. 7 shows an exemplary instrument (100) that may be used to deploy a port (200) in the ethmoid bulla (EB). Instrument (100) of this example has a piercing tip (102) and an opening (104) proximal to tip (102). In some versions, the outer diameter of instrument (100) is approximately 3 mm, though other dimensions may be used. The mouth of opening (104) lies along a plane that is oblique to the longitudinal axis of instrument (100) in the present example, though it should be understood that opening (100) may instead have other configurations and orientations. Instrument (100) may be introduced through the patient's nose (in this case, the patient's right nostril) and positioned at an anterior/inferior wall of the ethmoid bulla (EB). Instrument (100) may be positioned using visualization from endoscope (60) described above and/or from some other device. A retractable sheath (not shown) may be used to shield tip (102) until instrument (100) reaches the ethmoid bulla (EB).

Figure 7A:
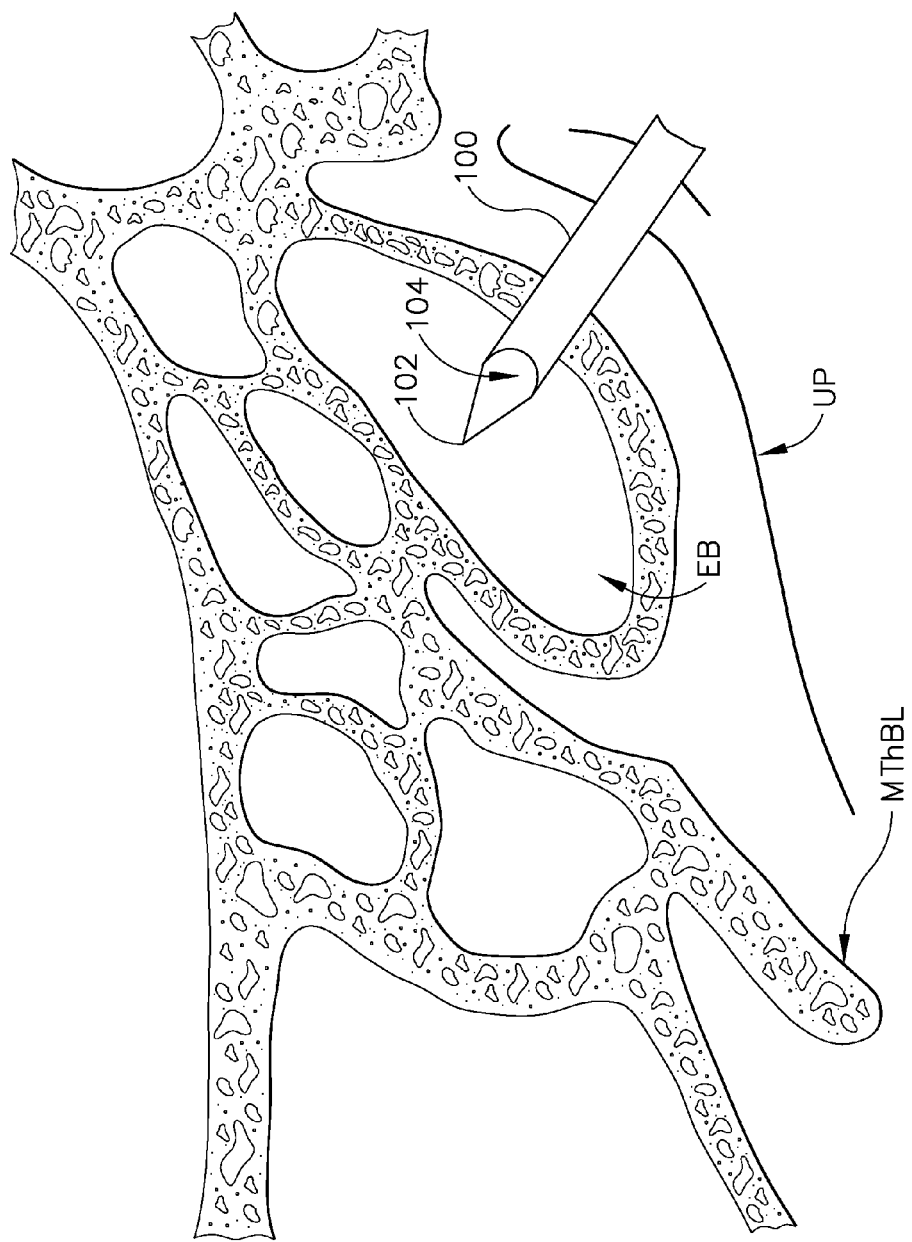
FIG. 7A depicts a left sagittal cross-sectional view of a portion of a human head, with an exemplary port deployment instrument piercing a wall of the ethmoid bulla.

Once positioned at the ethmoid bulla (EB), instrument (100) may be advanced against the ethmoid bulla (EB) such that tip (102) pierces the wall of the ethmoid bulla (EB), allowing opening (104) to be positioned within the ethmoid bulla (EB) as shown in FIG. 7A. Tip (102) is configured to pierce the wall of the ethmoid bulla (EB) without shattering the wall of the ethmoid bulla (EB). In other words, the wall of the ethmoid bulla (EB) remains intact except for the opening created by instrument (100), with such an opening being approximately the same size as the outer diameter of instrument (100). In some versions, tip (102) is rotated (e.g., by hand, using a torsion spring, etc.) to assist with piercing of the ethmoid bulla (EB). Such rotation may be in one angular direction or may be in opposing angular directions (e.g., in a rocking motion). In addition or in the alternative, tip (102) may be imparted with a reciprocating longitudinal motion. Tip (102) may also have an abrasive surface/edge and/or other features that promote piercing of the ethmoid bulla (EB). Various suitable configurations for tip (102) and methods for piercing the ethmoid bulla (EB) with tip (102) will be apparent to those of ordinary skill in the art in view of the teachings herein.

After instrument (100) has pierced the ethmoid bulla (EB), instrument (100) may deploy a port (200) within the opening created in the wall of the ethmoid bulla (EB) by tip (102), as shown in FIG. 7B. By way of example only, instrument (100) may include a translating push-rod or other feature within instrument (100) that is able to drive port (200) out through opening (104). As another merely illustrative example, instrument (100) may be configured and operable in accordance with at least some of the teachings of U.S. Pub. No. 2011/0015645, entitled "Tympanic Membrane Pressure Equalization Tube Delivery System," published Jan. 20, 2011, now U.S. Pat. No. 8,864,774, issued Oct. 21, 2014, the disclosure of which is incorporated by reference herein. In such versions, port (200) may be generally analogized to the pressure equalization tube deployed in a patient's tympanic membrane. Various other suitable ways in which port (200) may be deployed in the wall of the ethmoid bulla (EB) will be apparent to those of ordinary skill in the art in view of the teachings herein.

Port (200) of the present example comprises a cylindraceous body (202), a first flange (204) at one end of body (202), and a second flange (206) at the other end of body (202). Body (202) is hollow and defines a lumen (208) extending from flange (204) to flange (206). As shown in FIG. 7B, flange (204) is positioned within the interior of the ethmoid bulla (EB) while flange (206) is positioned at the exterior of the ethmoid bulla (EB). Flanges (204, 206) are configured to generally maintain the position of port (200) with respect to the ethmoid bulla (EB). Flanges (204, 206) may be separated from each other by any other suitable distance, such that body (202) may extend to any suitable length. In some versions, only one flange (204, 206) is provided. For instance, flange (206) may be omitted in some versions.

Port (200) may be formed of a resilient material, such that port (200) is compressed while port (200) is within instrument (100); with port (200) resiliently assuming the rivet like shape shown in FIG. 7B as soon as port (200) exits instrument (100). In some other versions, port (200) is formed of a malleable material. In some such versions, instrument (100) includes features that form the rivet like shape of port (200) as port (200) is deployed in the wall of ethmoid bulla (EB). It should also be understood that port (200) may be formed of a bioabsorbable or biodegradable material. In versions where port (200) is formed of a bioabsorbable material, the bioabsorbable material forming port (200) may include one or more therapeutic materials. In some versions where port (200) is formed of a non-bioabsorbable/non-biodegradable material, port (200) may eventually be removed from the patient some time after implantation. Port (200) may also be formed of a material that is configured to wick fluids. By way of example only, port (200) may be formed of semi-flexible, porous polyethylene, with a pore size selected to optimize wicking and with a surface coating/treatment to make port (200) hydrophilic. Various suitable materials that may be used to form port (200) will be apparent to those of ordinary skill in the art in view of the teachings herein.

It should be understood that, once port (200) has been deployed, lumen (208) enables the substantially free communication of air/mucus/etc. into and out of the ethmoid bulla (EB). Port (200) thus serves as a substitute or supplemental ostium for the ethmoid bulla (EB). In some instances, the patient may be instructed to periodically self-administer medications or other fluids within their nose after a port (200) has been implanted. By way of example only, such fluids/medications may include saline, a combination of saline and a surfactant, an anti-inflammatory (e.g., mometasone, etc.), an antibiotic, an anti-fungal, and/or various other kinds of fluids/medications, including combinations thereof. Lumen (208) may provide a substantially clear path for such fluids/medications to reach the mucosa within the ethmoid bulla (EB), in addition to providing a vent/drainage path for the ethmoid bulla (EB). In other words, the presence of port (200) may provide substantially greater communication of the administered fluids/medications to the ethmoid bulla (EB) than the communication that would be provided in the absence of port (200). In some variations, a sleeve (not shown) extends from flange (206) and is in fluid communication with lumen (208). Such a sleeve may be directly coupled with a fluid delivery device and/or a suction device to actively deliver fluid or suction to the ethmoid bulla (EB) via port (200). In addition or in the alternative, such a sleeve may provide a wicking function similar to the various wicks described in greater detail below.

Figure 8B:
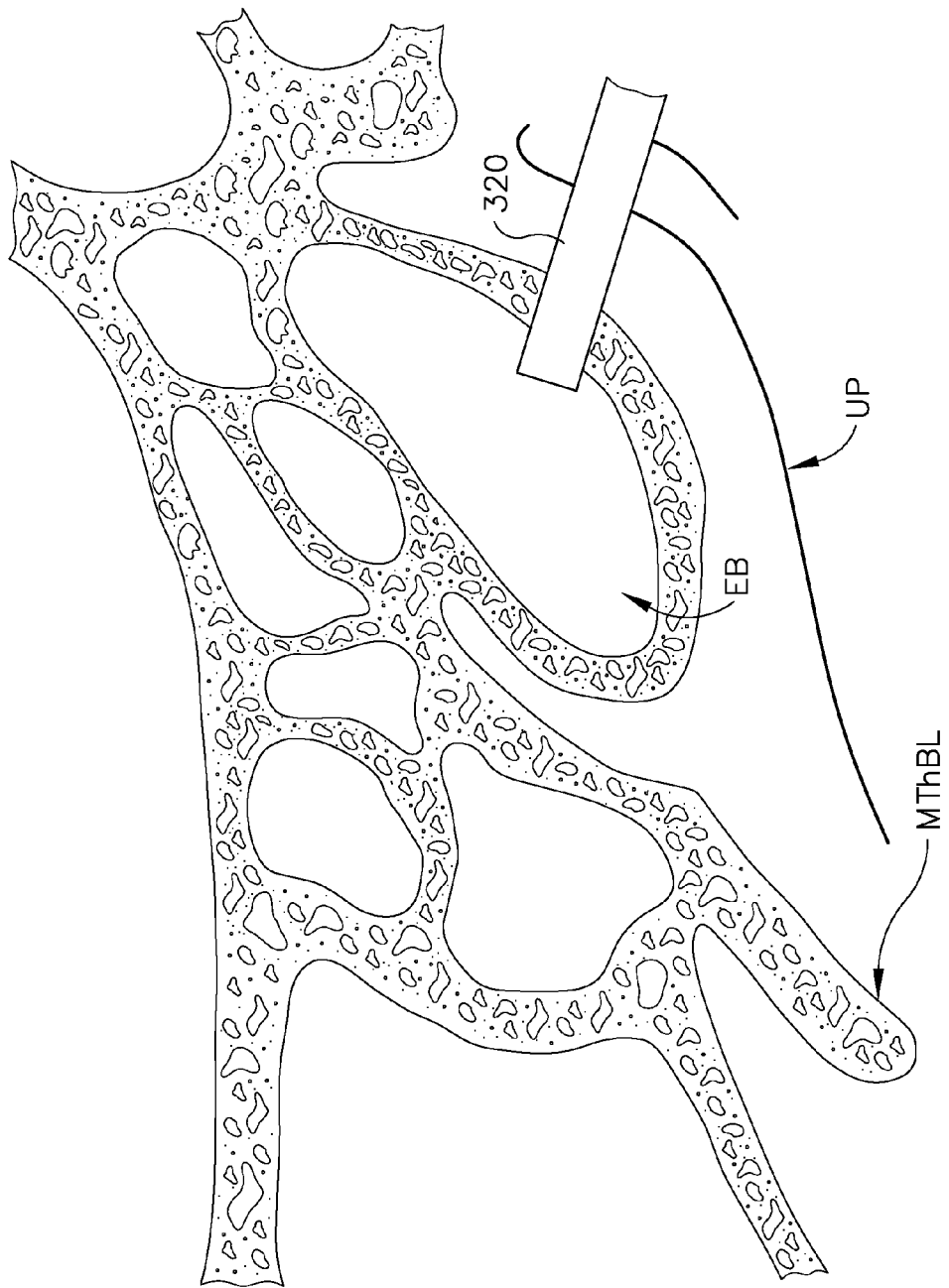
FIG. 8B depicts a left sagittal cross-sectional view of a portion of a human head, with a sheath of the instrument of FIG. 8A disposed in the pierced wall of the ethmoid bulla, and with a piercing obturator removed from the sheath.

FIGS. 8A-8D show another exemplary instrument (300) that may be used to deploy a port (200) in the ethmoid bulla (EB). Instrument (300) of this example comprises an outer cannula (320) and an obturator (310) slidably disposed within outer cannula (320). Obturator (310) has a sharp tip (312) configured to pierce the wall of the ethmoid bulla (EB), with cannula (320) trailing behind as shown in FIG. 8A. Tip (312) is configured to pierce the wall of the ethmoid bulla (EB) without shattering the wall of the ethmoid bulla (EB). In other words, the wall of the ethmoid bulla (EB) remains intact except for the opening created by tip (312), with that opening being approximately the same diameter as cannula (320). Obturator (310) may be coupled with a rotary drive, reciprocating drive, and/or any other suitable kind of drive that may assist in driving tip (312) through the wall of the ethmoid bulla (EB). Tip (312) may also have an abrasive surface/edge and/or other features that promote piercing of the ethmoid bulla (EB). By way of example only, tip (312) may be configured in accordance with any of the teachings herein relating to structures operable to pierce the wall of the ethmoid bulla (EB). Various suitable forms that tip (312) and associated drive features may take will be apparent to those of ordinary skill in the art in view of the teachings herein. It should also be understood that the wall of the ethmoid bulla (EB) may be reinforced with a backing, as taught elsewhere herein, to prevent the wall from shattering when encountered by tip (312). Furthermore, in some instances tip (312) may be passed through the wall of the ethmoid bulla (EB) so quickly that the inertia of the bone in the wall provides the effect of a backing support. Regardless of how tip (312) successfully passes through the wall of the ethmoid bulla (EB), once tip (312) and the distal end of cannula (320) are positioned within the ethmoid bulla (EB), obturator (310) may be withdrawn from cannula (320) as shown in FIG. 8B.

Figure 8C:
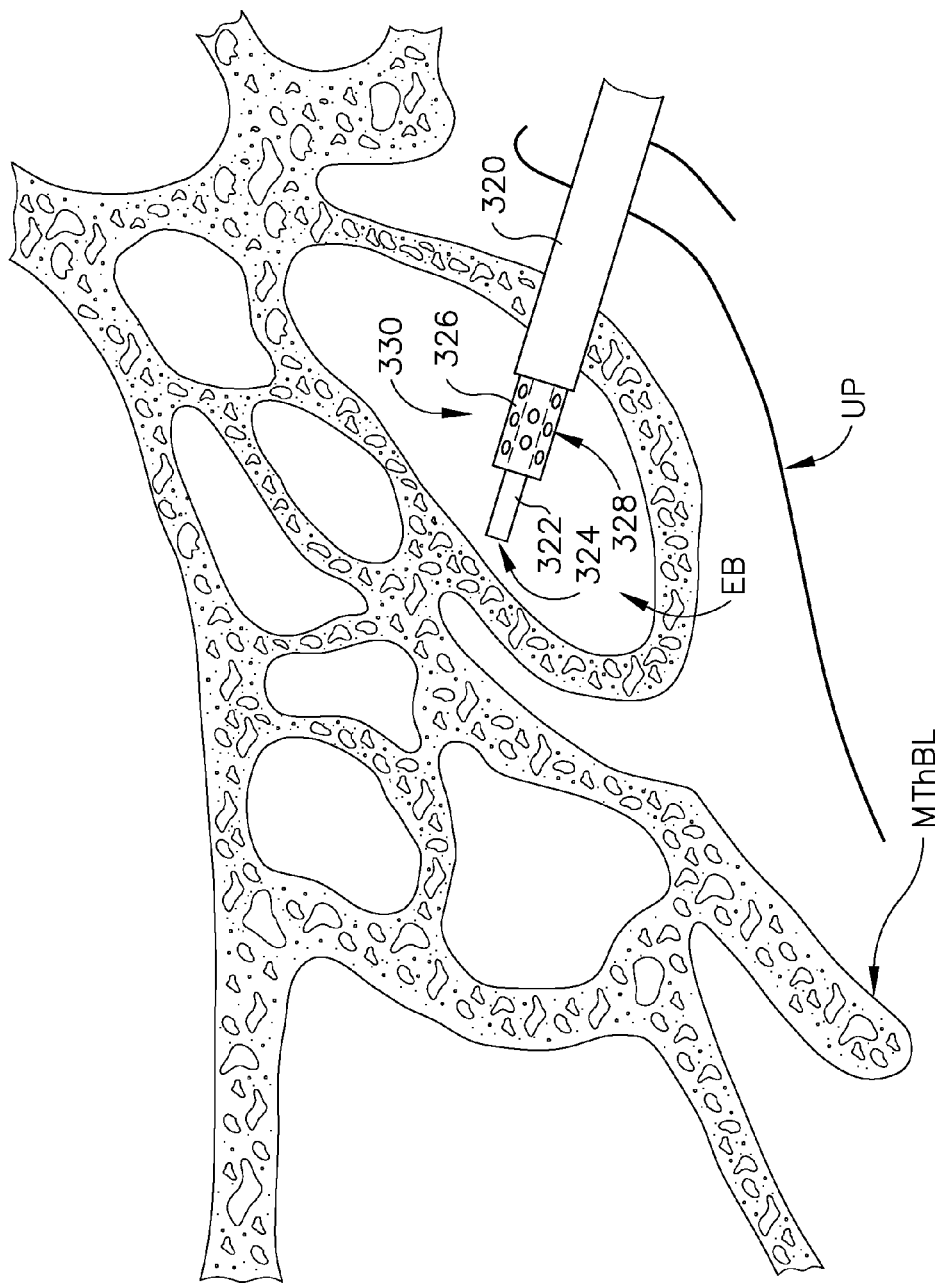
FIG. 8C depicts a left sagittal cross-sectional view of a portion of a human head, with a suction and irrigation device positioned in the ethmoid bulla via the sheath of FIG. 8B.

Next, the operator may advance a dual mode catheter (330) through cannula (320) into the ethmoid bulla (EB) as shown in FIG. 8C. Catheter (330) of this example includes a suction conduit (322) and an irrigation conduit (326). Suction conduit (322) is coaxially disposed within irrigation conduit (326). Suction conduit (324) is in fluid communication with a suction source (not shown) and has an open distal end (324), such that suction conduit (324) is operable to provide suction at distal end (324). Irrigation conduit (326) is in fluid communication with a fluid source (not shown) and has a plurality of transverse openings (328), such that irrigation conduit (326) is operable to communicate fluid (e.g. saline) through openings (328). Conduits (322, 326) may operate together within the ethmoid bulla (EB) to flush and draw out excess mucus/debris/etc. from within the ethmoid bulla (EB), thereby increasing the effective capacity of the ethmoid bulla (EB) and improving contact between the mucosa and subsequently administered medications.

After dual mode catheter (330) has been used to flush out the ethmoid bulla (EB), a port (200) may be deployed in the wall of the ethmoid bulla (EB) via cannula (320), as shown in FIG. 8D. Port (200) of this example is the same as port (200) shown in FIG. 7B and described above. Various suitable ways in which port (200) may be deployed via cannula (320) will be apparent to those of ordinary skill in the art in view of the teachings herein. In some other versions, cannula (320) is withdrawn from the ethmoid bulla (EB) and a separate instrument is used to deploy port (200) in the opening left by cannula (320). While instruments (100, 300) have been described above as being used to deploy port (200) in the wall of the ethmoid bulla (EB), it should be understood that the same instruments (100, 300) (or variations thereof) may be used to deploy various other devices in the wall of the ethmoid bulla (EB). By way of example only, such alternative devices may include wicks as described below, a combination of port and wick as described below, and/or various other devices. Furthermore, while port (200) is described herein as being deployed in the ethmoid bulla (EB), it should be understood that port (200) may be deployed in various other sinus cells.

B. Exemplary Port with Dual Wall Deployment

Figure 9A:
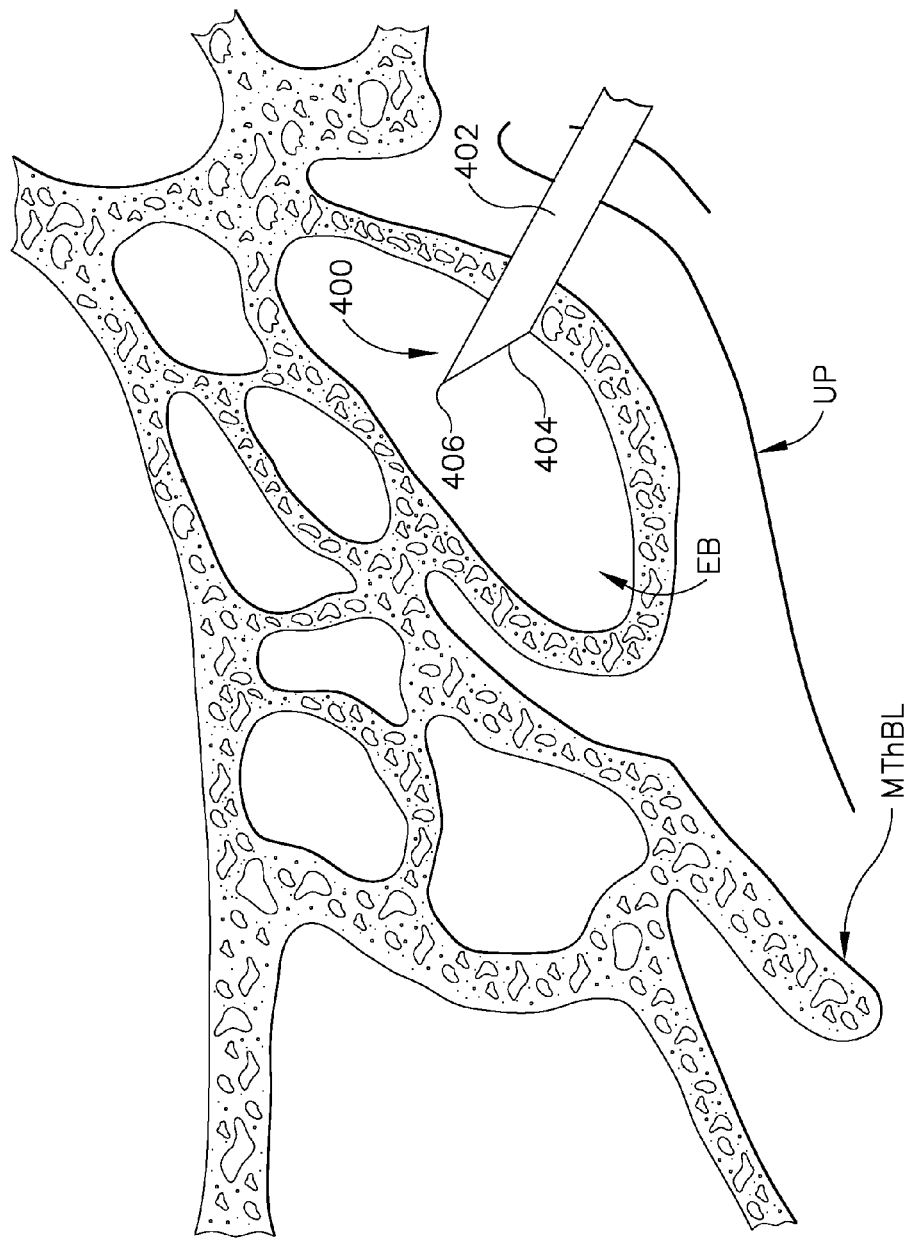
FIG. 9A depicts a left sagittal cross-sectional view of a portion of a human head, with another exemplary port deployment instrument piercing a wall of the ethmoid bulla.
Figure 9B:
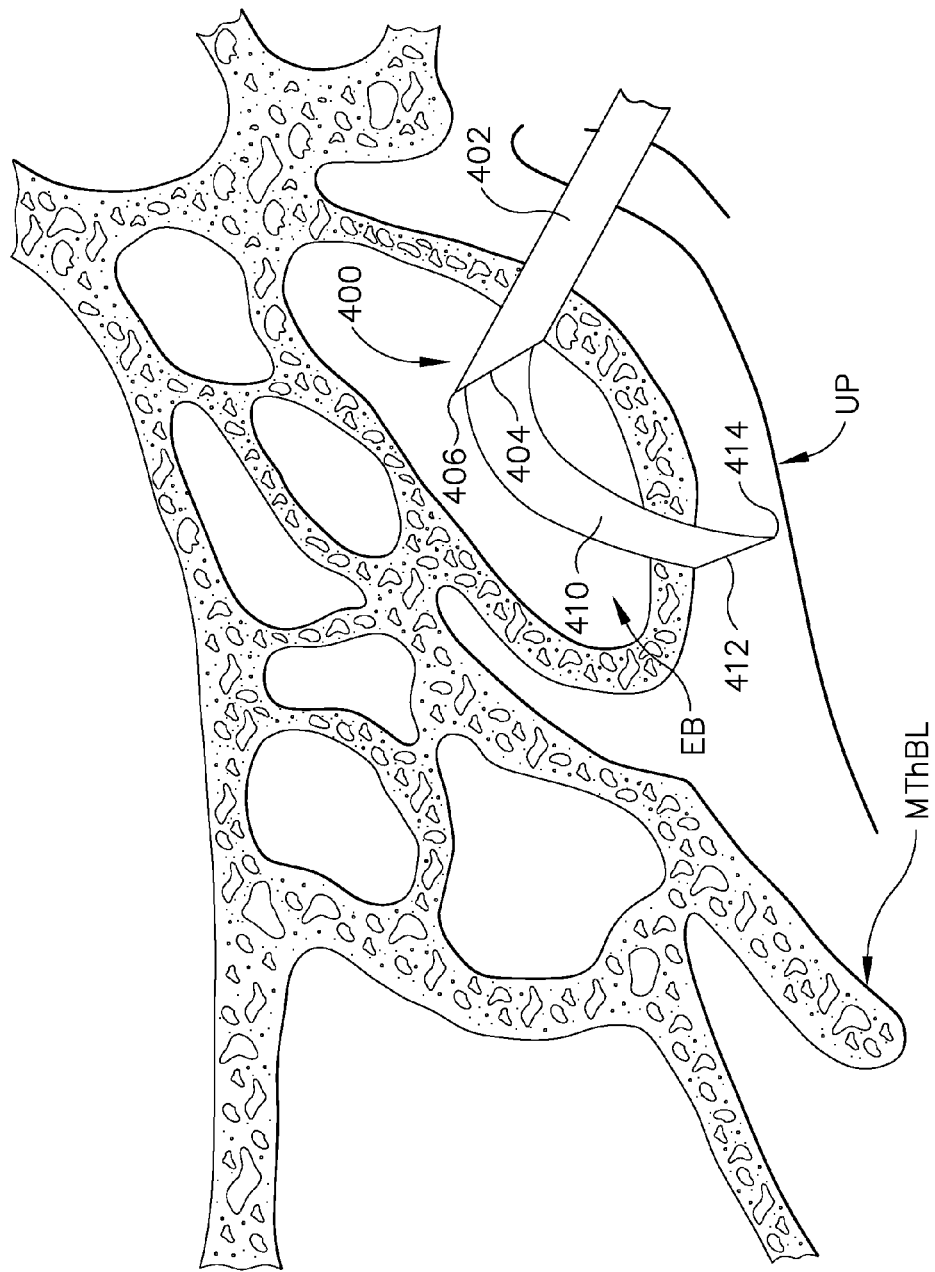
FIG. 9B depicts a left sagittal cross-sectional view of a portion of a human head, with a secondary piercing element extended from the instrument of FIG. 9A to pierce the wall of the ethmoid bulla in a second location.
Figure 9C:
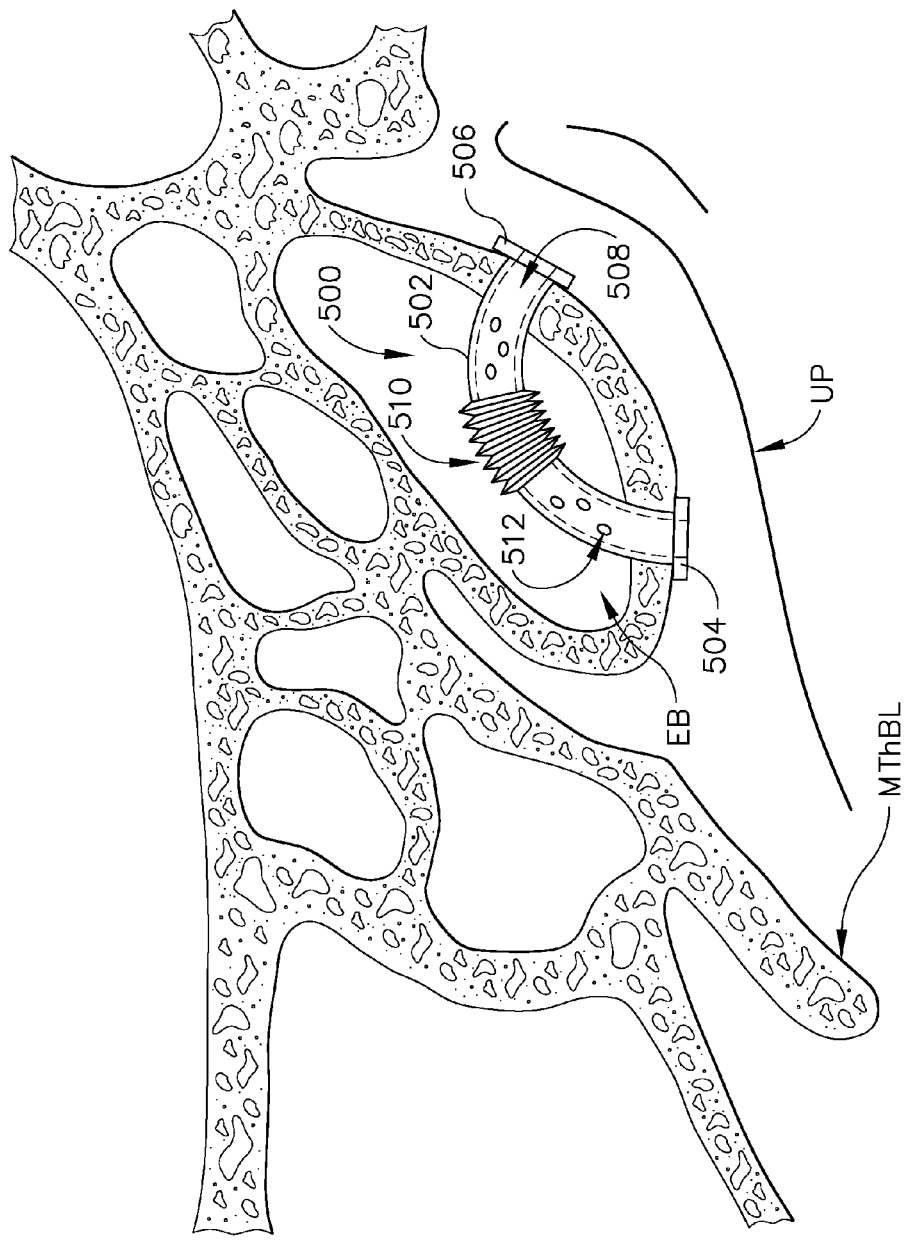
FIG. 9C depicts a left sagittal cross-sectional view of a portion of a human head, with a port disposed in both of the pierced walls of the ethmoid bulla.

In some instances, it may be desirable to provide more than one effective supplemental ostium in the ethmoid bulla (EB). Providing a plurality of effective supplemental ostia in the ethmoid bulla (EB) may further promote fluid communication into and out of the ethmoid bulla (EB). In some instances, this may be accomplished by deploying a plurality of ports (200) as described above in different locations in the ethmoid bulla (EB). Alternatively, a single port may provide a plurality of effective supplemental ostia in the ethmoid bulla (EB). FIGS. 9A-9C show one merely illustrative example of how an instrument (400) may be used to deploy a single port (500) that provides two effective supplemental ostia in the ethmoid bulla (EB). Instrument (400) of this example comprises a rigid first piercing member (402). Piercing member (402) includes a beveled, open distal end (404) that terminates in a sharp tip (406). This sharp tip (406) may be used to pierce the wall of the ethmoid bulla (EB) as shown in FIG. 9A. As noted above, a rotating and/or reciprocating motion may be imparted to tip (406) in various ways in order to assist tip (406) in piercing the wall of the ethmoid bulla (EB). Tip (406) may also have an abrasive surface/edge and/or other features that promote piercing of the ethmoid bulla (EB). Tip (406) is configured to pierce the wall of the ethmoid bulla (EB) without shattering the wall of the ethmoid bulla (EB). In other words, the wall of the ethmoid bulla (EB) remains intact except for the opening created by piercing member (402), with such an opening being approximately the same size as the outer diameter of piercing member (402).

Once distal end (404) has been positioned within the ethmoid bulla (EB), a second piercing member (410) is advanced distally out of distal end (404) as shown in FIG. 9B. Second piercing member (410) also has a beveled distal end (412) that terminates in a sharp tip (414). Sharp tip (414) is also configured to pierce the wall of the ethmoid bulla (EB). Tip (414) is configured to pierce the wall of the ethmoid bulla (EB) without shattering the wall of the ethmoid bulla (EB). In other words, the wall of the ethmoid bulla (EB) remains intact except for the opening created by second piercing member (410), with such an opening being approximately the same size as the outer diameter of second piercing member (410). Second piercing member (410) is formed of a resilient material such that second piercing member (410) is resiliently biased to assume the curved configuration shown in FIG. 9B. However, second piercing member (410) is configured to substantially straighten while fully disposed within first piercing member (402). By way of example only, second piercing member (410) may comprise nitinol. Various other suitable materials and configurations that may be used to form second piercing member (410) will be apparent to those of ordinary skill in the art in view of the teachings herein. Similarly, various suitable ways in which second piercing member (410) may be driven relative to first piercing member (402) will be apparent to those of ordinary skill in the art in view of the teachings herein. As shown in FIG. 9B, second piercing member (410) pierces the wall of ethmoid bulla (EB) when second piercing member (410) is advanced distally, due to the curved configuration of second piercing member. It should therefore be understood that first and second piercing members (402, 410) together form two separate openings in the wall of the ethmoid bulla (EB).

After second piercing member (412) has been actuated to form the second opening in the wall of the ethmoid bulla (EB), instrument (400) deploys a port (500) in the ethmoid bulla (EB), as shown in FIG. 9C. In some versions, port (500) is deployed along the exterior of second piercing member (412). Various suitable ways in which port (500) may be deployed will be apparent to those of ordinary skill in the art in view of the teachings herein. Port (500) of this example comprises a body (502) that extends between a first flange (504) and second flange (506). Flanges (504, 506) are both positioned at the exterior of the ethmoid bulla (EB) when port (500) is deployed. Body (502) is hollow and defines a lumen (508) extending from flange (504) to flange (506). Body (502) also defines a plurality of transverse openings (512) that are in fluid communication with lumen (508). Thus, fluid (e.g., air, mucus, medication, etc.) may flow through lumen (508) and openings (512), into and out of the ethmoid bulla (EB), via the effective supplemental ostia created at each flange (504, 506) of port (500).

Port (500) of this example also includes a corrugated region (510) that serves as a length absorbing feature. In particular, corrugated region (510) is resiliently biased to assume a compressed configuration, at which port (500) has a minimum length. However, corrugated region (510) is expandable to increase the effective length of port (500). In addition to providing a variable length for port (500), corrugated region (510) allows port (500) to flex such that flanges (504, 506) may be positioned at various orientations relative to each other. Thus, port (500) may be readily installed in various positions and configurations without requiring a particular predetermined distance between flanges (504, 506) or orientation of flanges (504, 506). It should be understood that port (500) may be formed of any of the various kinds of materials described above in relation to port (200).

C. Exemplary Alternative Port Configurations

Figure 10:
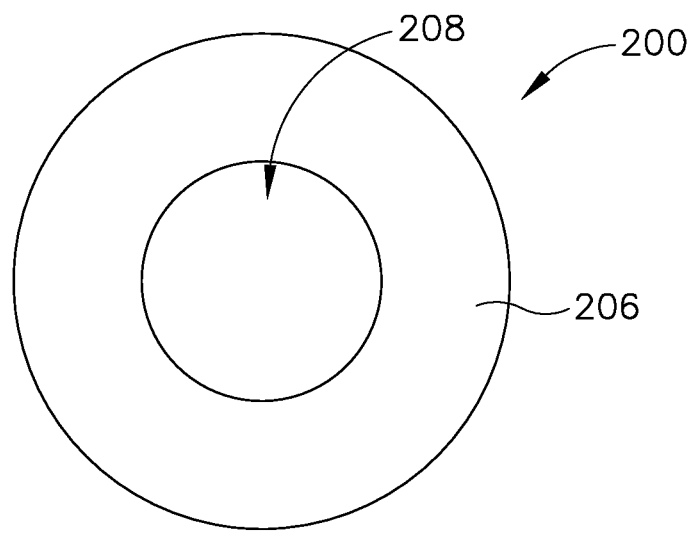
FIG. 10 depicts a top plan view of an exemplary port suitable for installation in a wall of an ethmoid bulla.
Figure 11:
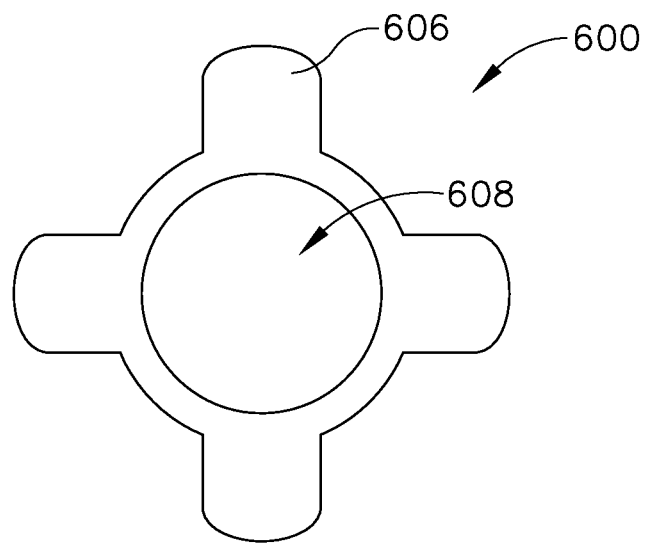
FIG. 11 depicts a top plan view of another exemplary port suitable for installation in a wall of an ethmoid bulla.
Figure 12:
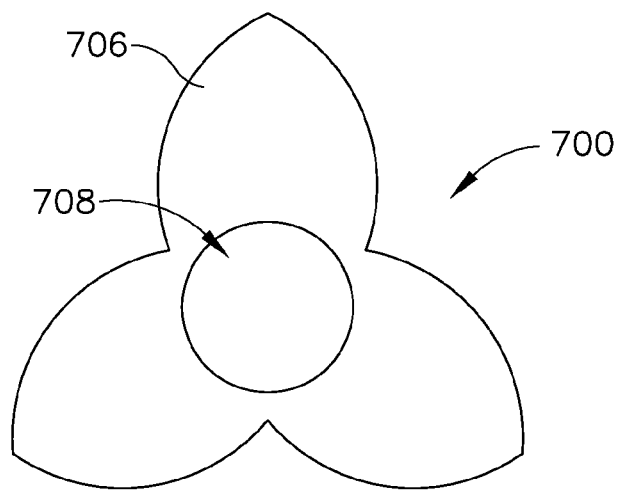
FIG. 12 depicts a top plan view of another exemplary port suitable for installation in a wall of an ethmoid bulla.

As shown in FIG. 10, flange (206) of port (200) described above has a circular shape. Flange (204) of port (200) may also have a circular shape. Alternatively, a variety of other shapes may be used. For instance, FIG. 11 shows an exemplary alternative port (600) that may be used as a substitute for port (200). Port (600) of this example that has a plurality of rounded wings or petals (606) extending outwardly relative to a lumen (608). This array of petals (606) may serve as a functional equivalent of flange (206), substantially maintaining the position of port (600) with respect to the ethmoid bulla (EB). FIG. 12 shows another exemplary alternative port (700) that may be used as a substitute for port (200). Port (700) of this example has a plurality of pointed petals (706) extending outwardly relative to a lumen (708). Again, petals (706) may serve as a functional equivalent of flange (206), substantially maintaining the position of port (700) with respect to the ethmoid bulla (EB). Other suitable variations of flanges (204, 206) and petals (606, 706) will be apparent to those of ordinary skill in the art in view of the teachings herein.

It should also be understood that flanges (204, 206) and petals (606, 706) may be deformable, such that port (200, 600, 700) may compress into a substantially cylindraceous shape before port (200, 600, 700) is deployed in the ethmoid bulla (EB). Furthermore, some versions of port (200, 600, 700) may have flange (204, 206) or petals (606, 706) only at one end of the body of port (200, 600, 700), such that the other end of port (200, 600, 700) is substantially straight without an outwardly protruding feature.

Figure 13:
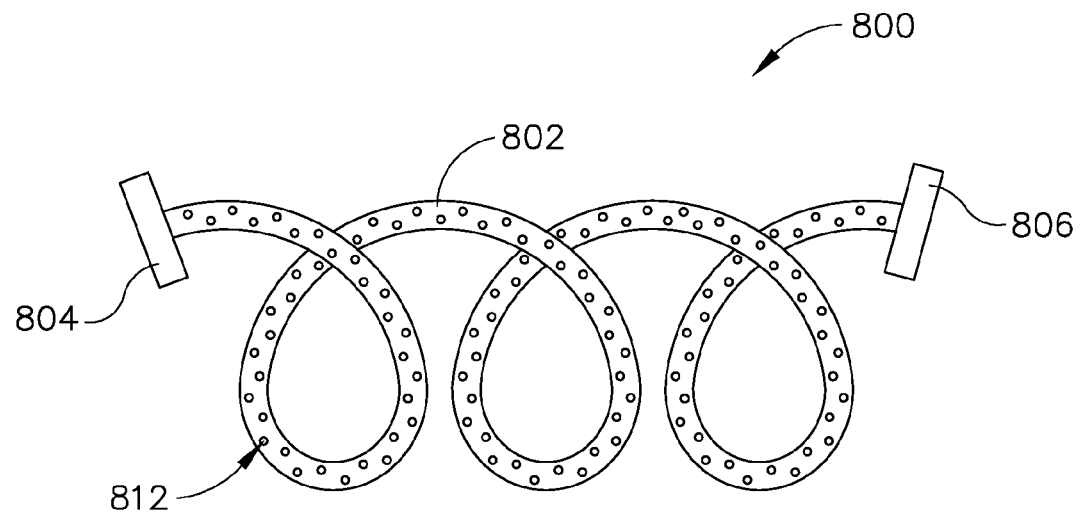
FIG. 13 depicts a side elevational view of another exemplary port suitable for installation in a wall of an ethmoid bulla.

FIG. 13 shows an exemplary port (800) that may be used as a substitute for port (500) described above. Port (800) of this example comprises a body (802) with a pair of flanges (804, 806). Body (802) defines a lumen (not shown) extending from flange (804) to flange (806). Body (802) also defines a plurality of transverse openings (812), similar to transverse openings (512) described above, that are in fluid communication with the lumen of body (802). Body (802) also has a corkscrew configuration in this example and is formed of a resilient material. In particular, body (802) is resiliently biased to form a compressed corkscrew configuration; yet may be expanded to increase the effective length of port (800). The corkscrew configuration thus serves as a length absorbing feature similar to corrugated region (510) of port (500). This facilitates deployment of port (800) installed in various positions and configurations without requiring a particular predetermined distance between flanges (804, 806). The corksrcrew configuration also enables port (800) to be installed with flanges (804, 806) at various orientations relative to each other.

It should be understood that ports (600, 700, 800) may be formed of any of the various kinds of materials described above in relation to port (200). Various other suitable forms that an ethmoid port may take will be apparent to those of ordinary skill in the art in view of the teachings herein. Furthermore, while the foregoing examples are provided in the context of providing a port in the ethmoid bulla (EB), it should be understood that ports may be installed elsewhere within the sinus complex, such as in the sphenoid sinus (SS), in the posterior ethmoid sinus (PES), and/or elsewhere, without necessarily also being installed in the ethmoid bulla (EB). By way of example only, an instrument may be used to form an opening in the middle turbinate vertical basal lamella (MTvBL), medial to the posterior wall of the ethmoid bulla (EB) but lateral to the lateral wall of the vertical basal lamella (MTvBL). A port may then be deployed in that formed opening. In some instances, the port may enter the superior meatus, medial to the posterior ethmoid sinus (PES) cells. In some other instances, the port may enter the anterior-most cell of the posterior ethmoid sinus (PES). In either case, the port may serve to increase ventilation to the posterior ethmoid sinus (PES) cells and allow patient-administered substances to reach the posterior ethmoid sinus (PES) cells. Various other ways in which the above described procedures (and in some cases, instruments) may be modified to provide ports in sinus cells other than the ethmoid bulla (EB) will be apparent to those of ordinary skill in the art in view of the teachings herein.

IV. Exemplary Wick for Ethmoid Sinus

In addition to or as an alternative to deploying a port in the ethmoid bulla (EB), it may be desirable to deploy a wick in the ethmoid bulla (EB) and/or in other sinus cavities. A wick may promote communication of medical fluids to the mucosa of the ethmoid bulla (EB) through a capillary action. This capillary action may be enhanced by maximizing contact between the wick material and the mucosa in the ethmoid bulla (EB). The wick may be bioabsorbable and may itself be formed in part by a therapeutic material. Various examples of intrasinus and intersinus wicks will be described in greater detail below, while other examples will be apparent to those of ordinary skill in the art in view of the teachings herein.

Figure 14:
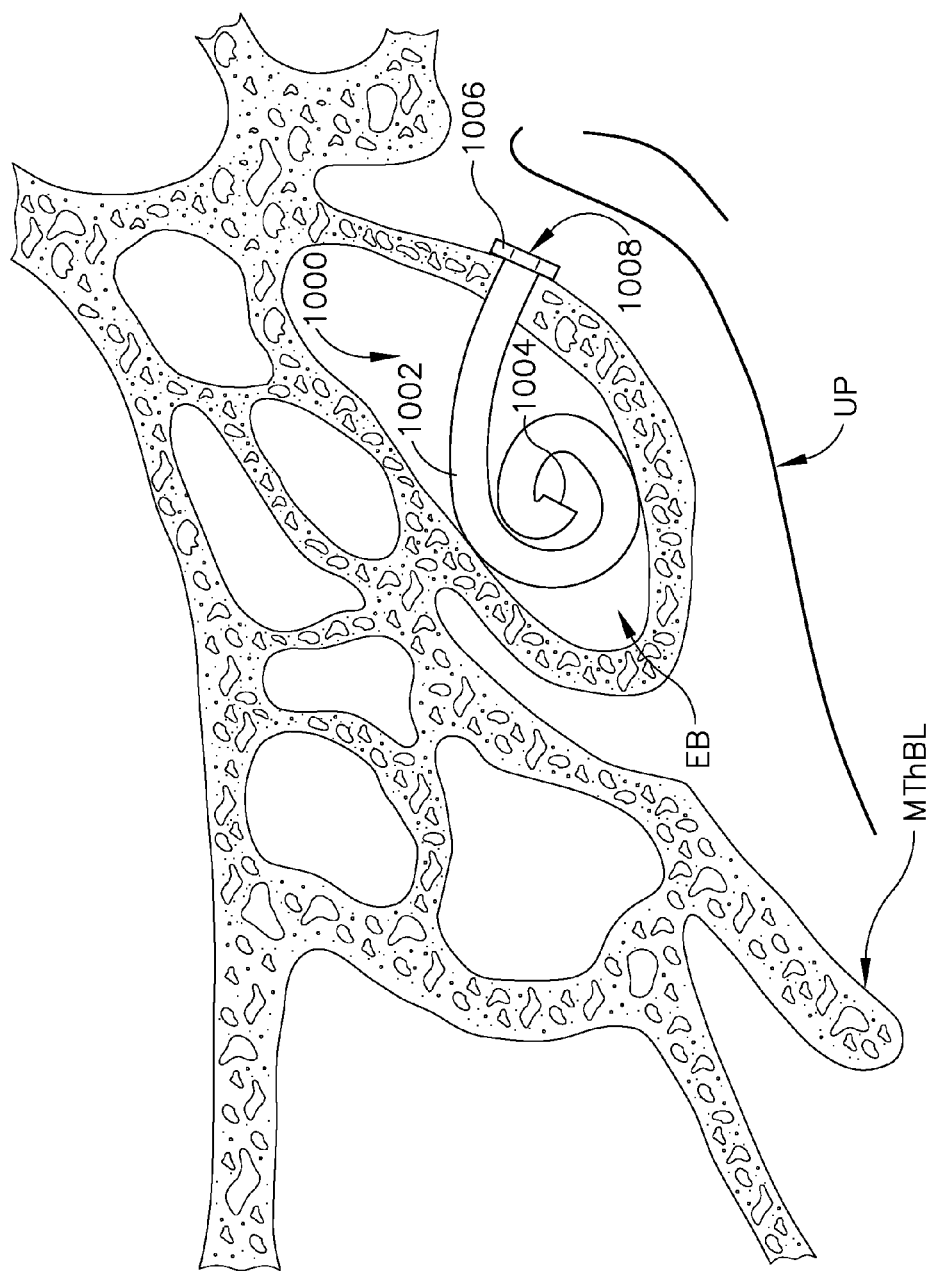
FIG. 14 depicts a left sagittal cross-sectional view of a portion of a human head, with an exemplary wick installed in the ethmoid bulla.

FIG. 14 shows one merely exemplary wick (1000) deployed in the ethmoid bulla (EB). By way of example only, an instrument similar to instrument (100) or instrument (400) may be used to deploy wick (1000). Wick (1000) of this example comprises a body (1002) having a free end (1004) and a flange (1006). The material forming body (1002) is selected to optimize the capillary action provided through body (1002). Various suitable materials that may be used to form body (1002) will be apparent to those of ordinary skill in the art in view of the teachings herein. Body (1002) is shown as being coiled within the ethmoid bulla (EB), and it should be understood that body (1002) is in contact with the mucosa of the ethmoid bulla (EB).

Flange (1006) is configured to generally secure one end of wick (1000) relative to the wall of the ethmoid bulla (EB). It should be understood that flange (1006) may be configured similar to flange (206), similar to petals (606, 706), or in any other suitable fashion. It should also be understood that flange (1006) may simply be omitted in some versions. Flange (1006) of the present example defines an opening (1008) permitting communication of fluid through flange (1006) to reach body (1002). For instance, if a patient self-administers a fluid medication into their nose while wick (1000) is deployed in the patient's ethmoid bulla (EB), that medication may wick through body (1002) to the mucosa of the ethmoid bulla (EB). Wick (1000) thus provides a path for the medication that the medication would have otherwise not had, in order to reach the mucosa of the ethmoid bulla (EB).

Figure 15:
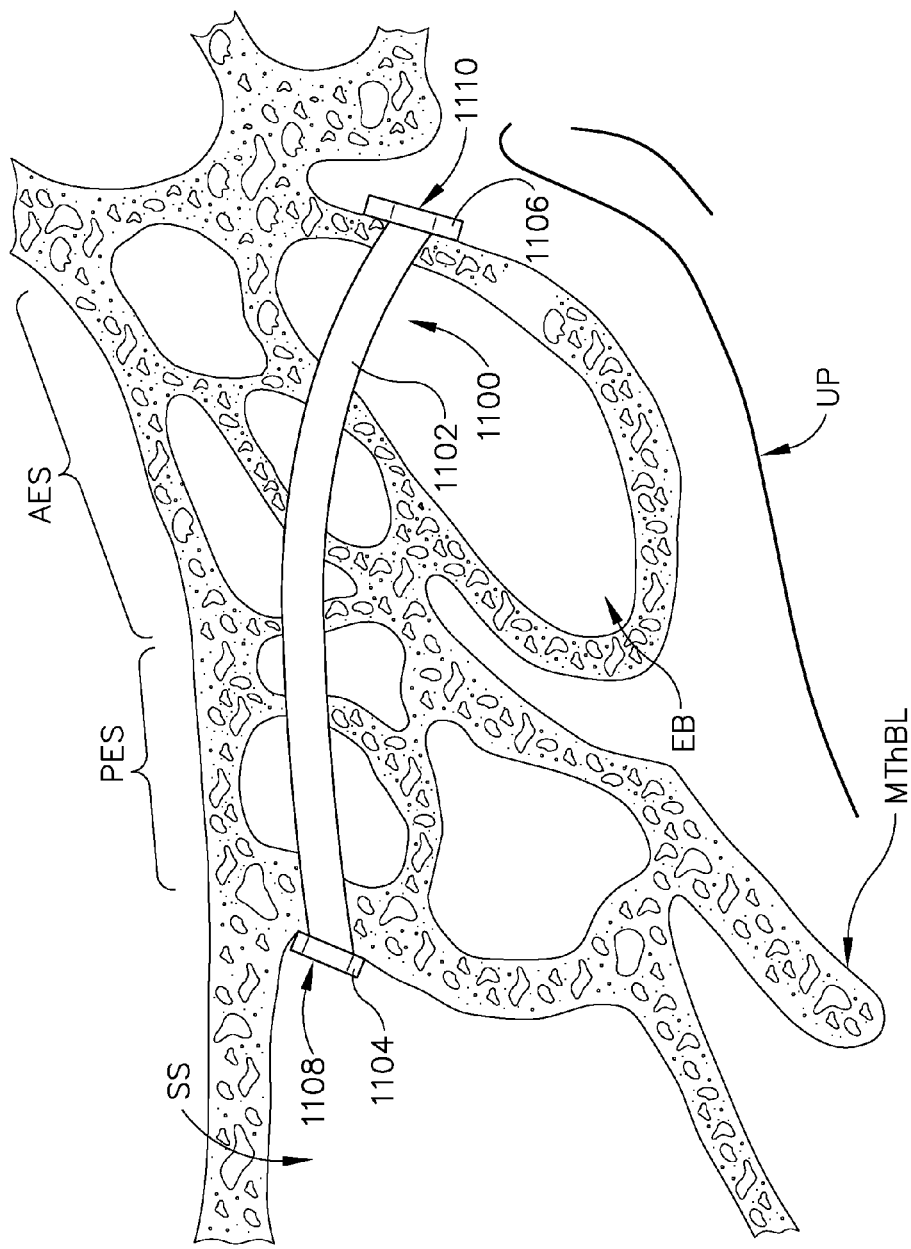
FIG. 15 depicts a left sagittal cross-sectional view of a portion of a human head, with an exemplary wick installed across a series of ethmoid sinus cells.

If desired, a wick may span across more than one sinus cell. For instance, FIG. 15 shows a wick (1100) extending along several sinus cells. In particular, wick (1100) traverses the ethmoid bulla (EB), traverses two anterior ethmoid sinus (AES) cells, traverses two posterior ethmoid sinus (PES) cells, and terminates at the sphenoid sinus (SS). Wick (1100) of this example comprises a body (1102) having a first flange (1104) at one end and a second flange (1106) at the other end. The material forming body (1102) is selected to optimize the capillary action provided through body (1102). Various suitable materials that may be used to form body (1102) will be apparent to those of ordinary skill in the art in view of the teachings herein. When installed as shown, body (1102) contacts mucosa in the ethmoid bulla (EB), the anterior ethmoid sinus (AES) cells, and the posterior ethmoid sinus (PES) cells. While body (1102) is shown as having a substantially straight configuration while spanning across the ethmoid bulla (EB), the anterior ethmoid sinus (AES) cells, and the posterior ethmoid sinus (PES) cells, it should be understood that body (1102) may be more loosely positioned in these cells such that there is substantial contact between body (1102) and the mucosa in these cells.

Flange (1106) generally secures one end of body (1102) at an exterior wall of the ethmoid bulla (EB) while flange (1104) generally secures the other end of body (1102) at an interior wall of the sphenoid sinus (SS). Flanges (1104, 1106) may each be configured similar to flange (206), similar to petals (606, 706), or in any other suitable fashion. It should also be understood that one or both of flanges (1104, 1106) may simply be omitted in some versions. Each flange (1104, 1106) of the present example defines a respective opening (1108, 1110) permitting communication of fluid through flange (1104, 1106) to reach body (1102). For instance, if a patient self-administers a fluid medication into their nose while wick (1100) is deployed, that medication may wick through body (1102) to the mucosa of the ethmoid bulla (EB), the mucosa of the anterior ethmoid sinus (AES) cells, and the mucosa of the posterior ethmoid sinus (PES) cells; and may further reach the sphenoid sinus (SS). Wick (1100) thus provides a path for the medication that the medication would not have otherwise had, in order to reach the mucosa of the ethmoid bulla (EB), the mucosa of the anterior ethmoid sinus (AES) cells, and the mucosa of the posterior ethmoid sinus (PES) cells.

It should also be understood that wick (1100) may be installed in numerous other configurations. For instance, wick (1100) need not reach all the way to the sphenoid sinus (SS), and may instead terminate in any other sinus cell (e.g., within one of the anterior ethmoid sinus (AES) cells or one of the posterior ethmoid sinus (PES) cells, etc.). Various suitable paths for wick (1100) will be apparent for those of ordinary skill in the art in view of the teachings herein. It should also be understood that various instruments may be used to deploy wick (1100). By way of example only, an instrument similar to instrument (100) or instrument (400) may be used to deploy wick (1100). Other suitable instruments that may be used to deploy wick (1100) will be apparent to those of ordinary skill in the art in view of the teachings herein.

Figure 16A:
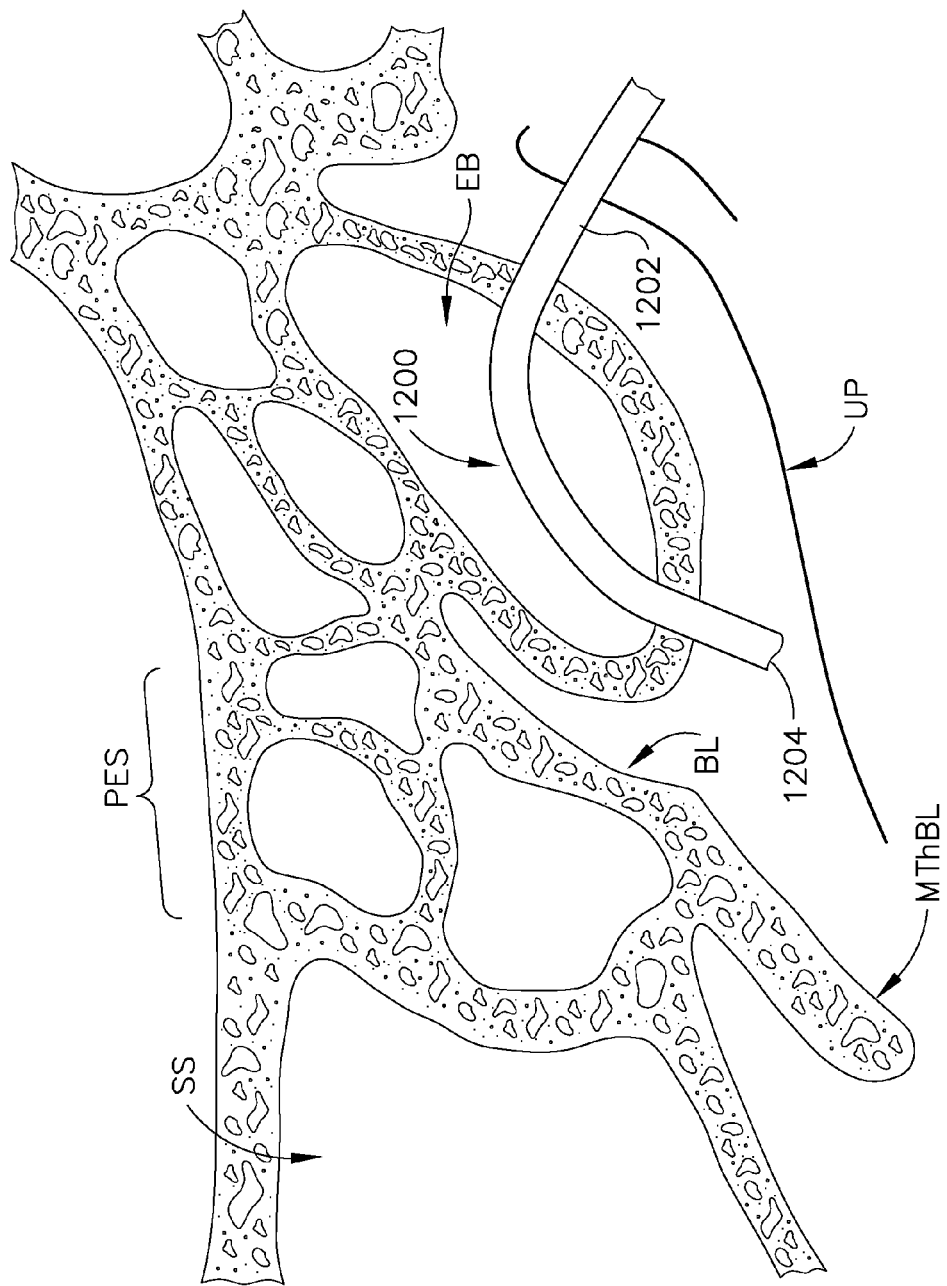
FIG. 16A depicts a left sagittal cross-sectional view of a portion of a human head, with an exemplary wick passed through the ethmoid bulla in a first stage of installation.
Figure 16B:
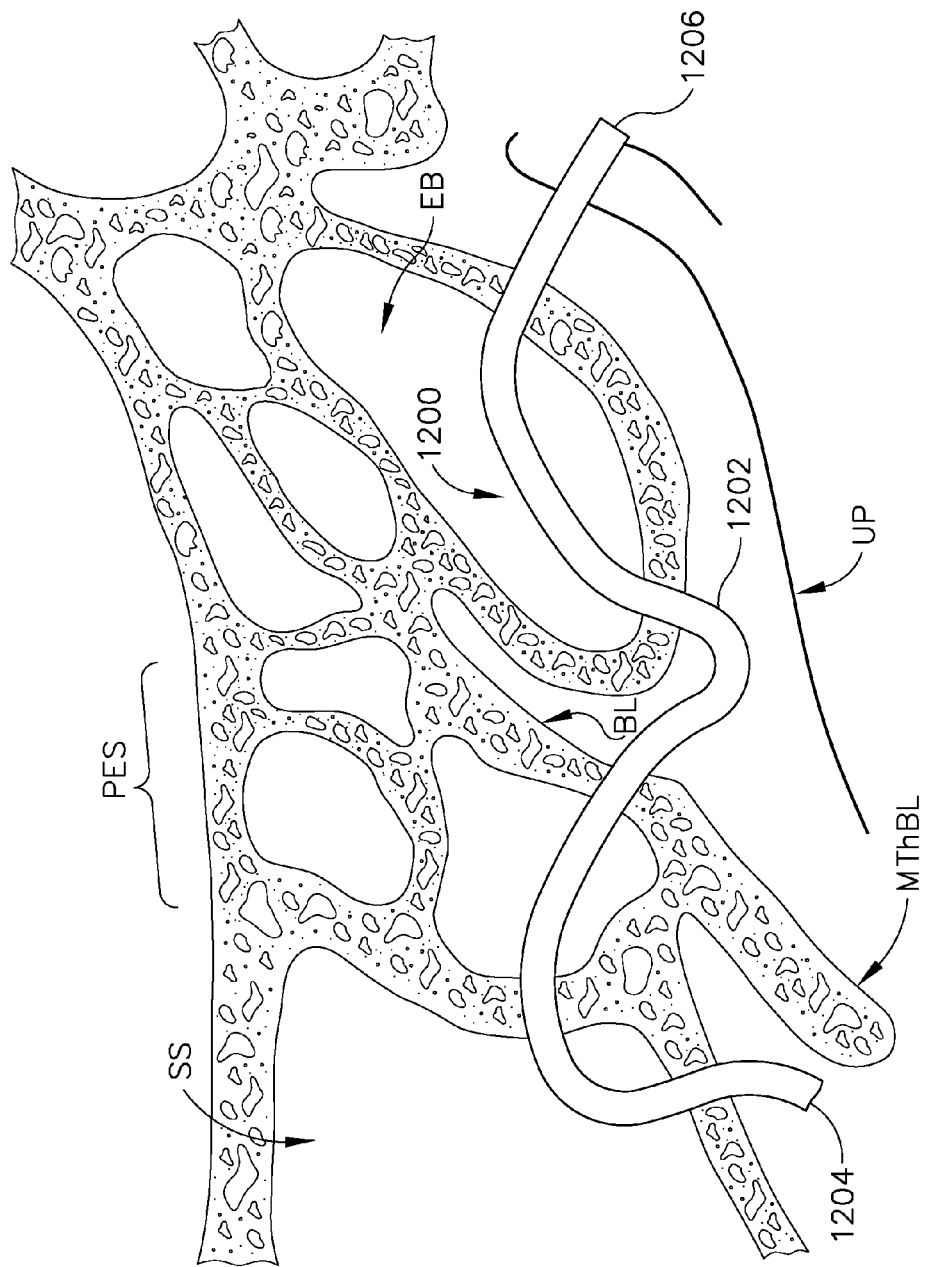
FIG. 16B depicts a left sagittal cross-sectional view of a portion of a human head, with the wick of FIG. 16A passed through an additional ethmoid sinus cell and the sphenoid sinus in a second stage of installation.

In some instances, a curved needle may be used to deploy a wick. For instance, FIG. 16A shows an example of a wick (1200) that has been driven through the ethmoid bulla (EB) with one pass of a curved needle (not shown). Wick (1200) of this example has a body (1202), a first free end (1204), and a second free end (1206). Body (1202) may be configured similar to bodies (1002, 1102) described above. The arc of the curved needle enables the needle to pierce and pass through the wall of the ethmoid bulla (EB) twice in a single pass, such that wick (1200) enters and exits the ethmoid bulla (EB). In a second pass, the curved needle pierces the middle turbinate vertical basal lamella (MTvBL) to pass through a posterior ethmoid sinus (PES) cell and then through the sphenoid sinus (SS) as shown in FIG. 16B. Thus, first free end (1204) is positioned inferior to the sphenoid sinus (SS), while second free end (1206) is positioned anterior to the ethmoid bulla (EB). Ends (1204, 1206) lack flanges, petals, or similar structures in this example. Body (1202) contacts mucosa in the ethmoid bulla (EB), the posterior ethmoid sinus (PES) cell, and the sphenoid sinus (SS), such that body (1202) is able to deliver medical fluid to these sinus cells through a capillary action. Of course, a curved needle or other device may be used to route a wick (1200) in various other routes using any desired number of passes of the needle.

Figure 17:
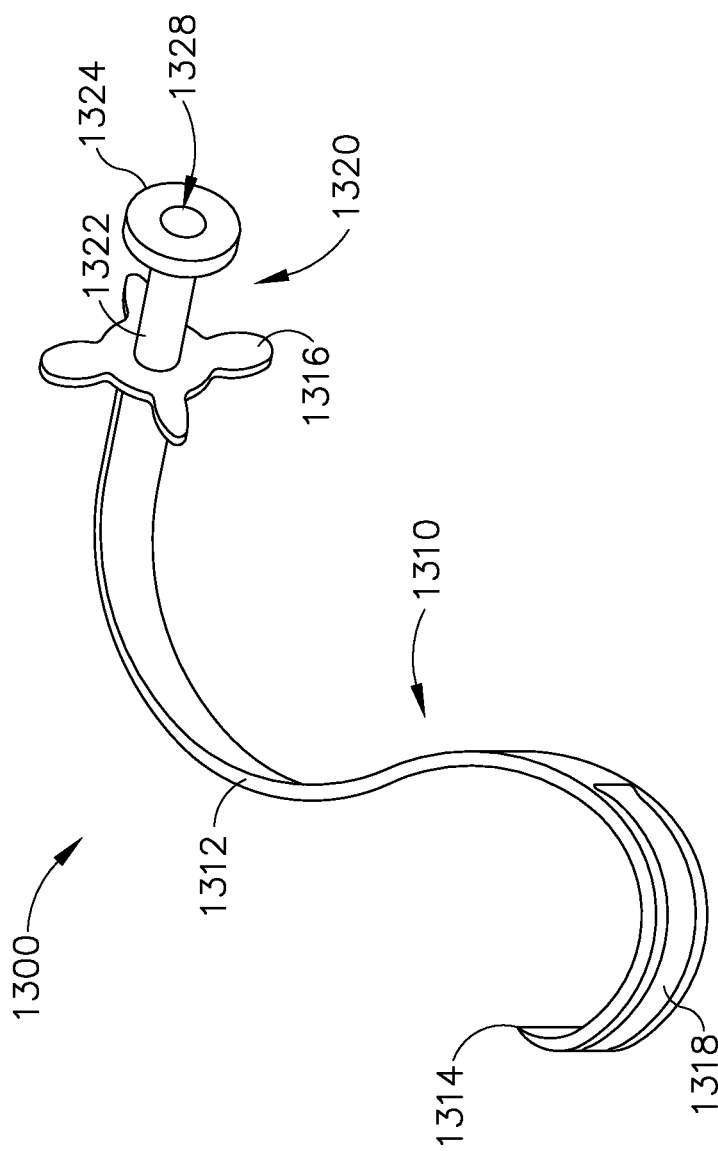
FIG. 17 depicts a perspective view of an exemplary ethmoid port with a wick having a clamping feature.

FIG. 17 depicts an example of a wicking port (1300) that is essentially a hybrid of the ports and wicks described above. Wicking port (1300) of this example includes a wick portion (1310) and a port portion (1320). As described in greater detail below, wick portion (1310) will be positioned anteriorly relative to port portion (1320) when wicking port (1300) is deployed in a patient. Wicking port (1300) is positioned in the particular orientation shown in FIG. 17 merely to illustrate the structural features of wicking port (1300), not to represent a deployed orientation. Wick portion (1310) includes a generally flat wick body (1312) that terminates in a free end (1314), with a set of wings (1316) at the other end. Body (1312) may be configured similar to bodies (1002, 1102) described above. A resilient band (1318) is integrated into wick body (1312), just proximal to free end (1314). Band (1318) is resiliently biased to assume a bent clamping configuration as described below; yet band (1318) is sufficiently compliant to flex into a substantially straight configuration. Port portion (1320) includes a cylindraceous body (1322), a flange (1324), and a lumen (1328). Port portion (1320) is substantially similar to port (200) described above, except that body (1322) is joined to wick portion (1310) where body (202) has flange (206). Lumen (1328) is in fluid communication with body (1312), such that fluid communicated through lumen (1328) may be wicked through body (1312); and such that fluid wicked through body (1312) may be communicated through lumen (1328). In some alternative versions, flange (1324) is omitted.

Figure 18:
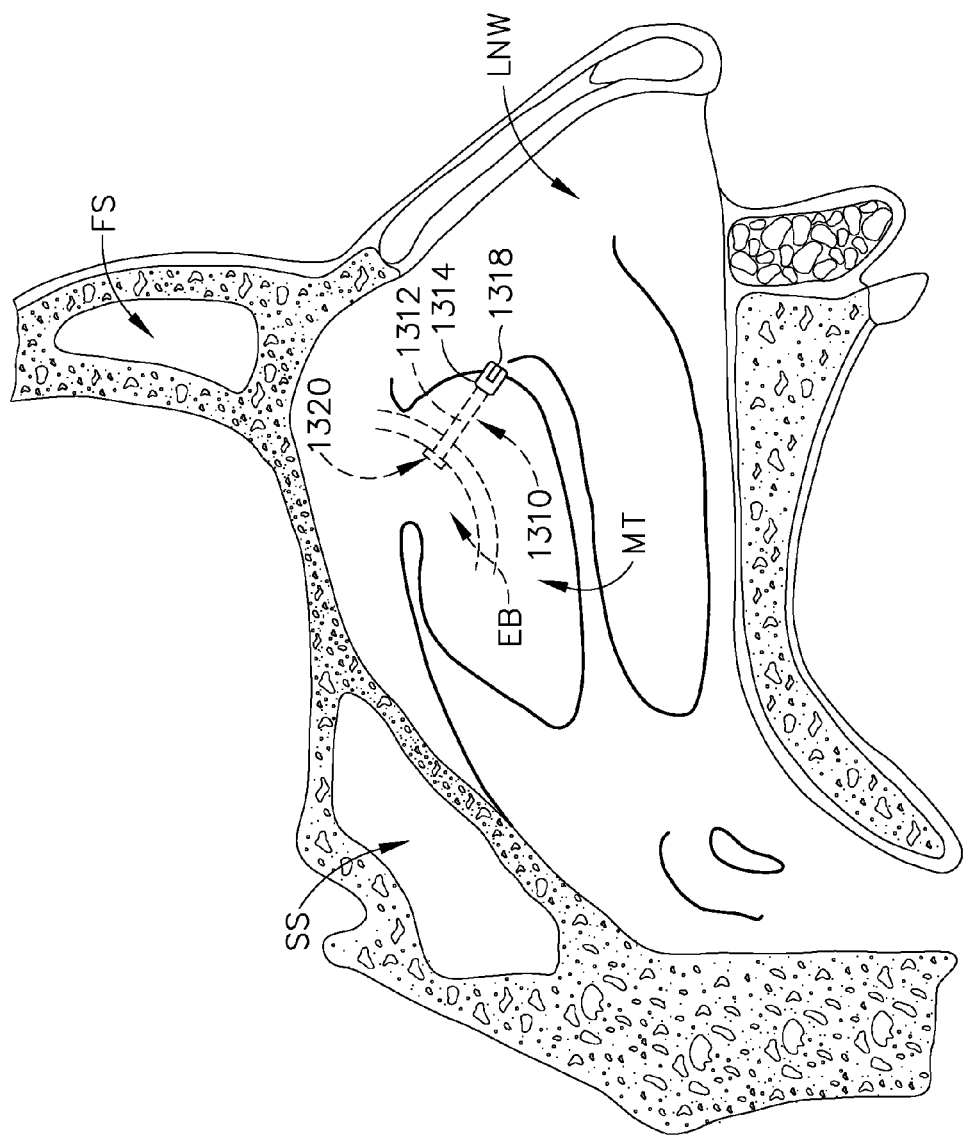
FIG. 18 depicts a left sagittal cross-sectional view of a portion of a human head, along a plane medial to the plane associated with the view of FIG. 6, with the port of FIG. 17 installed in the ethmoid bulla and with the clamping feature engaged with the middle turbinate.

FIG. 18 shows an exemplary deployment of wicking port (1300). As shown, port (1300) is positioned such that port portion (1320) is disposed through the wall of the ethmoid bulla (EB). Wings (1316) and flange (1324) cooperate to maintain the position of port portion (1320) relative to the ethmoid bulla (EB). Body (1312) spans across a portion of the nasal cavity to reach the middle turbinate (MT). Body (1312) wraps around an anterior ridge of the middle turbinate (MT) and band (1318) acts as a clip resiliently securing body (1312) to the middle turbinate (MT). Free end (1314) of body (1312) is positioned at the medial side of the middle turbinate (MT). The positioning of body (1312) may substantially increase its saturation with fluids administered through the patient's nose. Fluid from the saturated body (1312) may reach the patient's ethmoid bulla (EB) by wicking to port portion (1320), where the medical fluid crosses into the ethmoid bulla (EB).

Various suitable ways in which wicking port (1300) may be deployed will be apparent to those of ordinary skill in the art in view of the teachings herein. For instance, an instrument similar to instrument (100) or instrument (400) may be used to first deploy port portion (1320), with visualization from endoscope (60) and/or some other source of visualization. After port portion (1320) is deployed in the ethmoid bulla (EB), a pair of forceps or some other instrument may be used to wrap the free end of wick portion (1310) about the anterior ridge of the middle turbinate (MT). A mandrel or other feature may be used to hold band (1318) in a straight position before wick portion (1310) is appropriately situated in relation to the middle turbinate (MT). Various other suitable instruments and methods that may be used to deploy wicking port (1300) will be apparent to those of ordinary skill in the art in view of the teachings herein. It should also be understood that port portion (1320) may be installed in a posterior ethmoid sinus (PES) cell or some other location instead of being installed in the ethmoid bulla (EB), if desired. It should also be understood that band (1318) and/or other portions of wicking port (1300) may be formed of bioabsorbable material, if desired.

While the foregoing examples are provided in the context of providing a wick in the ethmoid bulla (EB), it should be understood that wicks may be installed elsewhere within the sinus complex, such as in the sphenoid sinus (SS), in the posterior ethmoid sinus (PES), and/or elsewhere, without necessarily also being installed in the ethmoid bulla (EB). By way of example only, an instrument may be used to form an opening in the middle turbinate vertical basal lamella (MTvBL), medial to the posterior wall of the ethmoid bulla (EB) but lateral to the lateral wall of the vertical basal lamella (MTvBL). A wick may then be deployed in that formed opening. In some instances, the wick may enter the superior meatus, medial to the posterior ethmoid sinus (PES) cells. In some other instances, the wick may enter the anterior-most cell of the posterior ethmoid sinus (PES). In either case, the wick may allow patient-administered substances to reach the posterior ethmoid sinus (PES) cells. Various other ways in which the above described procedures (and in some cases, instruments) may be modified to provide wicks in sinus cells other than the ethmoid bulla (EB) will be apparent to those of ordinary skill in the art in view of the teachings herein.

V. Exemplary Expansion of Retrobullar Space

Figure 19A:
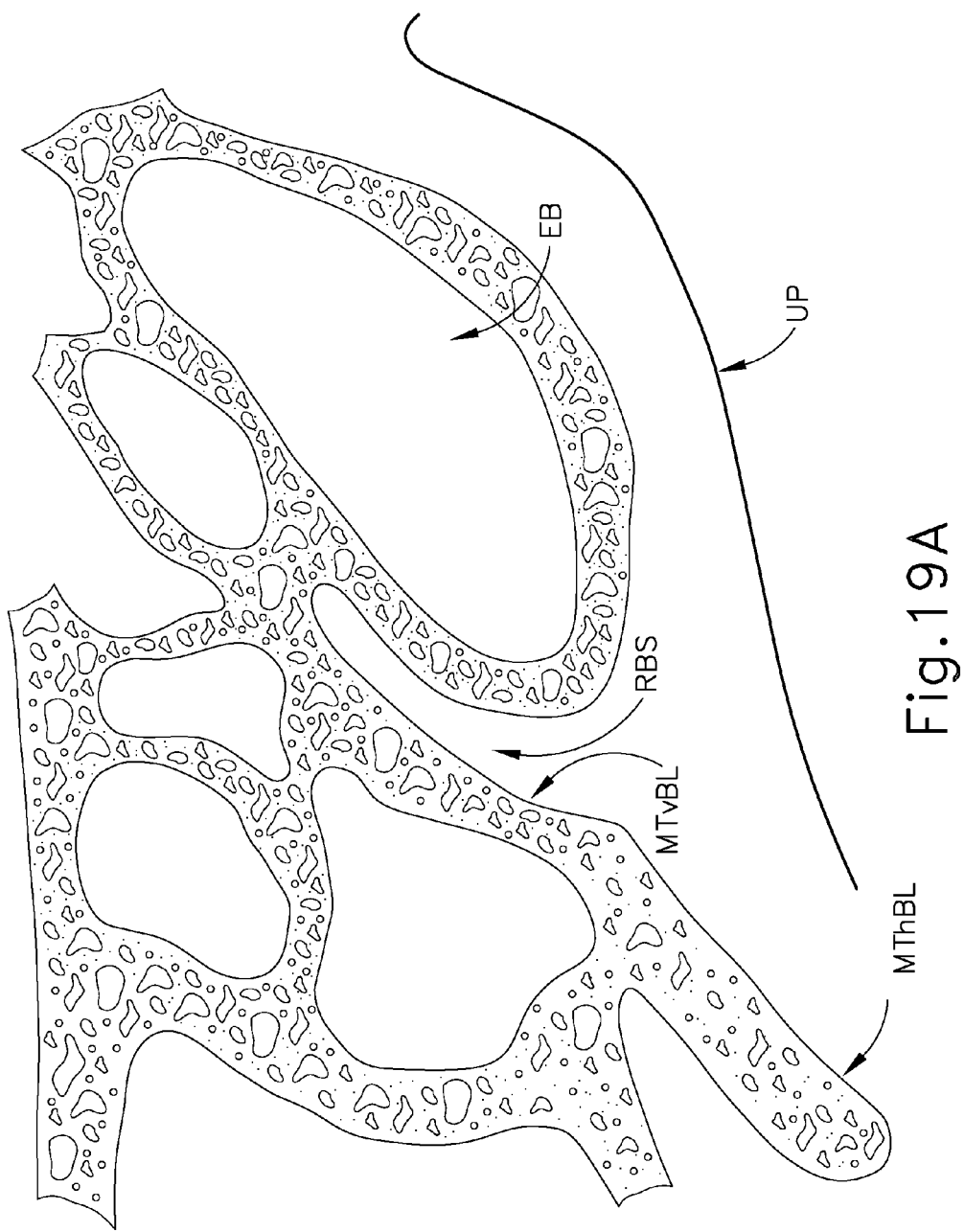
FIG. 19A depicts a left sagittal cross-sectional view of a portion of a human head, showing the retrobullar space in a non-dilated configuration.
Figure 19B:
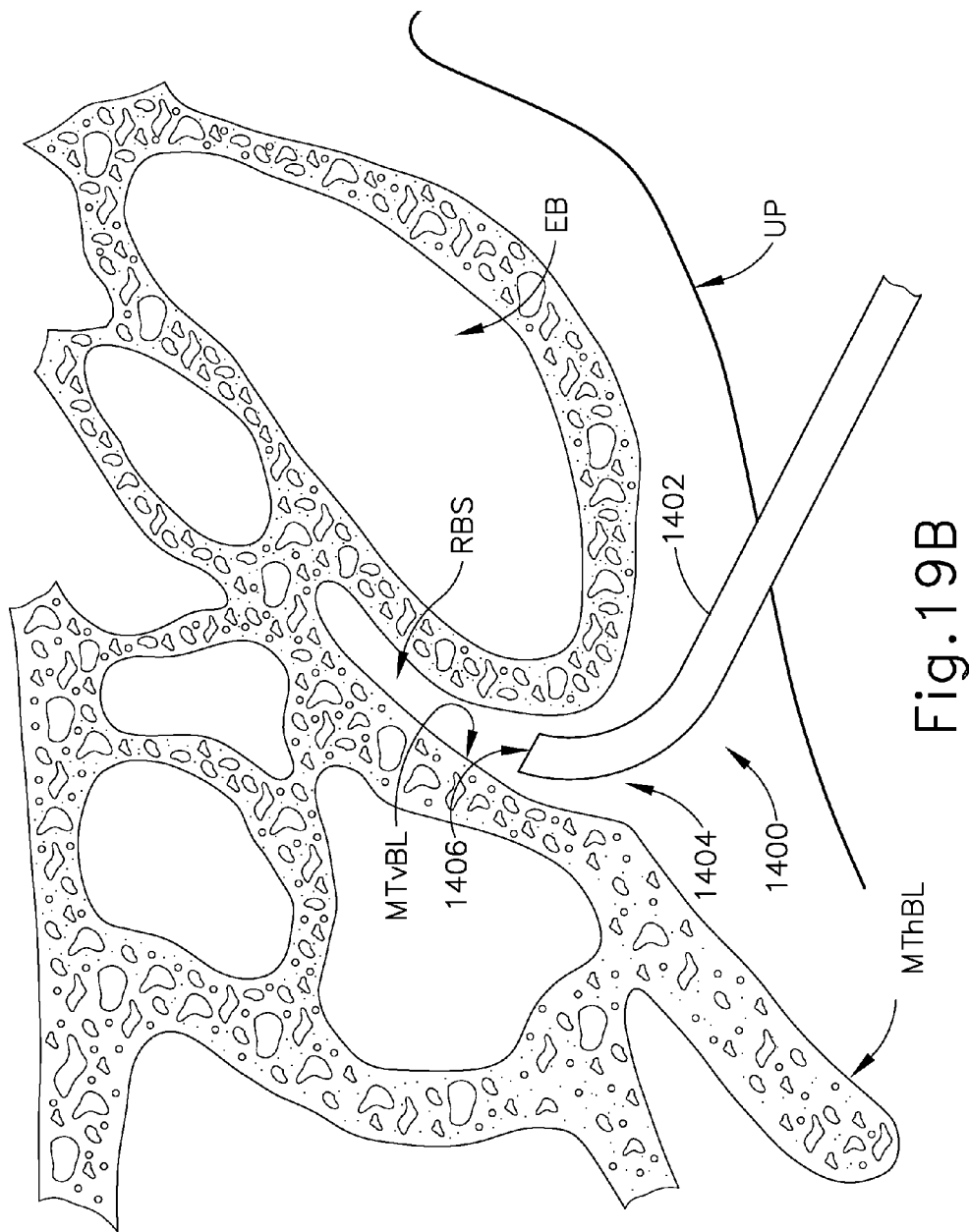
FIG. 19B depicts a left sagittal cross-sectional view of a portion of a human head, with a guide catheter positioned at the retrobullar space.

As noted above, there may be instances where the configuration of the retrobullar space (RBS) may impede flow through the ostium of the ethmoid bulla (EB). It may therefore be desirable to remodel the retrobullar space (RBS) in order to enlarge the transition zone and thereby improve fluid flow into and out of the ethmoid bulla (EB). FIG. 19A shows an exemplary retrobullar space (RBS) before a remodeling procedure. FIG. 19B shows a guide catheter (1400) positioned at the retrobullar space (RBS) to begin a remodeling procedure. Guide catheter (1400) of this example is similar to guide catheter (30) discussed above. Guide catheter (1400) includes a body (1402) having an open distal end (1406) and a bend (1404) just proximal to distal end (1406). Guide catheter (1400) is positioned such that open distal end (1406) is positioned at retrobullar space (RBS), anterior to the middle turbinate vertical basal lamella (MTvBL) and posterior to the posterior wall of the ethmoid bulla (EB). Endoscope (60) or some other visualization device may be used to assist in positioning of guide catheter (1400).

Once guide catheter (1400) has been suitably positioned, a balloon catheter (1410) is advanced through guide catheter (1400) as shown in FIG. 19C. Balloon catheter (1410) has an asymmetrically inflating balloon (1412), which is positioned within the retrobullar space (RBS) at this stage, though balloon (1412) is in a deflated state during advancement and positioning of balloon catheter (1410). While the operator maintains a firm grip on guide catheter (1400) and balloon catheter (1410), balloon (1412) is then inflated as shown in FIG. 19D. In this example, due to the configuration of balloon (1412), rigidity within catheters (1400, 1410), and the operator's firm grip providing a mechanical ground, inflated balloon (1412) only bears anteriorly on the ethmoid bulla (EB) and does not bear posteriorly on the middle turbinate vertical basal lamella (MTvBL). Various suitable ways in which balloon (1412) may be configured to provide such inflation will be apparent to those of ordinary skill in the art in view of the teachings herein. In the present example, inflated balloon (1412) fractures the bone forming the posterior wall of the ethmoid bulla (EB), driving the bone and tissue anteriorly. It should be understood that the fragments formed by fracturing the bone will remain contained within the mucosa, which itself remains intact on both sides of the bone. This is due to the fact that balloon (1412) is an atraumatic device used to move the posterior wall of the ethmoid bulla (EB). A traumatic method of remodeling may cause bone fragments to be released in the nasal cavity, which may require the bone fragments to be carefully removed. Such bone fragment removal may be time consuming and difficult. Thus, using balloon (1412) may make the remodeling process easier and faster than a procedure that uses a traumatic instrument.

Figure 19E:
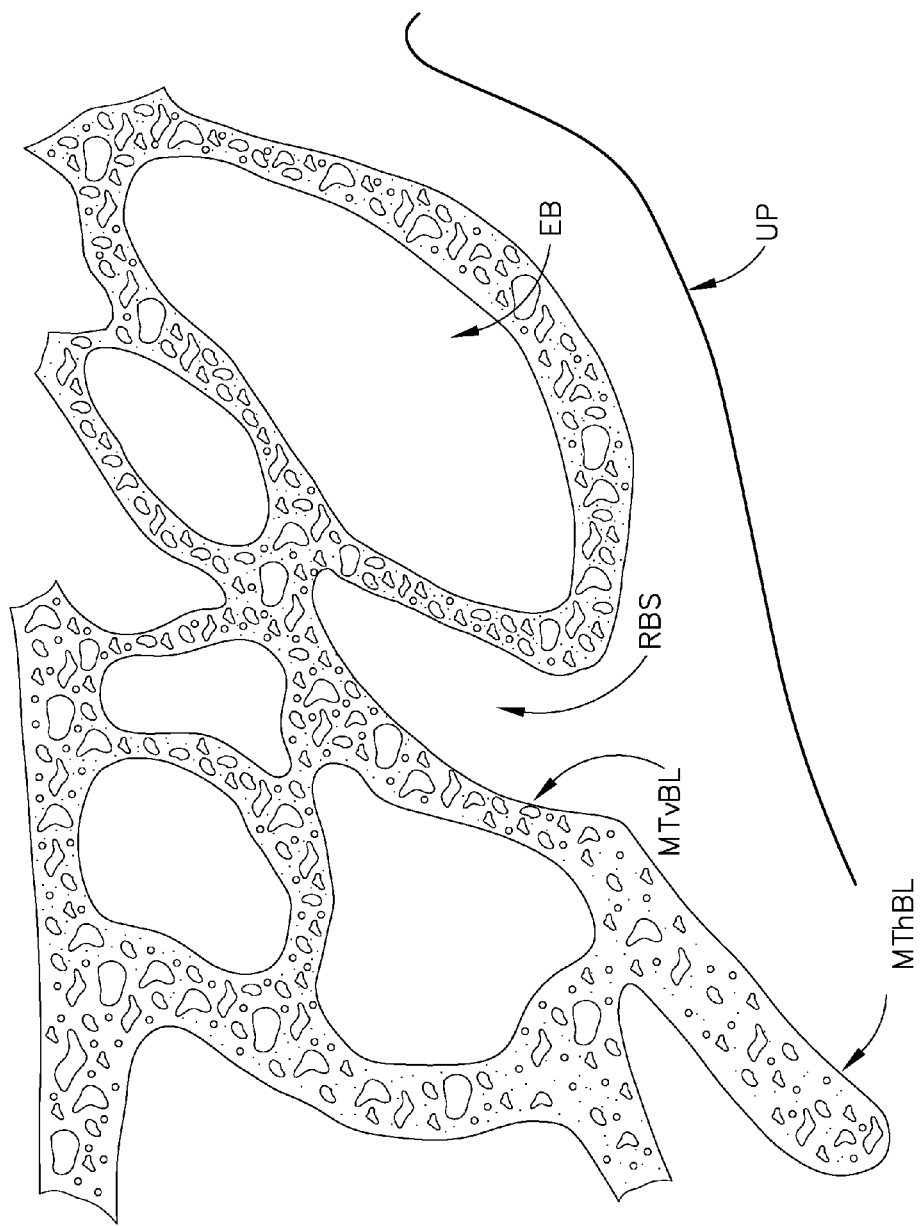
FIG. 19E depicts a left sagittal cross-sectional view of a portion of a human head, showing the retrobullar space in a dilated configuration.

After balloon (1412) has been inflated to the point where balloon (1412) has remodeled the posterior wall of the ethmoid bulla (EB), balloon (1412) is then deflated, and catheters (1400, 1410) are withdrawn from the patient, leaving behind an enlarged retrobullar space (RBS) as shown in FIG. 19E. This enlarged retrobullar space (RBS) shown in FIG. 19E may provide greater fluid communication (e.g., mucus outflow) for ethmoid bulla (EB) than the retrobullar space (RBS) shown in FIG. 19A. In some variations, inflated balloon (1412) bears against the middle turbinate vertical basal lamella (MTvBL) in addition to bearing against the posterior wall of the ethmoid bulla (EB). In some such versions, the strength of the middle turbinate vertical basal lamella (MTvBL) is greater than the strength of the posterior wall of the ethmoid bulla (EB), such that the posterior wall of the ethmoid bulla (EB) is remodeled by inflating balloon (1412) while the middle turbinate vertical basal lamella (MTvBL) is not remodeled by inflating balloon (1412). The vertical basal lamella (MTvBL) may thus provide a mechanical grounding structure for balloon (1412) in some instances.

It should be understood that the retrobullar space (RBS) remodeling procedure described above may be performed in addition to or in lieu of deploying ports and/or wicks as described above. It should also be understood that various other kinds of instruments may be used to perform a retrobullar space (RBS) remodeling procedure. By way of example only, catheters (1400, 1410) or instrument (1500) may be substituted with a dilation instrument as taught in U.S. patent application Ser. No. 13/832,167, entitled "Uncinate Process Support for Ethmoid Infundibulum Illumination," filed on even date herewith, now U.S. Pat. Pub. No. 2014/0275804, published Sep. 18, 2014, the disclosure of which is incorporated by reference herein.

VI. Exemplary Retrobullar Ostium Dilation

Figure 20:
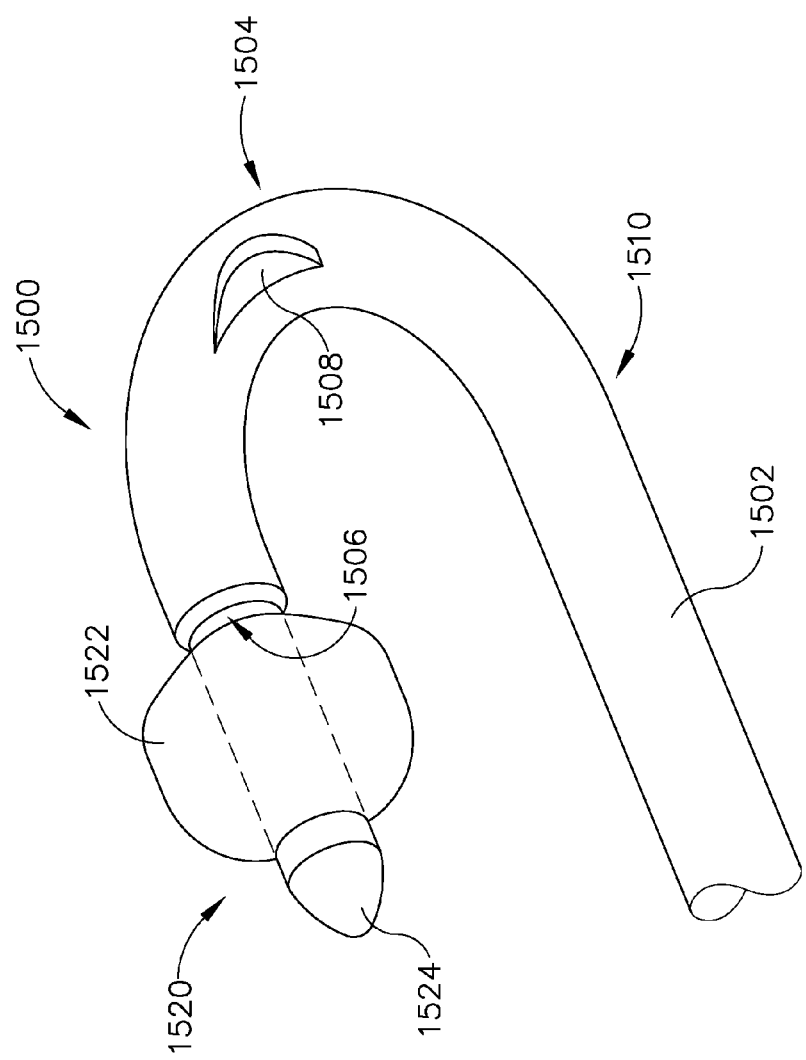
FIG. 20 depicts a perspective view of an exemplary dilation catheter and catheter suitable for dilating an ethmoid bulla ostium.

FIG. 20 shows an exemplary instrument (1500) that may be used to dilate an ostium of the ethmoid bulla (EB) from within the retrobullar space (RBS). Instrument (1500) of this example comprises a guide catheter (1510) and a balloon catheter (1520). Guide catheter (1510) includes a body (1502) having an open distal end (1506) and a bend (1504) just proximal to distal end (1506). While guide catheter (1400) of the example described above reaches the retrobullar space (RBS) from an inferior approach (with distal end (1406) oriented superiorly), guide catheter (1510) of this example reaches the retrobullar space (RBS) from a more medial approach (with distal end (1506) oriented laterally then anteriorly). Bend (1504) of guide catheter (1510) also extends along a greater arc angle than bend (1404) of guide catheter (1400). By way of example only, bend (1504) may extend along an arc angle between approximately 135° and approximately 180°. Bend (1504) is configured to facilitate orienting distal end (1506) directly toward an ostium of the ethmoid bulla (EB) from within the retrobullar space (RBS), anterior to the middle turbinate vertical basal lamella (MTvBL).

Guide catheter (1510) of this example also includes a transversely extending reflective member (1508). Reflective member (1508) is positioned at bend (1504) and facilitates viewing of the retrobullar space (RBS) using an endoscope such as endoscope (60). In some versions, reflective member (1508) may be selectively advanced or retracted transversely relative to body (1502). Various suitable ways in which reflective member (1508) may be selectively advanced or retracted transversely relative to body (1502) will be apparent to those of ordinary skill in the art in view of the teachings herein.

Balloon catheter (1520) of the present example includes an inflatable balloon (1522) and an atraumatic tip (1524) with a rounded/tapered profile that is configured to facilitate insertion into an ostium of the ethmoid bulla (EB). In some versions, balloon catheter (1520) is configured to drive tip (1524) through an ostium when the effective inner diameter of the ostium is less than the outer diameter of tip (1524). Balloon (1522) may be configured substantially similar to dilator (22) described above. Balloon catheter (1520) may be advanced distally through (1510) to expose balloon (1522) relative to distal end (1506). Balloon (1522) may then be inflated with fluid from a fluid source (e.g., inflator (40), etc.) to expand and thereby dilate an ostium.

In an exemplary use, the operator may position guide catheter (1510) such that distal end (1506) is oriented directly toward an ostium of the ethmoid bulla (EB) from within the retrobullar space (RBS). During this positioning, the operator may direct the line of sight for endoscope (60) (or some other visualization device) at reflective member (1508) to obtain a reflected view of the posterior wall of the ethmoid bulla (EB) to visually locate the ostium. Once the guide catheter (1510) is suitably positioned, the operator may advance balloon catheter (1520) distally through guide catheter (1510) such that the tip (1524) of balloon catheter (1520) passes through the ostium. Again, this may be performed using visualization assistance from reflective member (1508). Once balloon (1522) is positioned in the ostium, balloon (1522) may be inflated with fluid (e.g., from inflator (40)) to dilate the ostium. Balloon (1522) may be held in an inflated state for any suitable duration. Balloon (1522) may be repeatedly inflated and deflated as many times as desired. Once balloon (1522) has been finally deflated, balloon (1522) may be retracted back into guide catheter (1510) and instrument (1500) may be removed from the patient's nasal cavity. It should be understood that the retrobullar ostium dilation procedure described above may be performed in addition to or in lieu of deploying ports and/or wicks as described above; and/or in addition to or in lieu of a retrobullar space (RBS) remodeling procedure as described above.

VII. Exemplary Retrobullar Piercing

In addition to or in lieu of installing a port, installing a wick, and/or enlarging the retrobullar space (RBS) by remodeling the posterior wall of the ethmoid bulla (EB), it may be desirable to drive a piercing element into the posterior wall of the ethmoid bulla (EB). In some instances, this may be done to enlarge the size of the naturally occurring ostium that is located at the posterior wall of the ethmoid bulla (EB). In addition or in the alternative, this may be done to create a new ostium for the ethmoid bulla (EB). Whether enlarging an ostium or creating an ostium, this may improve the flow of air and fluid into and out of the ethmoid bulla (EB). Various examples of instruments and procedures that may be used to pierce the posterior wall of the ethmoid bulla (EB) will be described in greater retail below, while other examples will be apparent to those of ordinary skill in the art in view of the teachings herein.

FIGS. 21A-21C show one merely exemplary instrument (1600) that may be used to pierce the posterior wall of the ethmoid bulla (EB). Instrument (1600) of this example comprises a catheter body (1602) having an atraumatic distal tip (1604), a distal balloon (1606), a proximal balloon (1608), and a transverse opening (1610) located between balloons (1606, 1608). Balloons (1606, 1608) are coupled with a fluid source (1632) via a conduit (1630) such that fluid source (1632) may selectively communicate fluid (e.g., saline) to balloons (1606, 1608). FIG. 21A shows balloons (1606, 1608) in a non-inflated state while FIGS. 21B-21C show balloons (1606, 1608) in an inflated state. In the present example, balloons (1606, 1608) are on the same fluid line and are in fluid communication with each other. In some other versions, balloons (1606, 1608) are on independent fluid lines.

Instrument (1600) of this example further includes a piercing element (1620). Piercing element (1620) is slidably disposed within a passageway (1614) in catheter body (1602). Piercing element (1620) includes a sharp distal tip (1622). Tip (1622) is configured to pierce the wall of the ethmoid bulla (EB) without shattering the wall of the ethmoid bulla (EB). In other words, the wall of the ethmoid bulla (EB) remains intact except for the opening created by piercing element (1620), with such an opening being approximately the same size as the outer diameter of piercing element (1620). Passageway (1614) is fluidly isolated from the fluid path for balloons (1606, 1608). The distal end of passageway includes a ramp (1612) leading to transverse opening (1610). While ramp (1612) is shown as being generally planar, it should be understood that ramp (1612) may instead be curved or have some other configuration. Ramp (1612) is configured to guide piercing element (1620) generally transversely out through transverse opening (1610) when piercing element (1620) is advanced distally relative to catheter body (1602) as shown in FIG. 21C. In some instances, piercing element (1620) is resiliently biased to assume the configuration shown in FIG. 21C. In some other instances, piercing element (1620) is not resiliently biased to assume the configuration shown in FIG. 21C and is instead driven to that configuration by ramp (1612). It should be understood that piercing element (1620) is configured such that tip (1622) may be positioned outside an outer diameter region defined by inflated balloons (1606, 1608). Tip (1622) may thus pass through a tissue wall that is engaged by balloons (1606, 1608), as described below.

Figure 22B:
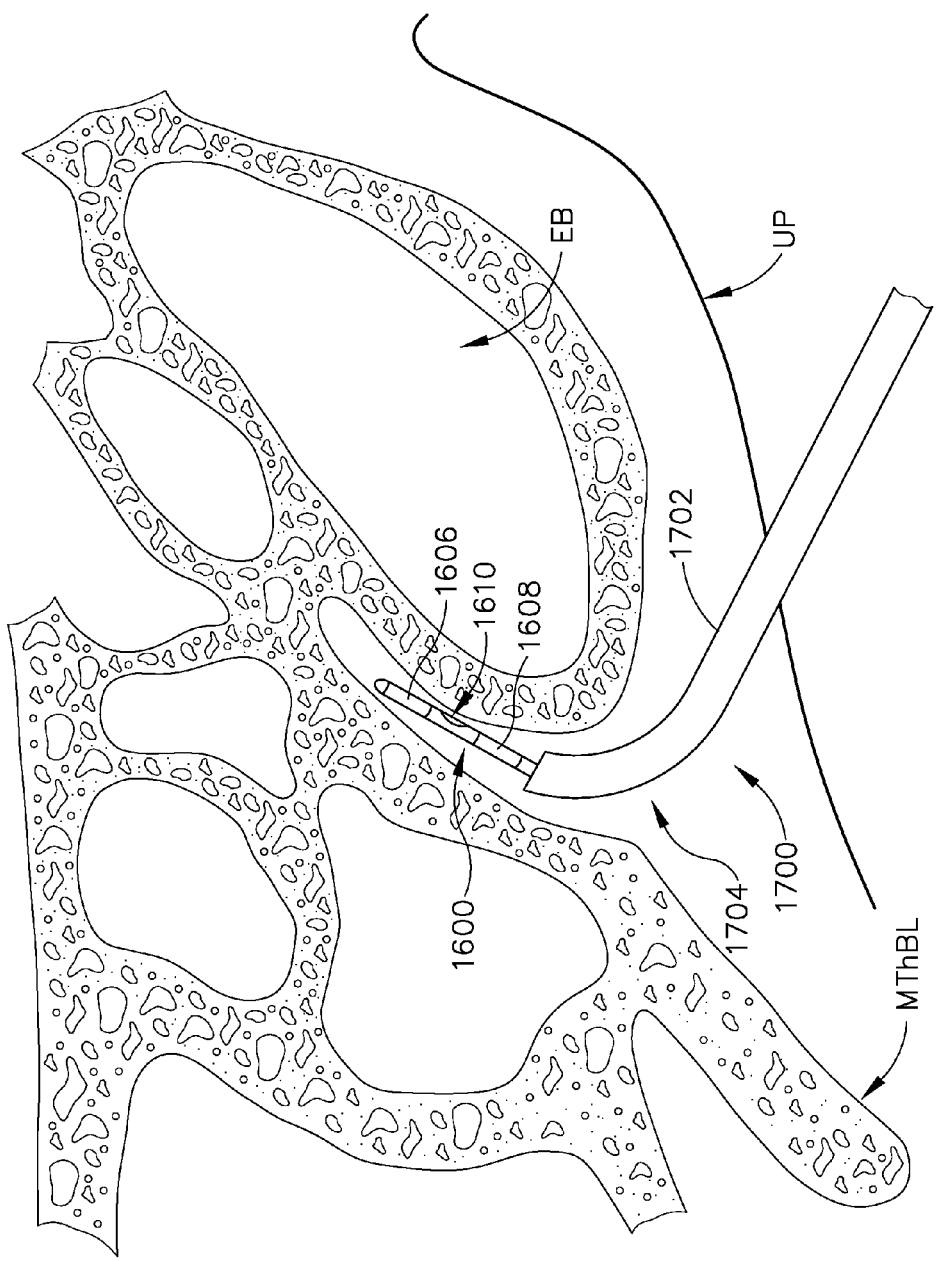
FIG. 22B depicts a left sagittal cross-sectional view of a portion of a human head, with the piercing catheter of FIG. 21A advanced through the guide catheter into the retrobullar space.

FIGS. 22A-22E show a process where instrument (1600) is used to pierce the posterior wall of the ethmoid bulla (EB). In particular, FIG. 22A shows a guide catheter (1700) positioned at the retrobullar space (RBS). Guide catheter (1700) of this example is substantially identical to guide catheter (1400) discussed above. Guide catheter (1700) includes a body (1702) having an open distal end (1706) and a bend (1704) just proximal to distal end (1706). Guide catheter (1700) is positioned such that open distal end (1706) is positioned at retrobullar space (RBS), anterior to the middle turbinate vertical basal lamella (MTvBL) and posterior to the posterior wall of the ethmoid bulla (EB). Endoscope (60) or some other visualization device may be used to assist in positioning of guide catheter (1700).

Once guide catheter (1700) has been suitably positioned, instrument (1600) is advanced through guide catheter (1700) as shown in FIG. 22B. Balloons (1606, 1608) are both in a deflated state (see also FIG. 21A) during this advancement of instrument (1600). Piercing element (1620) is also in a retracted state during this advancement of instrument (1600). Instrument (1600) is oriented such that transverse opening (1610) faces the posterior wall of the ethmoid bulla (EB). In some instances, this orientation is achieved through direct visualization. In some other instances, this orientation is achieved through complementary features of guide catheter (1700) and instrument (1600). For instance, such complementary features may operate on an assumption that the inner region of bend (1704) is oriented toward the ethmoid bulla (EB). The complementary features may include a visual indicator on guide catheter (1700) that is aligned with the inner region of bend (1705) and a visual indicator on catheter body (1602) that is aligned with transverse opening (1610), such that the operator may rotate catheter body (1602) relative to guide catheter (1700) until these visual indicators are aligned with each other. Alternatively, complementary notch and protrusion may mate when catheter body (1602) is properly oriented relative to guide catheter (1700). As yet another merely illustrative example, catheter body (1602) may be keyed to guide catheter (1700), providing a poka-yoke feature that ensures consistent alignment between transverse opening (1610) and the inner region of bend (1704). Other suitable features will be apparent to those of ordinary skill in the art in view of the teachings herein.

Figure 22C:
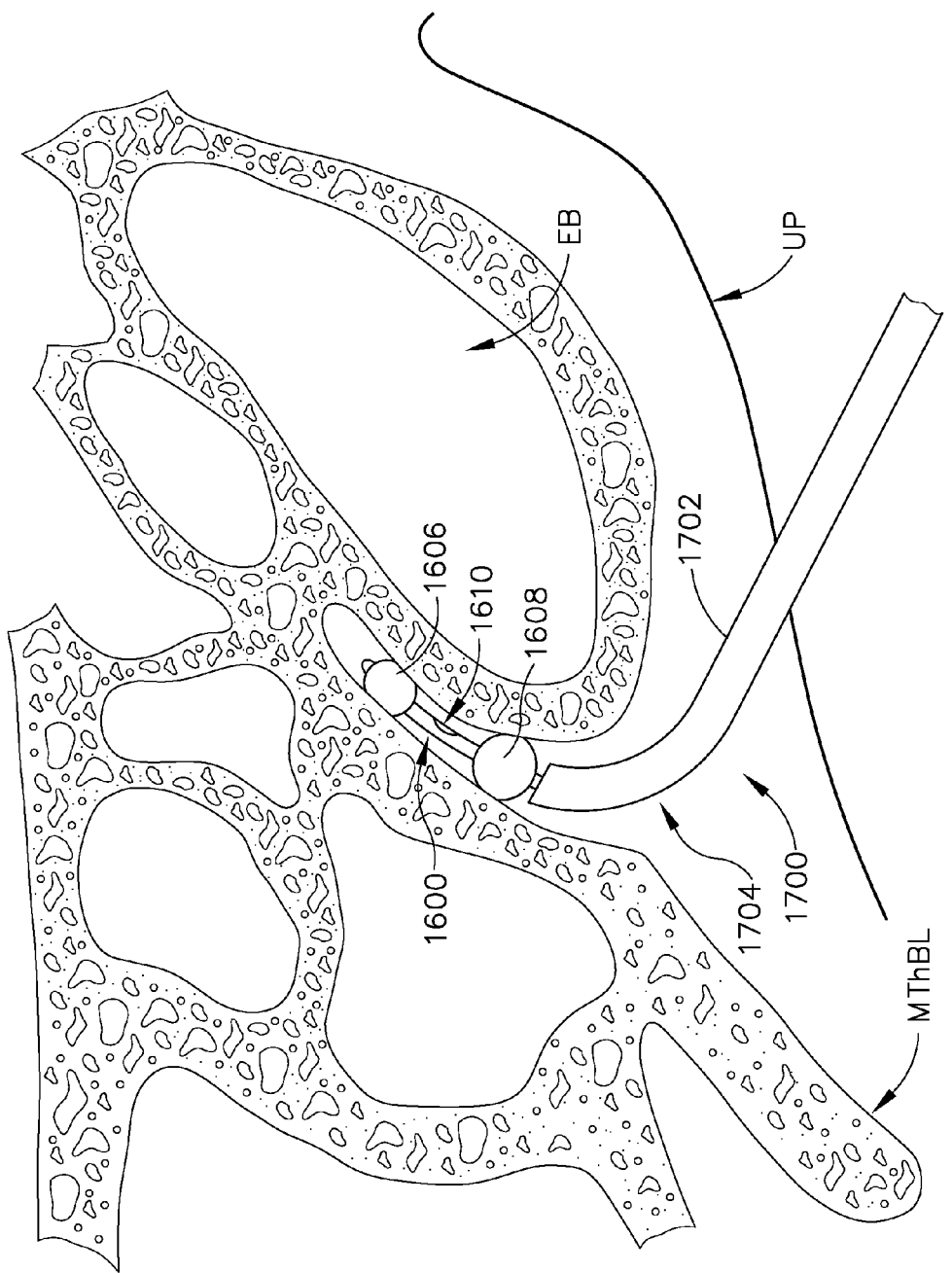
FIG. 22C depicts a left sagittal cross-sectional view of a portion of a human head, with the balloons of the piercing catheter of FIG. 21A in an inflated state in the retrobullar space.

Once instrument (1600) has been suitably positioned, fluid source (1632) is actuated to drive fluid into balloons (1606, 1608), thereby inflating balloons (1606, 1608) as shown in FIG. 22C (see also FIG. 21B). In the present example, balloons (1606, 1608) are only inflated with enough fluid pressure to provide structural support of catheter body (1602) in the retrobullar space (RBS). Balloons (1606, 1608) are not inflated to the point where they remodel the retrobullar space (RBS) by fracturing the middle turbinate vertical basal lamella (MTvBL) or the posterior wall of the ethmoid bulla (EB). In some other instances, though, balloons (1606, 1608) may in fact be inflated to the point where hey remodel the retrobullar space (RBS) by fracturing the middle turbinate vertical basal lamella (MTvBL) and/or the posterior wall of the ethmoid bulla (EB). Piercing element (1620) remains in the retracted position until balloons (1606, 1608) are sufficiently inflated.

Figure 22D:
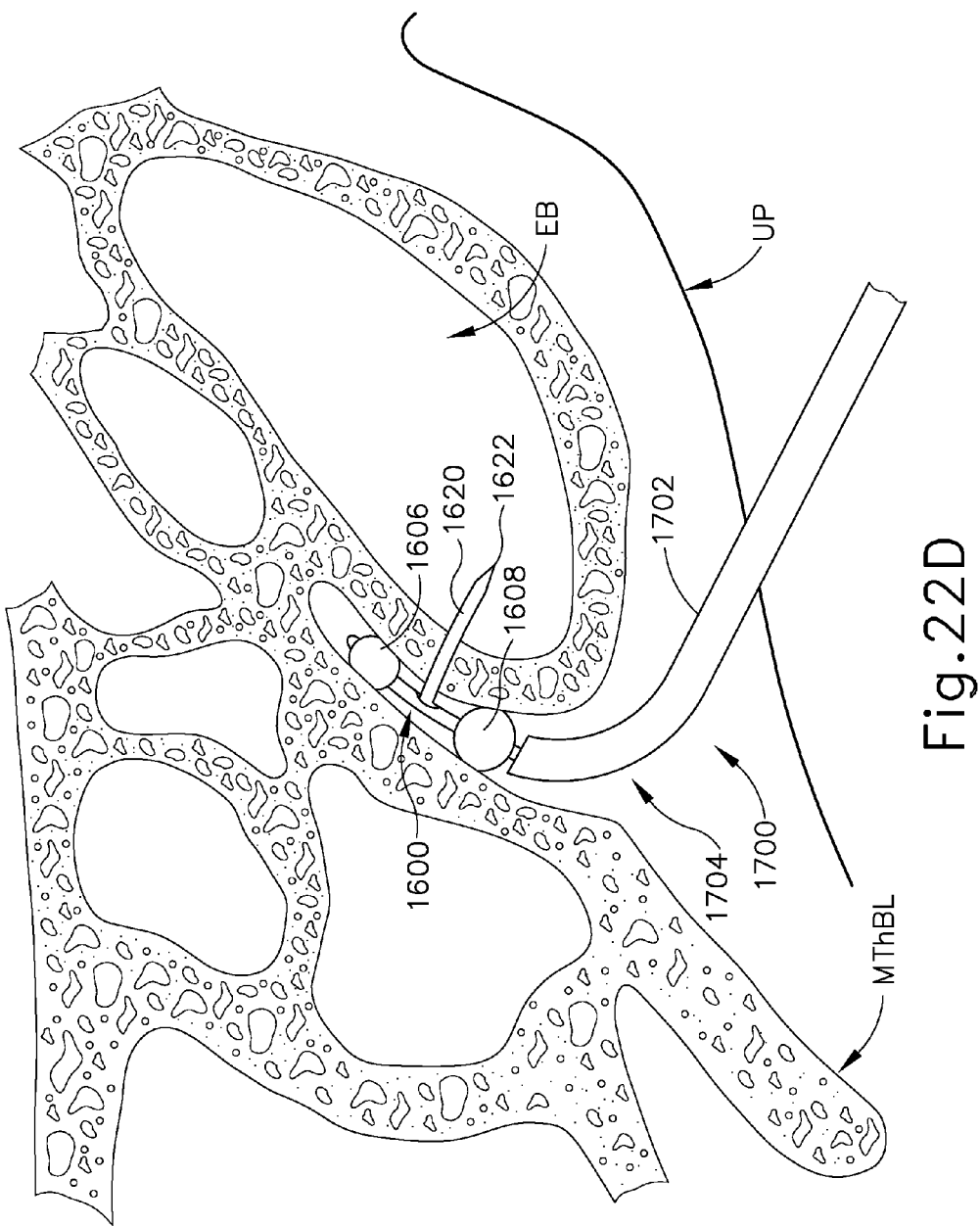
FIG. 22D depicts a left sagittal cross-sectional view of a portion of a human head, with the piercing element of the piercing catheter of FIG. 21A advanced to pierce a posterior wall of the ethmoid bulla.
Figure 22E:
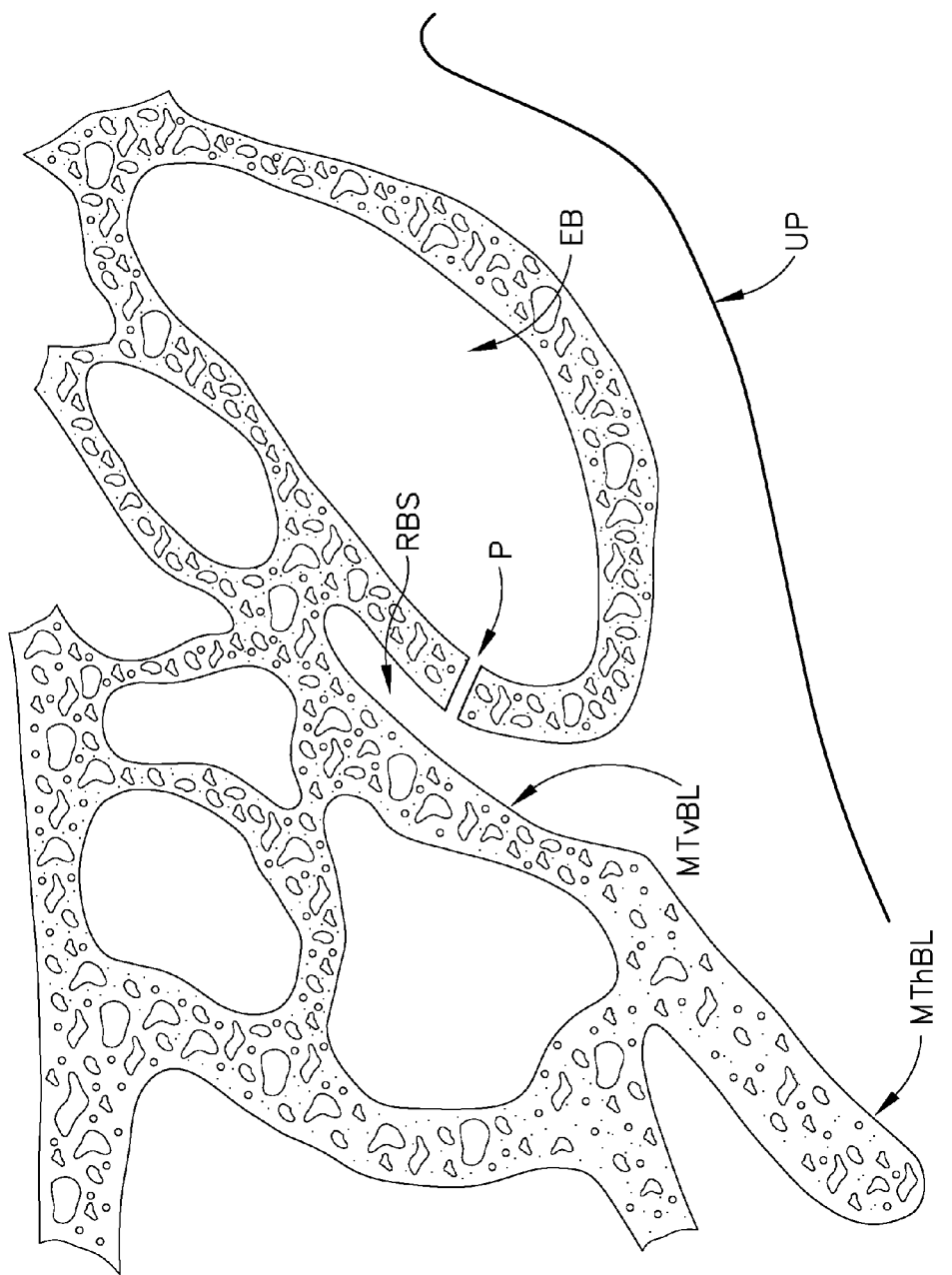
FIG. 22E depicts a left sagittal cross-sectional view of a portion of a human head, showing the pierced posterior wall of the ethmoid bulla.

After balloons (1606, 1608) have been sufficiently inflated, piercing element (1620) is advanced distally as shown in FIG. 22D (see also FIG. 21C). This drives tip (1622) along a generally transverse path such that tip (1622) pierces the posterior wall of the ethmoid bulla (EB). In some instances, a port or wick is deployed in the posterior wall of the ethmoid bulla (EB). In addition or in the alternative, the ethmoid bulla (EB) may be flushed with saline and suction through the opening formed by tip (1622). In the present example, however, piercing element (1620) is simply retracted proximally back into catheter body (1602), balloons (1606, 1608) are deflated, and instrument (1600) and catheter (1700) are removed from the nasal cavity, leaving behind a newly formed passageway (P) in the posterior wall of the ethmoid bulla (EB). This newly formed passageway (P) provides improved fluid communication between the ethmoid bulla (EB) and the transition zone provided by the retrobullar space (RBS). While piercing element (1622) is used to form a new passageway (P) in this example, it should be understood that piercing element (1622) may instead be used to widen an existing ostium or passageway. For instance, piercing element (1622) may be used to widen a naturally occurring ostium or an ostium that has been created using an instrument.

Figure 23:
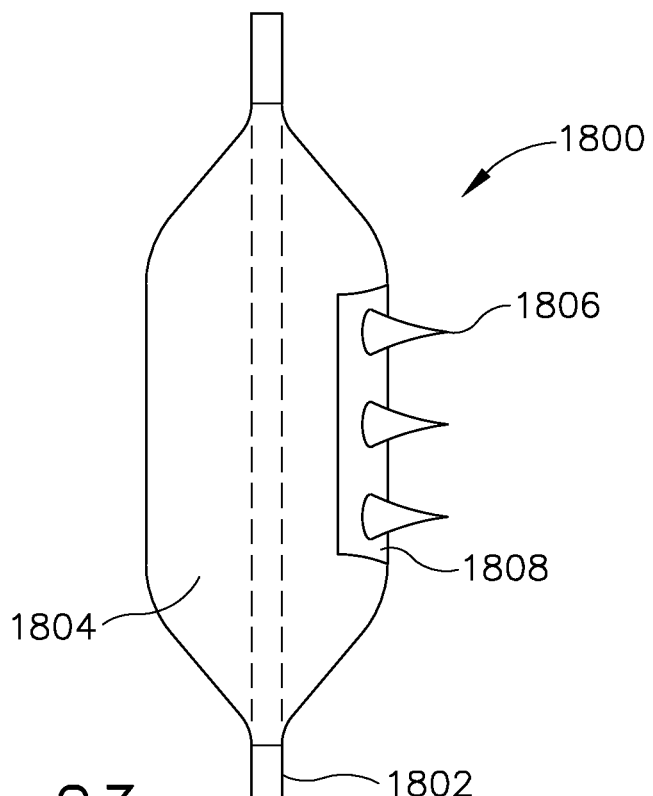
FIG. 23 depicts a side elevational view of an exemplary alternative piercing catheter.

FIG. 23 shows another exemplary instrument (1800) that may be used to pierce the posterior wall of the ethmoid bulla (EB). Instrument (1800) of this example comprises a catheter body (1802), a balloon (1804), and a plurality of spikes (1806) secured to a base (1808). Base (1808) is secured to balloon (1804) such that balloon (1804) will drive spikes (1806) outwardly when balloon (1804) is inflated, with base (1808) providing support for spikes (1806) over a substantial surface area of balloon (1804). Instrument (1800) may be used in place of instrument (1600) described above in order to create new ostia in the posterior wall of the ethmoid bulla (EB). In particular, instrument (1800) may be advanced through guide catheter (1700) while balloon (1804) is in a non-inflated state until balloon (1804) reaches the retrobullar space (RBS). Once balloon (1804) is in the retrobullar space (RBS) and spikes (1806) are pointed toward the posterior wall of the ethmoid bulla (EB), the balloon (1804) is inflated to drive spikes (1806) through the posterior wall of the ethmoid bulla (EB). Balloon (1804) is then deflated and instrument (1800) is removed with guide catheter (1700), leaving behind ostia formed by spikes (1806) in the posterior wall of the ethmoid bulla (EB). In some instances, balloon (1804) is inflated to a point where balloon (1804) remodels the retrobullar space (RBS) by fracturing the middle turbinate vertical basal lamella (MTvBL) or the posterior wall of the ethmoid bulla (EB), though this is of course merely optional.

Figure 24:
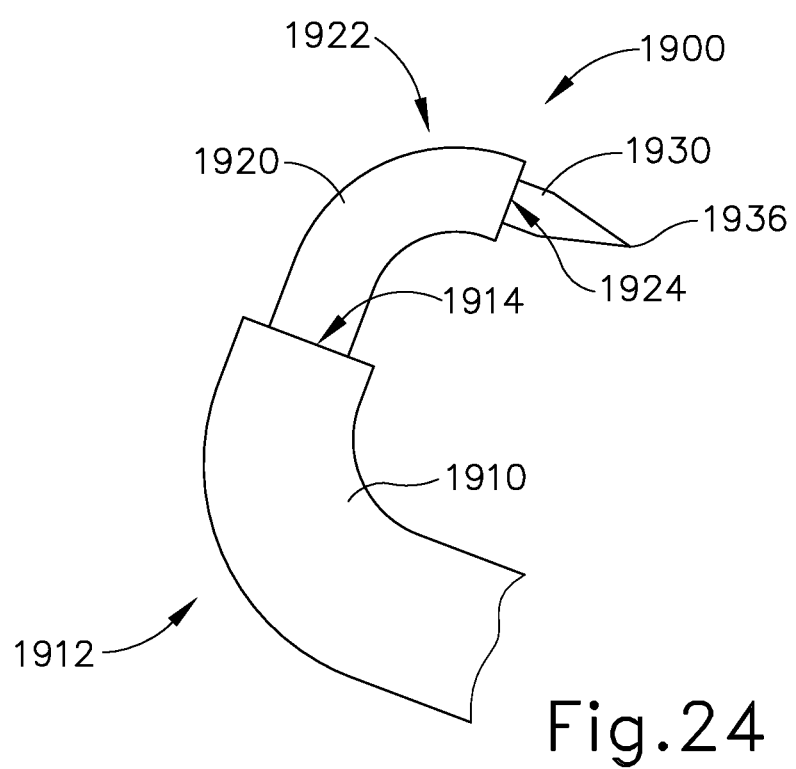
FIG. 24 depicts a side elevational view of another exemplary alternative piercing catheter.

FIG. 24 shows yet another exemplary instrument (1900) that may be used to pierce the posterior wall of the ethmoid bulla (EB). Instrument (1900) of this example comprises a guide catheter (1910) having a bend (1912) and an open distal end (1914). A secondary guide (1920) is slidably disposed in guide catheter (1910) and has another bend (1922) and an open distal end (1924). Secondary guide (1920) is resiliently biased to define bend (1922) but is configured to assume a straight configuration when retracted and confined within guide catheter (1910). A piercing element (1930) is slidably disposed in secondary guide (1920) and has a piercing tip (1936). Piercing element (1930) is flexible enough to slide along the paths formed by bends (1912, 1922) yet has sufficient strength to pierce the posterior wall of the ethmoid bulla (EB). Bend (1912) spans approximately 90 degrees while bend (1922) also spans approximately 90 degrees, such that guide catheter (1910) and secondary guide (1920) together are configured to redirect piercing element (1930) approximately 180 degrees. This may enable piercing element (1930) to readily reach the posterior wall of the ethmoid bulla (EB). In addition to forming a new ostium in the ethmoid bulla (EB), it should be understood that instrument (1900) may also be used to enlarge an ostium that is already present. Such a pre-existing ostium may be a naturally occurring ostium or an ostium that was created by an instrument such as any of the piercing instruments (1600, 1800, 1900) described herein, etc. Piercing element (1930) and secondary guide (1920) may both be retracted relative to guide catheter (1910) during positioning of instrument (1900) in the patient and during removal of instrument (1900) from the patient.

While the foregoing examples are provided in the context of piercing a wall of the ethmoid bulla (EB), it should be understood that similar procedures may be performed elsewhere within the sinus complex, such as in the sphenoid sinus (SS), or in the posterior ethmoid sinus (PES). By way of example only, an instrument may be used to form an opening in the middle turbinate vertical basal lamella (MTvBL), medial to the posterior wall of the ethmoid bulla (EB) but lateral to the lateral wall of the vertical basal lamella (MTvBL). The formed opening may serve to increase ventilation to the posterior ethmoid sinus (PES) cells and allow patient-administered substances to reach the posterior ethmoid sinus (PES) cells. Various ways in which the above described procedures (and in some cases, instruments) may be modified to create ostia for sinus cells other than the ethmoid bulla (EB) will be apparent to those of ordinary skill in the art in view of the teachings herein.

VIII. Exemplary Additional Piercing Variations

As noted above, the wall defining a sinus cavity may be pierced for various purposes, including but not limited to deploying a port, deploying a wick, or simply creating a new ostium. Several examples of instruments that may be used to pierce the wall of a sinus cavity have been described above. It should be understood that sinus wall piercing elements may include trocar type tips, coring tips, and other types of tips. Such tips may be advanced without rotation, advanced with rotation (e.g., in full rotations or angularly reciprocating partial rotations), advanced with longitudinal reciprocation (e.g., in a jackhammering action), or advanced with both rotation and longitudinal reciprocation. Piercing tips may have a sharp edge and/or an abrasive edge. As used herein, the term "piercing" should be understood to include various forms of cutting. For instance, a piercing element may also be configured to cut a slice out of a sinus wall. This may include corner slicing, medial slicing, or other forms of slicing/cutting. In some instances an act of cutting leaves a mucosal flap that can cover over exposed bone. When a cut leaves exposed bone or a tattered tissue edge, the same may be covered with a conformal material and/or curing material. Additional examples of piercing/cutting elements will be described in greater detail below; while further examples will be apparent to those of ordinary skill in the art in view of the teachings herein.

Figure 25:
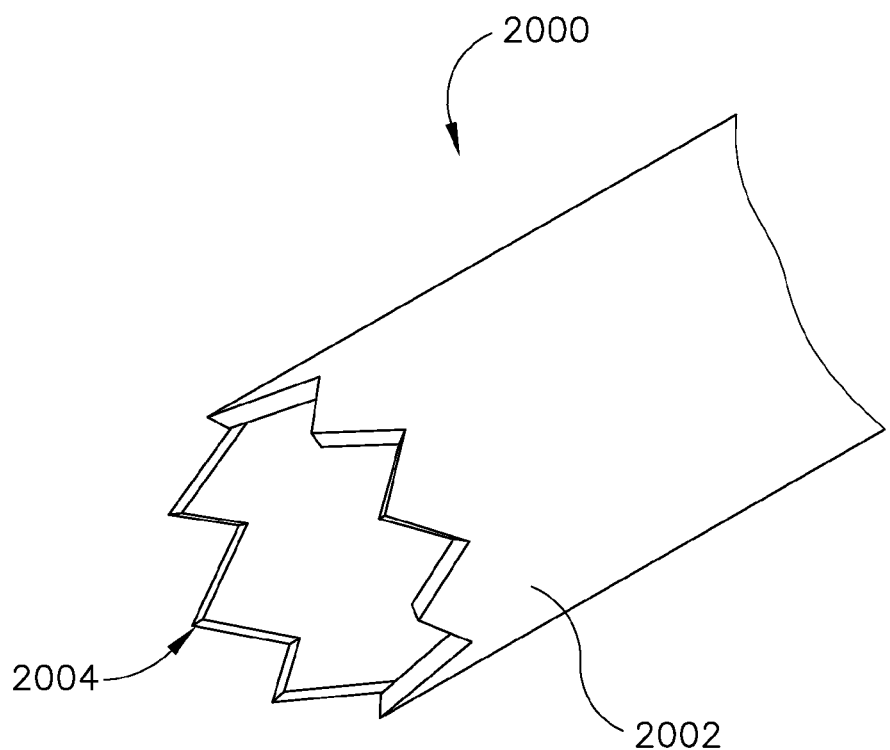
FIG. 25 depicts a perspective view of the distal end of an exemplary alternative sinus wall piercing element.

FIG. 25 shows an exemplary piercing tip (2000) that may be used to form an opening in a sinus wall. Piercing tip (2000) of this example comprises a tubular portion (2002) with a plurality of sharp points (2004) angularly arrayed about its distal edge. Piercing tip (2000) may be rotated about its longitudinal axis while being advanced along its longitudinal axis to pierce a sinus wall. In some versions where piercing tip (2000) is used to pierce the wall of an ethmoid bulla (EB), piercing tip (2000) is advanced in the posterior direction. In some such versions, a back support (not shown) may be positioned within the retrobullar space (RBS). Such a support may be an integral feature of the instrument that includes piercing tip (2000) or may be part of a separate instrument. In addition or in the alternative, some exemplary uses may include first partially driving sharp points (2004) into the sinus wall without rotating piercing tip (2000) (e.g., stopping advancement as soon as sharp points (2004) have reached the bone), then subsequently initiating rotation and further advancement of piercing tip (2000) to complete the piercing process. Other suitable ways in which piercing tip (2000) may be used will be apparent to those of ordinary skill in the art in view of the teachings herein.

Figure 26D:
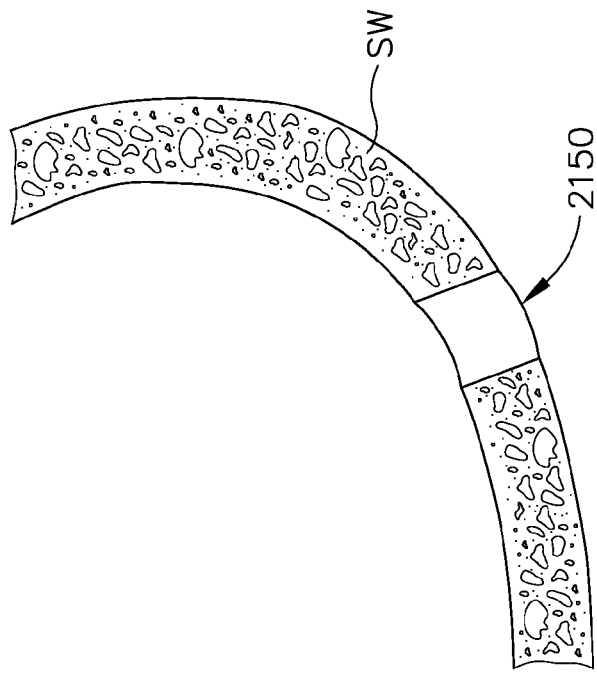
FIG. 26D depicts a cross-sectional view of the sinus wall of FIG. 26A after completion of a procedure with the piercing instrument of FIG. 26A.
Figure 26C:
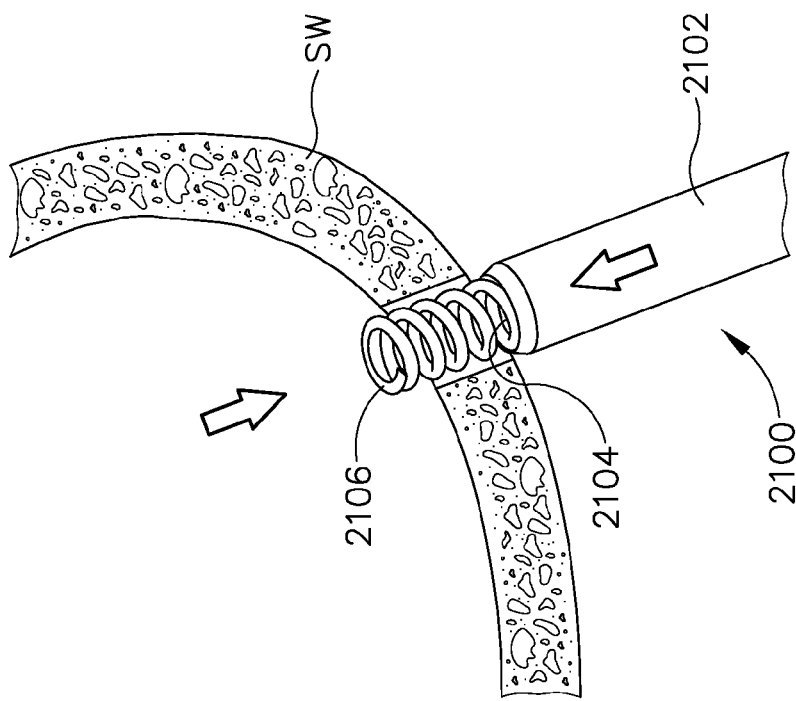
FIG. 26C depicts an elevational view of the distal end of the piercing instrument of FIG. 26A, with the sinus wall in cross section, and with the piercing element being reciprocated in the sinus wall.

FIGS. 26A-26C show another exemplary instrument (2100) that may be used to form an opening in a sinus wall (SW). The sinus wall (SW) may be a wall of the ethmoid bulla (EB) or the wall of some other sinus cavity. Instrument (2100) of this example comprises a tubular outer sheath (2102) with a distal opening (2104). In some versions, distal opening (2104) is defined by a sharp edge. Instrument (2100) further includes an inner coil member (2106) that has a corkscrew configuration. Inner coil member (2106) is operable to rotate and translate relative to outer sheath (2102). As shown in FIG. 26A, instrument (2100) is positioned such that distal opening (2104) is located at the sinus wall (SW). Inner coil member (2106) is then driven through the sinus wall (SW) while outer sheath (2102) remains stationary, as shown in FIG. 26B. In the present example, inner coil member (2106) rotates as it advances longitudinally. With the inner coil member (2106) disposed in the sinus wall (SW), instrument (2100) is then reciprocated longitudinally as shown in FIG. 26C. In some versions, this reciprocation involves only coil member (2106), while outer sheath (2102) remains stationary. In some other versions, this reciprocation also involves outer sheath (2102), such that the distal edge defining distal opening (2104) is driven through sinus wall (SW). In either case, the reciprocation enlarges the initial opening formed by coil member (2106).

FIGS. 27A-27C and 28A-28C show another exemplary instrument (2200) that may be used to form an opening in a sinus wall (SW). The sinus wall (SW) may be a wall of the ethmoid bulla (EB) or the wall of some other sinus cavity. Instrument (2200) of this example comprises an elongate member (2202) having a curved distal end terminating in a sharp tip (2204). Instrument (2200) further comprises a cutting member (2206) that is slidably disposed about elongate member (2202). In the present example, cutting member (2206) has a sharp distal edge (2208) and a U-shaped profile. Distal edge (2208) further extends along at least part of the length of cutting member (2206) in the present example. Of course, cutting member (2206) may have various other configurations.

Figure 27D:
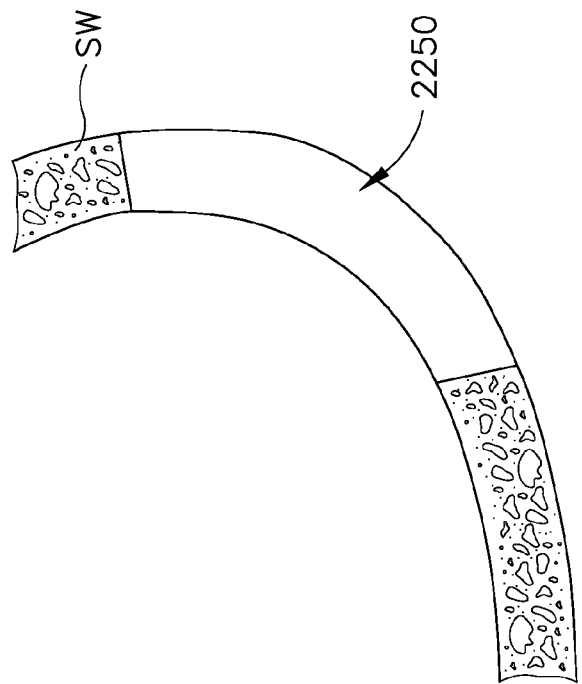
FIG. 27D depicts a cross-sectional view of the sinus wall of FIG. 27A after completion of a procedure with the piercing instrument of FIG. 27A.
Figure 27C:
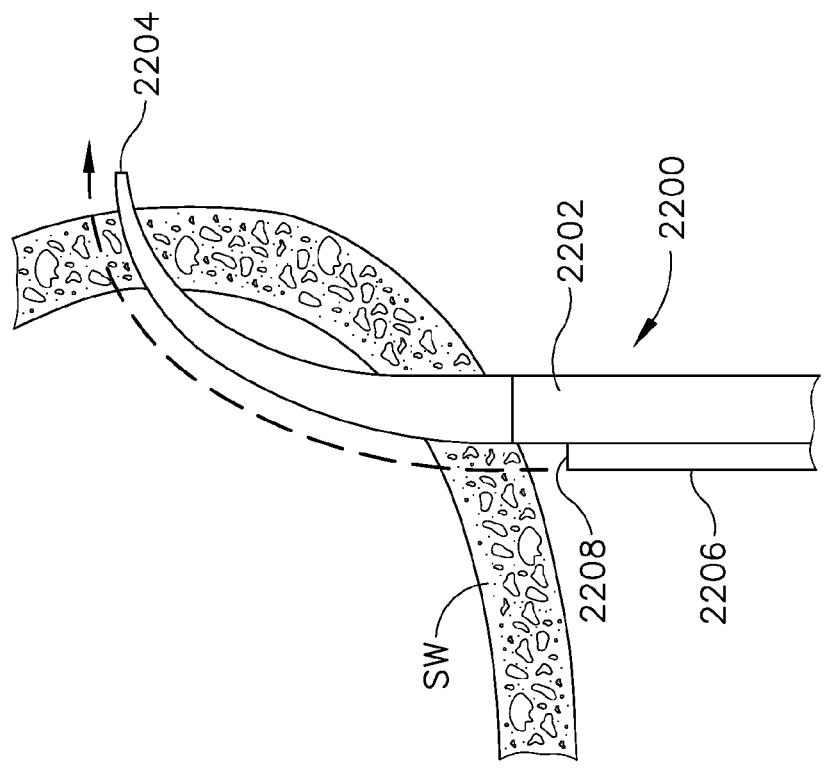
FIG. 27C depicts an elevational view of the distal end of the piercing instrument of FIG. 27A, with the sinus wall in cross section, with the piercing element advanced through the sinus wall, and with the wall cutter being advanced toward the sinus wall.
Figure 28D:
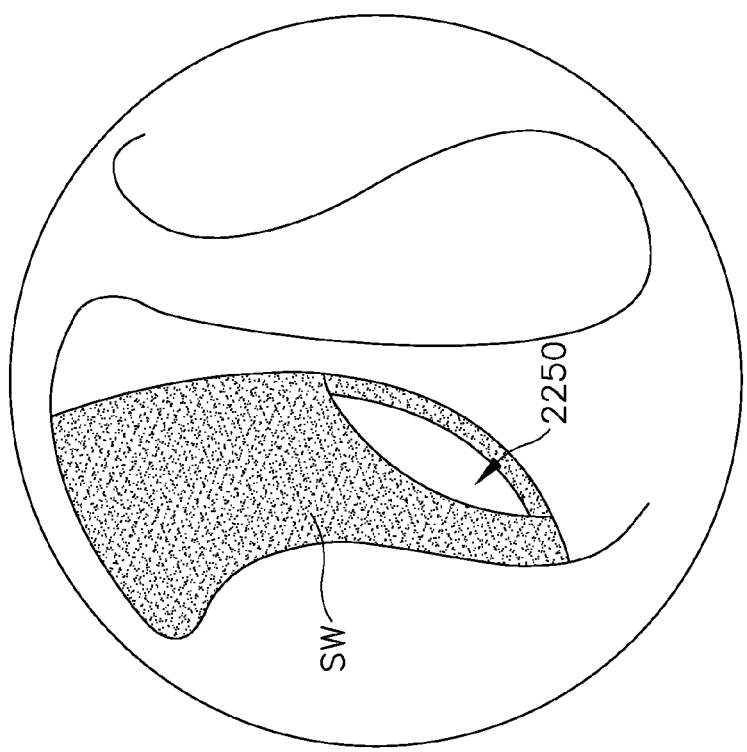
FIG. 28D depicts a perspective view of the sinus wall of FIG. 27A after completion of a procedure with the piercing instrument of FIG. 27A.
Figure 28C:
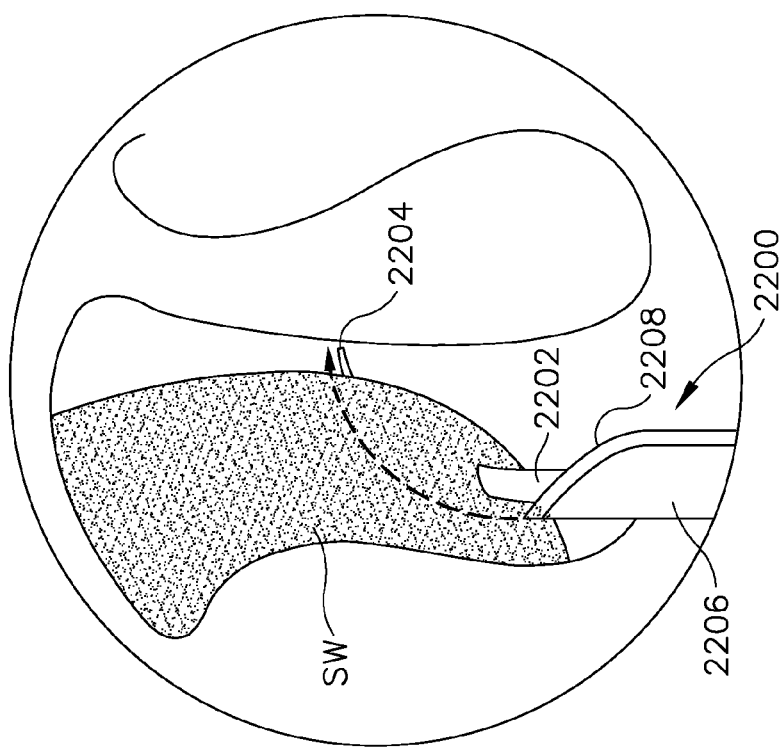
FIG. 28C depicts a perspective view of the distal end of the piercing element of FIG. 27A, with the piercing element advanced through the sinus wall, and with the wall cutter being advanced toward the sinus wall.

As shown in FIGS. 27A and 28A, instrument (2200) may be initially positioned such that tip (2204) is at a sinus wall (SW), with cutting member (2206) in a retracted position (retracted out of view in FIGS. 27A and 28A). Elongate member (2202) is then advanced through the sinus wall (SW), while cutting member (2206) remains in a retracted position. As shown in FIGS. 27B and 28B, tip (2204) has passed through the sinus wall (SW) twice due to the curved configuration of the distal end of elongate member (2202). Next, cutting member (2206) is advanced along elongate member (2202), while elongate member (2202) remains stationary, as shown in FIGS. 27C and 28C. Cutting member (2206) is configured to follow the curved path defined by the distal end of elongate member (2202); and is further configured to travel to a point where sharp distal edge (2208) is positioned by tip (2204). During this advancement, sharp distal edge (2208) cuts through the sinus wall (SW) twice. It should be understood that elongate member (2202) anchors instrument (2200) in the sinus wall (SW) and may further provide structural support to the sinus wall (SW) as cutting member (2206) traverses the sinus wall (SW). Instrument (2200) is then withdrawn from sinus wall (SW), leaving behind an opening (2250) as shown in FIGS. 27D and 28D. Various other suitable features of instrument (2200) and methods of using instrument (2200) will be apparent to those of ordinary skill in the art in view of the teachings herein.

FIGS. 29A-29C and 30A-30C show another exemplary instrument (2300) that may be used to form an opening in a sinus wall (SW). The sinus wall (SW) may be a wall of the ethmoid bulla (EB) or the wall of some other sinus cavity. Instrument (2300) of this example comprises an elongate shaft (2302) having a plurality of transversely extending sharp-tipped claw members (2304) at its distal end. In the present example, claw members (2304) are selectively retracted and extended relative to shaft (2302). Claw members (2304) are configured to extend and retract along curved paths, such that claw members (2304) on opposing sides of a longitudinally extending transverse plane extend toward each other in a grabbing action as claw members (2304) are advanced to extended positions. Various suitable ways in which claw members (2304) may be selectively retracted and extended relative to shaft (2302) will be apparent to those of ordinary skill in the art in view of the teachings herein.

Figure 30B:
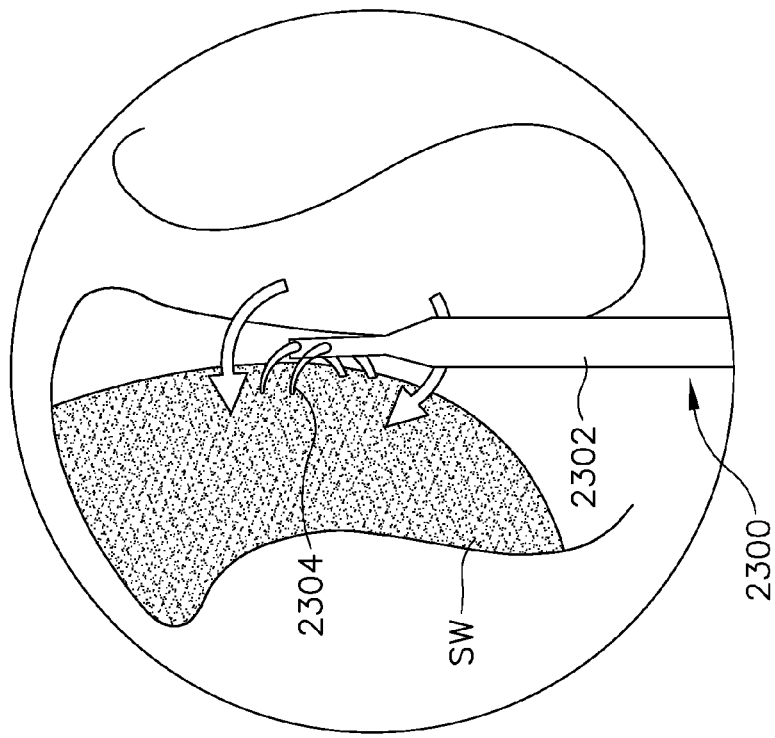
FIG. 30B depicts a perspective view of the distal end of the piercing element of FIG. 29A, with piercing elements advanced through the sinus wall.
Figure 30A:
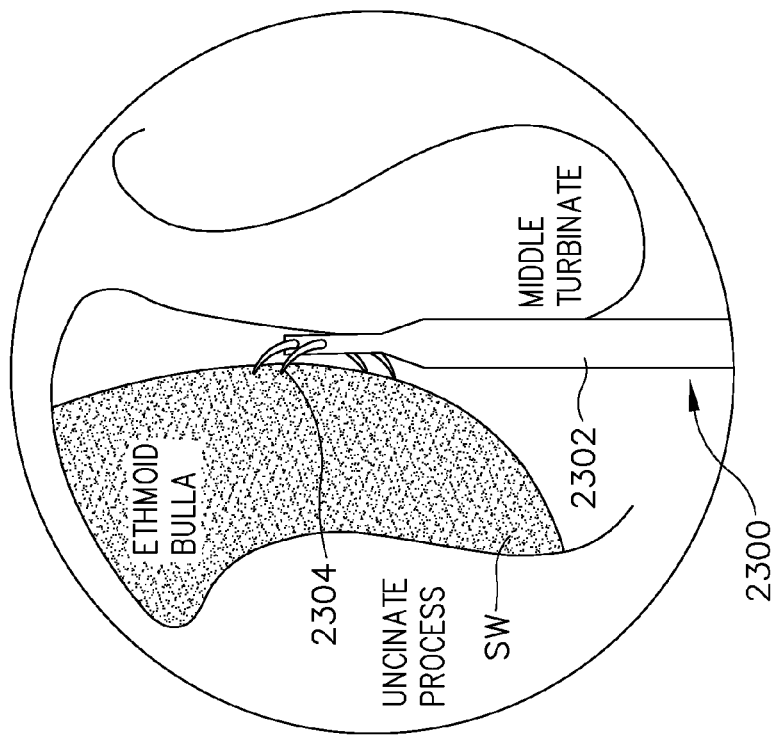
FIG. 30A depicts a perspective view of the distal end of the piercing element of FIG. 29A, with the piercing elements adjacent to the sinus wall.
Figure 30D:
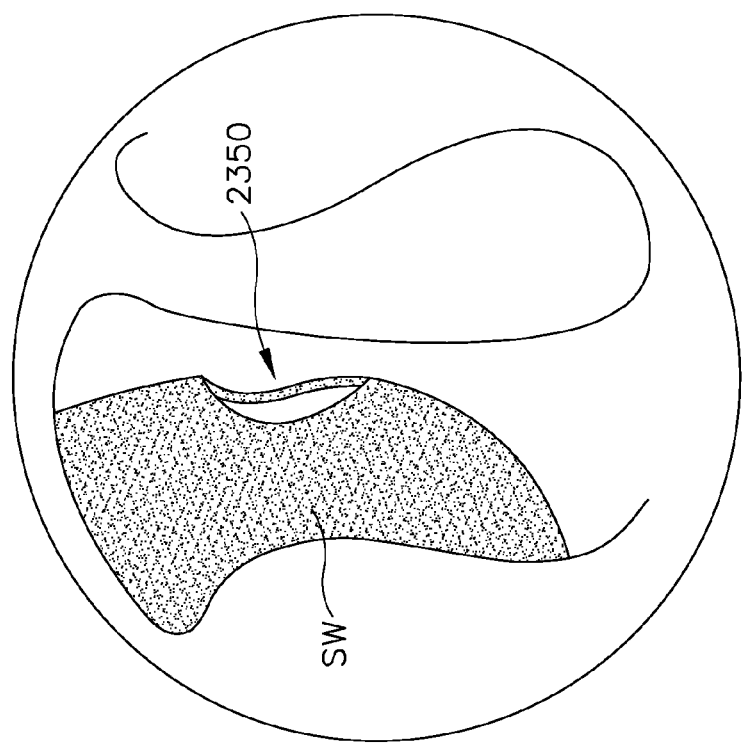
FIG. 30D depicts a perspective view of the sinus wall of FIG. 29A after completion of a procedure with the piercing instrument of FIG. 29A.
Figure 30C:
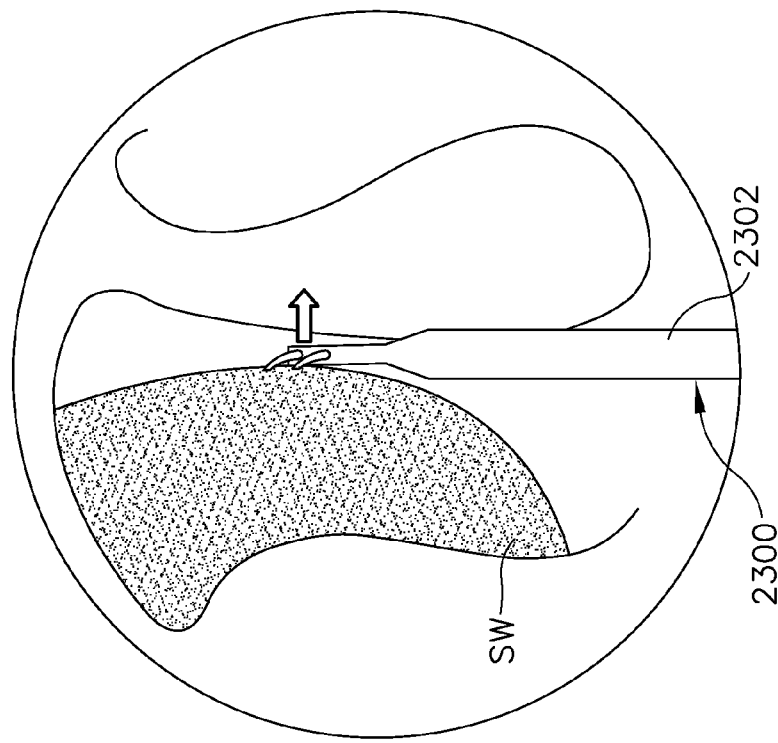
FIG. 30C depicts a perspective view of the distal end of the piercing element of FIG. 29A, with the instrument being pulled away from the sinus wall while the piercing elements are disposed in the sinus wall.

As shown in FIGS. 29A and 30A, instrument (2300) may be initially positioned such that the distal end of shaft (2302) is at a sinus wall (SW) with claw members (2304) in retracted positions. Claw members (2304) are then extended into the sinus wall (SW) while shaft (2302) remains stationary, as shown in FIGS. 29B and 30B. With claw members (2304) disposed in the sinus wall (SW) and held in the extended position, shaft (2302) is then pulled away from the sinus wall (SW), along a path that is generally transverse to the longitudinal axis of shaft (2302), as shown in FIGS. 29C and 30C. This effectively tears away a portion of the sinus wall (SW) that was being grasped by claw members (2304), leaving behind an opening (2350) as shown in FIGS. 29D and 30D. In some versions, the base of each claw member (2304) may be formed into sharp blades extending between claw members (2304), thus allowing the target tissue to be sliced away from the remaining sinus wall (SW) rather than being torn, as claw members (2304) are closed into the positions shown in FIGS. 29C and 30C. Various other suitable features of instrument (2300) and methods of using instrument (2300) will be apparent to those of ordinary skill in the art in view of the teachings herein.

FIGS. 31A-31E show another exemplary instrument (2400) that may be used to form an opening in a sinus wall (SW). The sinus wall (SW) may be a wall of the ethmoid bulla (EB) or the wall of some other sinus cavity. Instrument (2400) of this example comprises an outer cutting sheath (2402) and an inner auger member (2410). Outer cutting sheath (2402) comprises a tapered distal region (2403) terminating in an opening (2404) that is defined by a sharp annular edge. Auger member (2410) comprises a sharp distal tip (2412) and a helical thread (2414). Helical thread (2414) presents an effective outer diameter that increases along the length of auger member (2410). It should be understood that the depicted version of helical thread (2414) is merely illustrative; and that helical thread (2414) may have any suitable thread pitch. Auger member (2410) is operable to longitudinally advance distally relative to cutting sheath (2402) and also rotate relative to cutting sheath (2402).

Figure 31A:
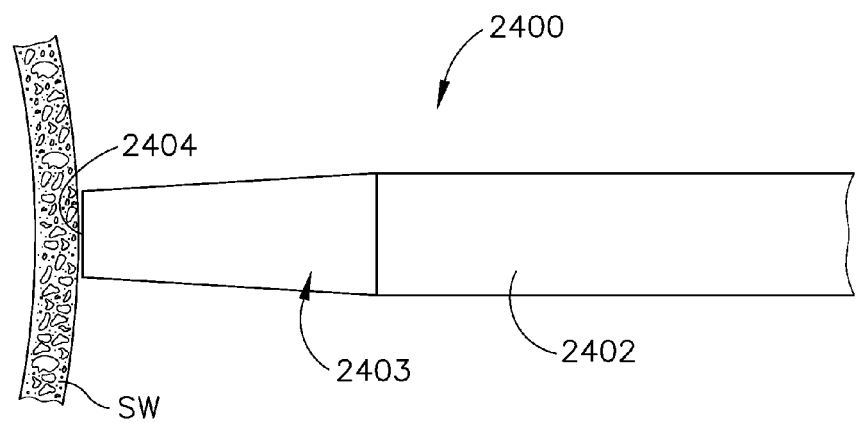
FIG. 31A depicts an elevational view of the distal end of another exemplary alternative sinus wall piercing instrument positioned adjacent to a sinus wall, with the sinus wall in cross section.
Figure 31B:
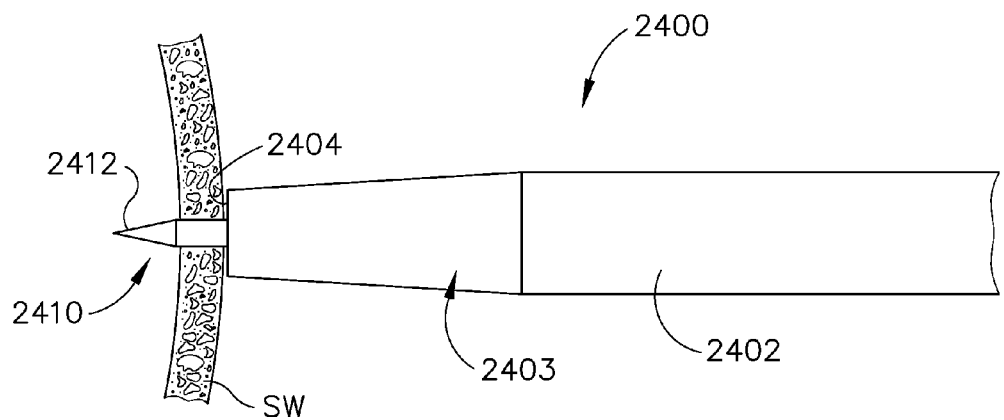
FIG. 31B depicts an elevational view of the distal end of the piercing instrument of FIG. 31A, with the sinus wall in cross section, and with the tip of an auger member disposed in the sinus wall.
Figure 31C:
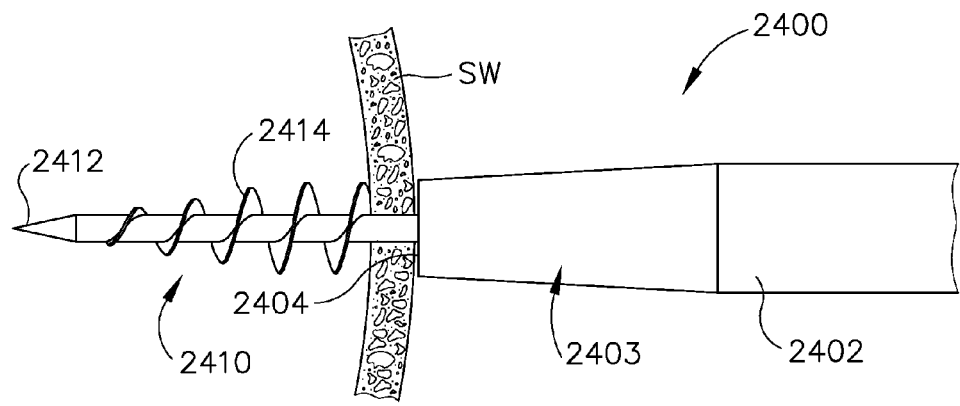
FIG. 31C depicts an elevational view of the distal end of the piercing instrument of FIG. 31A, with the sinus wall in cross section, and with the auger member advanced through the sinus wall.
Figure 31D:
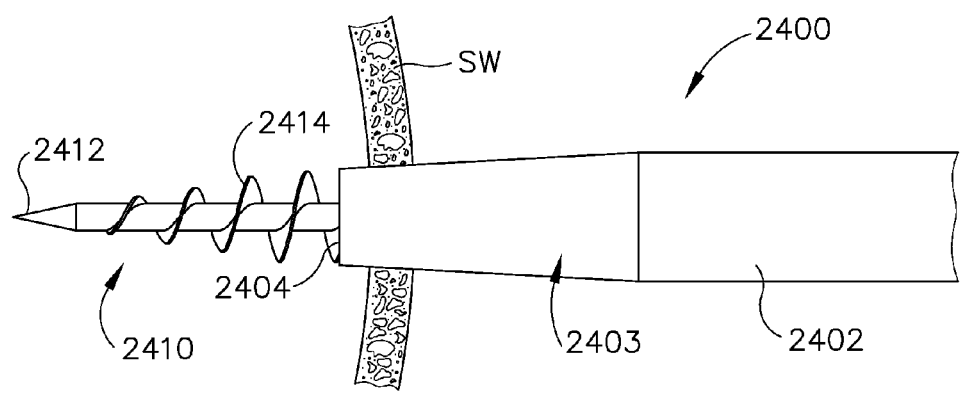
FIG. 31D depicts an elevational view of the distal end of the piercing instrument of FIG. 31A, with the sinus wall in cross section, and with an outer cutter member partially advanced through the sinus wall.
Figure 31E:
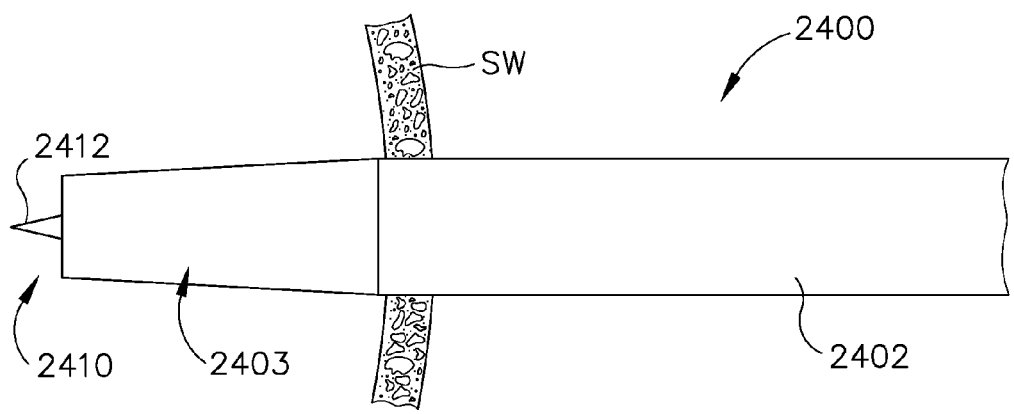
FIG. 31E depicts an elevational view of the distal end of the piercing instrument of FIG. 31A, with the sinus wall in cross section, and with an outer cutter member fully advanced through the sinus wall.
Figure 31F:
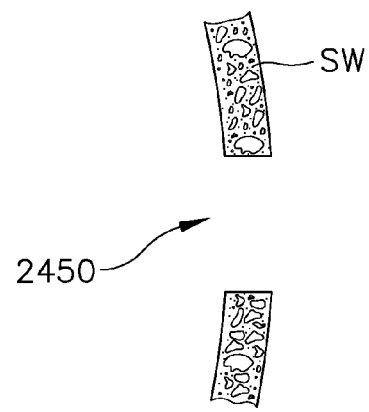
FIG. 31F depicts a cross-sectional view of the sinus wall of FIG. 31A after completion of a procedure with the piercing instrument of FIG. 31A.

As shown in FIG. 31A, instrument (2400) may be initially positioned such that the distal end (2404) of cutting sheath (2402) is at a sinus wall (SW) with auger member (2410) retracted within cutting sheath (2402). Auger member (2410) is then advanced distally such that distal tip (2412) pierces the sinus wall (SW) as shown in FIG. 31B. In some versions, auger member (2410) rotates during this advancement while in other versions it does not. After initially piercing the sinus wall (SW) with distal tip (2412), auger member (2410) continues to advance distally while rotating. This causes helical thread (2414) to drive through the sinus wall (SW) like an auger blade, as shown in FIG. 31C. To this point, cutting sheath (2402) has remained stationary. However, cutting sheath (2402) now is advanced distally while auger member (2410) remains stationary. In some versions, sheath (2402) rotates while it advances distally; while in other versions it does not. When cutting sheath (2402) advances, the sharp edge defining opening (2404) passes through the sinus wall (SW) such that tapered region (2403) is initially disposed in the sinus wall (SW) as shown in FIG. 31D. During this advancement of cutting sheath (2402), auger member (2410) anchors instrument (2400) in the sinus wall (SW) and may further provide structural support to the sinus wall (SW) as cutting sheath (2402) traverses the sinus wall (SW). Sheath (2402) continues to advance distally (either with or without rotation) while auger member (2410) remains stationary, until tapered region (2403) has fully traversed the sinus wall (SW) as shown in FIG. 31E. Tapered region (2403) thus provides a gradual widening of the opening in the sinus wall (SW). Instrument (2400) is then withdrawn from sinus wall (SW), leaving behind an opening (2450) as shown in FIG. 31F. It should be understood that auger member (2410) and/or sheath (2402) may be driven to any depth desired. For instance, auger member (2410) and sheath (2402) may be driven through two or more sinus walls (SW) (e.g., along the same longitudinal path). Various other suitable features of instrument (2400) and methods of using instrument (2400) will be apparent to those of ordinary skill in the art in view of the teachings herein.

FIGS. 32A-32B show an exemplary instrument (2500) that may be used to form openings in two sinus walls (SW) on opposite sides of the nasal septum (NS) substantially simultaneously. In the present example, the sinus walls (SW) are medial walls of the ethmoid bullae (EB), though it should be understood that instrument (2500) may be used on other sinus walls (SW). Instrument (2500) of this example comprises a shaft (2502) having a pair of longitudinally extending arms (2504). The distal end of each arm (2504) includes an outwardly extending piercing element (2506). While piercing elements (2506) are shown as spikes in the present example, it should be understood that piercing elements (2506) may have various other suitable configurations as will be apparent to those of ordinary skill in the art in view of the teachings herein. For instance, piercing elements (2506) may be selectively retractable relative to arms (2504) (e.g., similar to piercing element (1620) of instrument (1600) described above).

Instrument (2500) is operable to move arms (2504) laterally outwardly from a first position to a second position. In particular, as shown in FIG. 32A, arms (2504) are positioned such that piercing elements (2506) are medial to the sinus walls (SW) when arms (2504) are in the first position. It should be understood that arms (2504) are spaced such that arms (2504) may be simultaneously inserted into respective nostrils when arms (2504) are in the first position. As shown in FIG. 32B, arms (2504) drive piercing elements (2506) laterally into the sinus walls (SW) when arms (2504) are moved to the second position. The sinus walls (SW) may provide inwardly directed counteracting forces on arms (2504) as arms (2504) simultaneously move to the second position. In some other versions, arms (2504) are actuated independently/unilaterally. In some such versions, the stationary arm (2504) bears against the lateral wall of the middle turbinate (MT) for support; while the other arm (2504) is actuated to drive piercing element (2506) into the sinus wall (SW). Arms (2504) may be actuated manually by a mechanical linkage, by direct application of the operator's hand force, by hydraulic/pneumatic means such as a balloon, and/or in any other suitable fashion. In some versions, piercing elements (2506) are replaced with atraumatic tissue contact features (e.g., pads) that are pressed against the sinus walls (SW) to deform the sinus walls and thereby remodel a portion of the paranasal cavity. Various other suitable features of instrument (2500) and methods of using instrument (2500) will be apparent to those of ordinary skill in the art in view of the teachings herein.

In any of the foregoing examples of sinus wall piercing (among other examples), it may be desirable to provide some form of structural support to the sinus wall during interaction between the sinus wall and the instrument, to reduce the risk of the sinus wall shattering to an undesirable degree during such interaction. As noted above with respect to instruments (2200, 2400), such support may be provided by the instrument itself. While curved elongate member (2202) and auger member (2410) were used in the examples above, other instrument features that may be used to provide structural support to a sinus wall during piercing will be apparent to those of ordinary skill in the art in view of the teachings herein.

In some other versions, a support material may be introduced into the sinus cavity before the act of piercing with an instrument, again to reduce the risk of the sinus wall shattering to an undesirable degree during piercing/cutting of the sinus wall. By way of example only, such support material may include a sand-like material or a hardening liquid. For instance, a hardening polymer fluid may be introduced into the sinus cavity before the act of piercing with an instrument; and may then be removed after the sinus wall has been pierced. As another merely illustrative example, a hardening biocompatible liquid may be removed with irrigation fluid once the sinus wall has been opened with a piercing element. As yet another merely illustrative example, a material that dissolves through bioabsorption or through some other process (dissolving either shortly after the sinus wall has been pierced or some time thereafter) may be used. Other examples of support material will be apparent to those of ordinary skill in the art in view of the teachings herein. Likewise, various suitable ways in which support material may be introduced to the sinus cavity will be apparent to those of ordinary skill in the art in view of the teachings herein.

In addition to or in lieu of providing a support material, the sinus wall may be frozen in order to add structural integrity to the sinus wall. By way of example only, such freezing may be provided through an applicator that is kept cold; or by the injection of a cold liquid (e.g., liquid nitrogen, etc.). As yet another alternative to providing a support material, an instrument may rely on the inertia of the sinus wall to effectively provide structural integrity. For instance, the tip of the piercing element may be advanced (and perhaps also rotated) at such a rapid rate that the inertia of the sinus wall acts as a support.

IX. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of treating a sinus cavity, the method comprising
   (a) piercing at least one wall of the sinus cavity to form an opening, wherein the act of piercing at least one wall of the sinus cavity comprises:
      (i) piercing the sinus cavity in a first wall location, and
      (ii) piercing the sinus cavity in a second wall location;
   (b) inserting a fluid transfer member through the opening in the at least one wall of the sinus cavity, wherein the fluid transfer member comprises a first port, a second port, and a wick defining a fluid passageway and wherein the fluid transfer member is configured to provide a direct fluid communication path between the interior of the sinus cavity and a region external to the sinus cavity, wherein a portion of fluid transfer member extends into the interior of the sinus cavity, wherein the portion of the at least one fluid transfer member extending into the interior of the sinus cavity is longer than a portion disposed in the opening of the sinus cavity, wherein the wick is configured to transfer fluid medication through a capillary action and to administer the fluid medication directly from the wick to mucosa in the sinus cavity, wherein the act of inserting the fluid transfer member comprises:
- (i) inserting the first port into the first wall location, and
- (ii) inserting the second port into the second wall location so that the first port and the second port are in direct fluid communication with one another via the wick; and (c) administering the fluid medication into a nostril in such a way that the fluid medication travels along the fluid transfer member by way of a capillary action, and is administered directly from the wick to mucosa in the sinus cavity by the wick extending into the interior of the sinus cavity.

2. The method of claim 1, wherein the sinus cavity comprises an ethmoid sinus cell.

3. The method of claim 2, wherein the sinus cavity comprises an ethmoid bulla.

4. The method of claim 1, wherein the first wall location provides a path to an anterior space within the paranasal cavity, wherein the second wall location provides a path to an adjacent sinus cavity.

5. The method of claim 1, wherein the first port has at least one outwardly extending retention feature configured to engage a wall of the sinus cavity.

6. The method of claim 1, wherein the fluid transfer member comprises a bioabsorbable material.

7. The method of claim 1 comprising the step of creating a passageway in an ethmoid sinus, by:
- (a) positioning a piercing element adjacent to the middle turbinate vertical basal lamella; and
- (b) piercing the middle turbinate vertical basal lamella, wherein the act of piercing the middle turbinate vertical basal lamella comprises driving the piercing element into the middle turbinate vertical basal lamella, thereby creating a passageway in the posterior wall of the middle turbinate vertical basal lamella.

8. A method of treating a sinus cavity, the method comprising
- (a) piercing two walls of the sinus cavity to form an opening in both walls;
- (b) inserting a fluid transfer member through the opening in the two walls of the sinus cavity, wherein the fluid transfer member comprises a first port, a second port, and a wick defining a fluid passageway and wherein the fluid transfer member is configured to provide a direct fluid communication path between the interior of the sinus cavity and a region external to the sinus cavity, wherein the wick extends into the interior of the sinus cavity, wherein the first port is disposed in the opening of a first wall of the two walls, wherein the second port is disposed in the opening of a second wall of the two walls, wherein the wick provides direct fluid communication between the first port and the second port, wherein a portion of the fluid transfer member extending into the interior of the sinus cavity is longer than a portion disposed in the opening of the sinus cavity, wherein the wick is configured to transfer fluid medication through a capillary action and to administer the fluid medication directly from the wick to mucosa in the sinus cavity; and
- (c) administering the fluid medication into a nostril in such a way that the fluid medication travels along the fluid transfer member by way of a capillary action, and is administered directly from the wick to mucosa in the sinus cavity by the fluid transfer member extending into the interior of the sinus cavity.

\* \* \* \* \*